US007269517B2

(12) United States Patent
Bondarenko

(10) Patent No.: US 7,269,517 B2
(45) Date of Patent: Sep. 11, 2007

(54) COMPUTER SYSTEMS AND METHODS FOR ANALYZING EXPERIMENT DESIGN

(75) Inventor: Andrey Bondarenko, Redmond, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 634 days.

(21) Appl. No.: 10/419,027

(22) Filed: Apr. 18, 2003

(65) Prior Publication Data

US 2005/0055193 A1 Mar. 10, 2005

(51) Int. Cl.
*G06F 19/00* (2006.01)
*G06G 7/60* (2006.01)

(52) U.S. Cl. ............................................ 702/19; 703/11
(58) Field of Classification Search .................... None
See application file for complete search history.

(56) References Cited

U.S. PATENT DOCUMENTS

| 5,510,270 | A | | 4/1996 | Fodor et al. |
| 5,539,083 | A | | 7/1996 | Cook et al. |
| 5,578,832 | A | | 11/1996 | Trulson et al. |
| 6,408,308 | B1 | * | 6/2002 | Maslyn et al. ............ 707/104.1 |

FOREIGN PATENT DOCUMENTS

| EP | 0 534 858 A1 | 9/1992 |
| WO | WO98/41531 | 9/1998 |
| WO | WO 02/44399 A2 | 6/2002 |

OTHER PUBLICATIONS

Bannon Information technology: basic principles Current Paediatrics vol. 6, pp. 38-41 (1995).*
Blanchard, 1998, "Synthetic DNA Arrays," Genetic Engineering 20:111-123.
Blanchard et al., 1996, "High-density oligonucleotide arrays," Biosensors and Bioelectronics 11:687-690.
Bochner et al., 2001, "Phenotype Microarrays for High-Throughput Phenotypic Testing and Assay of Gene Function," Genome Research 11:1246-1255.
Brown et al., 1994, "Chemometrics," Anal Chem 66:22R-49R.
Brown et al., 1999, "Exploring the new world of the genome with DNA microarrays," Nature Genetics Supplement 21:33-37.
Churchill, 2002, "Fundamentals of experimental design for cDNA microarrays," Nature Genetics Supplement 32:490-495.
DeRisi et al., 1996, "Use of a cDNA microarray to analyse gene expression patterns in human cancer," Nature Genetics 14:457-460.
Drăghici, 2003, *Data Analysis Tools for DNA Microarrays*, Chapman & Hall/CRC, London, U.K.
Eisen et al., 1999, "DNA Arrays for Analysis of Gene Expression," Methods in Enzymology 303:179-205.
Ferguson et al., 1996, "A fiber-optic DNA biosensor microarray for the analysis of gene expression," Nature Biotechnology 14:1681-1684.
Frank, 1990, "A Nonlinear PLS Model," Chemometrics and Intelligent Laboratory Systems 8:109-119.

Golub et al., 1999, "Molecular Classification of Cancer: Class Discovery and Class Prediction by Gene Expression Monitoring," Science 286:531-537.
Hastie et al., 1995, "Penalized Discriminant Analysis," The Annals of Statistics 23:73-102.
Helm et al., 1991, "Classification and identification of bacteria by Fourier-transform infrared spectroscopy," Journal of General Microbiology 137:69-79.
Hoskuldsson, 1992, "Quadratic PLS Regression," Journal of Chemometrics 6:307-334.
Jarvis et al., 1973, "Clustering Using a Similarity Measure Based on Shared Near Neighbors," IEEE Transactions on Computers C-22:1025-1034.
Kerr et al., 2001, "Experimental design for gene expression microarrays," Biostatistics 2:183-201.
Kvalheim et al., 1985, "Crude Oil Characterization and Correlation by Principal Component Analysis of $^{13}C$ Nuclear Magnetic Resonance Spectra," Anal Chem 57:2858-2864.
Lance et al., 1967, "A general theory of classificatory sorting strategies: 1. Hierarchical systems," Computer Journal 9:373-380.
Lander, 1996, "The New Genomics: Global Views of Biology," Science 274:536-539.
Lander et al., 2001, "Initial sequencing and analysis of the human genome," Nature 409:860-921.
Lockhart et al., 1996, "Expression monitoring by hybridization to high-density oligonucleotide arrays," Nature Biotechnology 14:1675-1680.
Naumann et al., 1991, "Microbiological characterizations by FT-IR spectroscopy," Nature 351:81-82.
Nguyen et al., 1995, "Differential Gene Expression in the Murine Thymus Assayed by Quantitative Hybridization of Arrayed cDNA Clones," Genomics 29:207-216.
Nguyen et al., 2002, "DNA Microarray Experiments: Biological and Technological Aspects," Biometrics 58:701-717.
Prashar et al., 1996, "Analysis of differential gene expression by display of 3' end restriction fragments of cDNAs," Proc. Natl. Acad. Sci. USA 93:659-663.
Sagliocco et al., 1996, "Identification of Proteins of the Yeast Protein Map using Genetically Manipulated Strains and Peptide-Mass Fingerprinting," Yeast 12:1519-1533.
Schena et al., 1995, "Quantitative monitoring of gene expression patterns with a complementary DNA microarray," Science 270:467-470.
Schena et al., 1996, "Parallel human genome analysis; Microarray-based expression monitoring of 1000 genes," Proc. Natl. Acad. Sci. USA 93:10614-10619.

(Continued)

*Primary Examiner*—John S Brusca
(74) *Attorney, Agent, or Firm*—Jones Day

(57) ABSTRACT

An experiment definition system that digitally represents an experiment design. The experiment definition provides the logical structure for data analysis of scans from one or more biological experiments. The experiment definition either directly reflects the experiment design in a one-to-one relationship, or the user customizes the experiment definition. Experiment definitions are stored as a set of instructions in a database of experiment definitions. A user interface for constructing the experiment definition, and for customizing one or more automated analysis pipelines for processing the experiment definitions.

163 Claims, 28 Drawing Sheets

OTHER PUBLICATIONS

Shalon et al., 1996, "A DNA Microarray System for Analyzing Complex DNA Samples Using Two-color Fluorescent Probe Hybridization," Genome Research 6:639-645.

Shevchenko et al., 1996, "Linking genome and proteome by mass spectrometry: Large-scale identification of yeast proteins from two dimensional gels," Proc. Natl. Acad. Sci. USA 93:14440-14445.

Velculescu et al., 1995, "Serial Analysis of Gene Expression," Science 270:484-487.

Venter et al., 2001, "The Sequence of the Human Genome," Science 291:1304-1351.

Wold, 1991, "Nonlinear partial least squares modelling—II. Spline inner relation," Chemometrics and Intelligent Laboratory Systems 14:71-84.

Wolfinger et al., 2001, "Assessing Gene Significance from cDNA Microarray Expression Data via Mixed Models," Journal of Computational Biology 8:625-637.

Wythoff, 1993, "Orthonet: orthogonal latent variable neural network," Chemometrics and Intelligent Laboratory Systems 20:129-148.

Yang et al., 2002, "Comparison of Methods for Image Analysis on cDNA Microarray Data," Journal of Computational and Graphical Statistics 11:108-136.

Yang et al., 2002, "Design Issues for cDNA Microarray Experiements," Nature Reviews 3:579-588.

* cited by examiner

| Exp Definition | Assigned Ratio Experimen... | User Defined Ratio Experiment Name | Experiment De... | Experim |
|---|---|---|---|---|
| 11,344 | UHR: 25 % vs. UHR: 0 | UHR: 25 % vs. UHR: 0 | | |
| 11,344 | 293: 0 vs. UHR: 100 % | 293: 0 vs. UHR: 100 % | | |
| 11,344 | UHR: 50 % vs. UHR: 0 | UHR: 50 % vs. UHR: 0 | | |
| 11,344 | 293: 25 % vs. UHR: 100 % | 293: 25 % vs. UHR: 100 % | | |
| 11,344 | UHR: 75 % vs. UHR: 0 | UHR: 75 % vs. UHR: 0 | | |
| 11,344 | 293: 50 % vs. UHR: 100 % | 293: 50 % vs. UHR: 100 % | | |
| 11,344 | 293: 75 % vs. UHR: 0 | 293: 75 % vs. UHR: 0 | | |
| 11,344 | 293: 100 % vs. UHR: 100 % | 293: 100 % vs. UHR: 100 % | | |

| Experiment definition 1350-1 | | |
|---|---|---|
| Name | | ~1402 |
| Type: Factorial | | |
| Factor 1452-1-1 | | |
| | Level 1454-1-1-1 | |
| | ⋮ | |
| | Level 1454-1-N-1 | |
| Factor 1452-2-1 | | |
| | Level 1454-2-1-1 | |
| | ⋮ | |
| | Level 1454-2-P-1 | |
| ⋮ | | |
| Factor 1452-Q-1 | | |
| | Level 1454-Q-1-1 | |
| | ⋮ | |
| | Level 1454-Q-F-1 | |
| Instructions for profile builder pipeline 405 | | ~1480 |
| Instructions for ratio builder pipeline 450 | | ~1482 |
| Instructions for experiment builder pipeline 415 | | ~1484 |
| Instructions for analysis pipeline 412 | | ~1486 |
| ⋮ | | |

FIG. 14

COMPUTER SYSTEMS AND METHODS FOR ANALYZING EXPERIMENT DESIGN

1. FIELD OF THE INVENTION

The present invention relates to an experiment definition for digitally representing experiment designs, and an experiment definition system for storing and implementing experiment definitions.

2. BACKGROUND OF THE INVENTION

The majority of measurement experiments in modern science use the theory of experiment design. While an experimental method supplies a methodology for establishing a body of reliable facts and analyses which can aid in answering certain clearly stated questions relevant to an experimenter, an experiment design is the plan for collecting and analyzing data to answer certain clearly stated questions relevant to the needs of the experimenter. The experiment design is based on contrasting two or more treatment conditions, where ideally the subjects are treated in identical manners, except for one feature that is different. An observed difference in response can then be attributed to the designed differences among the treatment conditions. A well designed experiment permits the inference of facts from a small number of observations that might otherwise require an exhaustive set of observations. The results of an experiment can indicate how to change an average response of a system to a different desired value in response to a treatment. Alternately, the results of an experiment can show how to reduce variations in a process, help to make a process more robust or even help to distinguish which variables are important to control. Experimental investigations are generally iterative in nature, and the experimenter generally uses the results of, e.g., a screening process, to decide on the factors that are important to control in the following experimental design. Some basics of the design of experiments are summarized at trochim.human.cornell.edu/kb/desintro.htm. There are also commercially available texts that provide a discussion of the design of experiments, such as Barrentine, *An Introduction to Design of Experiments: A Simplified Approach*, ASQ Quality Press, 1999.

An experiment design provides the structuring of an experiment for the application of a number of treatments to one or more experimental units, i.e., a number of different subjects on which the experiment is performed (e.g., animals or cells). The factors, which form the independent variables, are the controllable settings in the experiment, and are typically represented by Xs, i.e. $X_1, X_2, X_3$, etc. Each factor can have one or more values, subdivisions or settings, each referred to as a level of the factor, an example being the different concentrations of a drug. The experiment design specifies the levels for the factors for each performance of the experiment. A response value or setting forms the dependent variable, and is the measured outcome from the performance of an experiment. In an experiment design, the factors are chosen by the experimenter in the belief that they should affect the response value being monitored. To increase the confidence level in the results of an experiment, the experimenter can choose to form a number of replications.

A replication is a repetition of some or all treatments on two or more experiment units. If all of the experiments are repeated three times, the study is said to have three replications. Replications of experiments are necessary to provide an indication of the amount of the experiment error in the measurement of any response value. An experiment design specifies the number of experiments, the factor-level combination for each of the experiments, and the number of replications of the experimental study. The different response values or settings from the different replications of the scans performed, also called replicates, are used to calculate a statistical average of response to the application of a factor. For balance, it is preferable to have an equal number of observations for each treatment. This helps to minimize the possibility of some types of bias. Increasing the number of replicates can help increase the statistical confidence in the correlations of the responses between levels, such as a confidence level of 95%. An example of a software tool that can compute a minimal number of replicates is BioMine™ 1.0 Experiment Design Tool™ (available from Gene Network Sciences, Inc., Ithaca, N.Y.).

An experiment design can also indicate if there is any interaction between factors when the levels of the factors are applied in combination in an experimental design. Two factors A and B are said to interact if the effect of one depends on the level of the other, such as if the factors are time and dosage levels of a drug. An interaction graph can help to visualize interactions between two factors, e.g., if the response variable is plotted as the y-axis, the x-axis is the levels of one of the factors, and each curve plotted on the interaction graph represents the responses to the levels of the other factor. A main effect is an outcome where there is a consistent difference between levels of a factor on an interaction graph. For example, there is a main effect from a factor such as a drug if there is a statistical difference between the average response for the different drug dosage levels at all levels of time in an experimental study.

FIGS. 1A, 1B and 1C illustrate interaction graphs for an experiment design where the two factors of drugs and time are applied, each at two different levels. The levels of the factor time on the x-axis and 1 hour and 4 hours, while the levels of the factor drugs on the x-axis are drug dosages of level 1 ng/ml and 10 mg/ml. FIG. 1A depicts an interaction graph where there is no effect of any treatment condition, since the effect of the drug and time are the same. FIGS. 1B and 1C depict interaction graphs where there is a main effect only for time, or only for drugs, respectively. FIG. 1B shows that, for all drug dosage levels, the 4 hours condition has a greater effect than the 1 hour condition. FIG. 1C shows that the 10 ng/ml dosage level yields a greater effect than the 1 ng/ml level, for any given amount of time. The interaction graphs can also show a main effect for both factors. FIG. 2A illustrates an interaction graph for the case where there is a main effect for both factors, but with no interaction. FIGS. 1A, 1B, 1C and 2A all show that, if there is no interaction, the curves on the graph are basically parallel. Any amount of interaction will be exhibited by some amount of deviation from a parallel arrangement. FIG. 2B, illustrates the case where there is an interaction between the factors drug and time, but only for the case where time is 4 hours and drug is 10 ng/ml. FIG. 2B illustrates a case of a more complex "cross-over" interaction between the two factors, where the combinations of 1 hour and 1 ng/ml or 4 hours and 10 ng/ml worked equally as well, while the other combinations do poorly. A poorly designed experiment could also lead to confounding, which is an inability to attribute a change in a response variable to a factor. A good experiment design works to reduce the incidence of confounding.

There are many different statistical analysis methods that can be used to analyze the measurements derived from any particular experiment design chosen. In many statistical tests, any measurement error is required to be independent of the measurement quantity (constant measurement variance). Analysis of Variance (ANOVA) is an example (see, e.g., Statistics For Experimenters, Box, Hunter and Hunter, John Wiley and Sons, 1978; Siegel et al., Nonparametric statistics for the behavioural sciences, McGraw Hill, $2^{nd}$ edition, 1998; Conover, Practical Nonparametric Statistics, John Wiley and Sons, $3^{rd}$ edition, 1998; Altman, Practical Statistics for Medical Research, CRC Press, 1991; Berry, Statistical Methods in Medical Research, Blackwell Science, Inc., 2001). ANOVA is a method for detecting whether there are statistical differences among the mean of different measurement groups. ANOVA can be used to determine whether there is a statistically significant difference in protein expression data between or within groups of genes. Examples of standard statistical techniques applied to analyze the measured results of an experiment design include t-tests (paired and unpaired), one-way or two-way ANOVA, factorial and fractional factorial designs (e.g., two-level designs), the method of least squares (linear or nonlinear models), and response surface methodology. The statistical analysis methods are used to interpret the data derived from the experiment design, i.e., to indicate if any observed difference in the main effects between groups from the one or more factors is actually statistically valid.

There are software tools available in the art for storing and manipulating data derived from various experiments in biotechnology, or for performing some statistical analysis of the data. BioMine™ 1.0 (see gnsbiotech.com/biomine.shtml) is an application for the analysis of gene expression data that provides for data importation and normalization (from e.g., replicates). The application also provides for some manipulation of the normalized data, e.g., an Experiment Design Tool™ that computes the minimal number of replicates for statistically validating an experiment result within a given confidence level. Rosetta Biosoftware provides a flexible, manipulable searchable database, i.e., the Rosetta Biosoftware Resolver® gene expression data analysis system (Rosetta BioSoftware, Kirkland, Wash.), which can be used to store, and search a compilation of, e.g., gene expression data sets. Silicon Genetics (Redwood City, Calif.) provides different software tools for raw data normalization, analysis, and visualization, called GeneSpring™ software version 5.0, which is a visualization software package for, e.g., microarray data, and GeNet™ software version 3.0, which is provides for data archiving and retrieval by assigning attributes to gene expression profiles. Affymetrix, Inc. (Santa Clara, Calif.) provides the Affymetrix® Analysis Data Model (AADM), a relational database schema used to store Affymetrix® GeneChip expression results, and Data Mining Tool (DMT) software tools for filtering and sorting GeneChip® array data stored in an Affymetrix® Analysis Data Model (AADM)-compatible database generated by using the Laboratory Information Management System (LIMS) or MicroDB™ (which creates Affymetrix® Analysis Data Model (AADM)-compliant databases from experimental data sets derived from GeneChip® or spotted arrays).

While the Rosetta Resolver® software tools provided a searchable database for gene expression data analysis, the software package does not provide a user interface (UI) tool for processing experiment data according to an experiment definition, or the capability for saving the experiment definition instructions on how to process the data. Prior implementations of analysis tools in currently available systems, e.g., Rosetta Resolver®, require the user to go through many labor-intensive steps, such as multiple data searches, managers, and complex wizards to arrive at a result. As an example, a user has to search for different components in different parts of the application. For instance, profiles related to a project are searched among all profiles, experiments among all experiments, cluster results among all clusters, etc. Additionally, currently available systems treat each profile separately, and thus it is difficult to assign different profiles to more than one treatment group.

Given the above background, there remains a need for an experiment definition system that can digitally reflect an experiment design. Such a system should provide the experimenter with a user-interface that allows digital manipulation, organization and analysis of the results of any number of different measurements according to any desired experiment design, and provide processing and analysis pipelines for implementing the experiment definitions. The experiment definition system should also be able to store the experiment definitions customized by the user for further use. Such an experiment definition system would offer increased flexibility over the existing software tools.

3. SUMMARY OF THE INVENTION

The present method addresses the shortcomings of the known software tools. The invention provides a user-interface that allows digital manipulation, organization and analysis of the results of any number of different measurements according to any desired experiment design, and provides processing and analysis pipelines for implementing the experiment definitions. The experiment definition system also provides for storage of the user-customized experiment definitions.

A first aspect of the invention provides a method for processing a plurality of scans from one or more biological experiments. In the method, a plurality of scans are assigned to an experiment definition, which is stored in a database of experiment definitions. The plurality of scans are processed by executing the experiment definition. In different embodiments, the experiment definition is executed before it is stored in the database of experiment definitions, or it is first stored in the database before it is executed. An experiment definition can also be selected from the database of experiment definitions. In an embodiment of the first aspect, the database of experiment definitions is a relational database, for example, an Oracle9i database.

The scans can be intensity measurements in a spatial array. The plurality of scans can comprise between 10 and 100 intensity measurements, more than 100 intensity measurements, or less than 10000 intensity measurements. In specific embodiments, the plurality of scans comprise between 100 and 500 intensity measurements, between 500 and 1000 intensity measurements, between 1000 and 5000 intensity measurements or between 5000 and 10000 intensity measurements in the spatial array.

In some embodiments, one or more scans of the plurality of scans represents data from a microarray or a two-dimensional gel. The scans can represent different densities of probes of a microarray. The probes can be arranged with a density of 100 non-identical probes per 1 $cm^2$ or higher, at least 2,500 different probes per 1 $cm^2$ or at least 20,000 probes.

The plurality of scans can represent levels of a plurality of cellular constituents in a biological sample that are measured during one or more biological experiments. Examples of such cellular constituents include, but are not limited to, genes, proteins, mRNA, cDNA, cRNA, and degrees of protein modification.

In some embodiments of the invention, the experiment definition is a combinatorial experiment definition. The assignment of the plurality of scans to the experiment definition comprises defining one or more treatment groups. Each scan of the plurality of scans is assigned to a treatment group of the one or more treatment groups.

In some embodiments according to the first aspect of the invention, the experiment definition is a factorial design experiment definition, defined by one or more experimental factors, and the one or more levels that correspond to each experimental factor. A factorial design experiment definition can comprise two, three, four, up to ten, or more than ten experimental factors. Examples of such experimental factors include, but are not limited to, time, compound type, compound dosage, tissue type, and species. In some embodiments, an experimental factor is designated as a trend factor. In embodiments where a ratio or re-ratio experiment is built, a baseline can be used. There are a number of ways in which a baseline can be created. For example, one of the levels of one of the experimental factors can be marked as a baseline. Alternatively, the average of all of the scans in the experimental definition can be used as a baseline. In still another example, the average of any specified scans within or outside the experimental definition can be used as a baseline. In still another embodiment, a baseline can be established using one level of the experimental factor with or without partitioning across other experimental factors by averaging all scans in the selected level across all other experimental factors. In addition, custom sets of scans from treatment groups can be used independently or in conjunction with other techniques to establish a baseline.

For a factorial design experiment definition, the database is structured as an n-dimensional datacube, where the cubes of the n-dimensional datacube are generated by the cross product of the levels of the one or more experimental factors of the factorial design experiment definition. For example, for a two-factor factorial design, the datacube is a two-dimensional datacube, and for a three-factor factorial design, it is a three-dimensional datacube. The plurality of scans are each independently assigned to the various cubes of the n-dimensional datacube. In some embodiments, replicates are assigned to a given cube of the n-dimensional datacube, where the actual replicates count assigned to a cube may differ from the replicates count expected to be assigned. In some embodiments of the first aspect of the invention, the one or more scans are assigned to only a portion of the cubes in the n-dimensional datacube.

In a second aspect of the invention, execution of the experiment definition of the first aspect of the invention further comprises applying an error correction model for correcting errors in the plurality of scans. The intensity measurements in each scan of the plurality of scans is normalized. Examples of normalization protocols include, but are not limited to, a Z-score of intensity protocol, a median intensity normalization protocol, a log median intensity protocol, a Z-score standard deviation log of intensity protocol, a Z-score mean absolute deviation of log intensity protocol, a user normalization gene set protocol, and a ratio median intensity correction protocol. One of a plurality of possible error correction models is also applied to the scan. The normalized, error corrected scan data is stored as a profile that corresponds to the scan. In some embodiments, the experiment definition specifies a ratio between experimental factors or levels in a first set of profiles and experimental factor or levels in a second set of profiles, where each profile corresponds to a scan in the plurality of scans. In other embodiments, the experiment definition specifies instructions for combining a plurality of the profiles, where each scan corresponding to a profile is a replicate. The plurality of profiles are combined to form a replicate profile using the instructions specified by the experiment definition for the combining.

In some embodiments in accordance with the second aspect of the invention, the experiment definition specifies instructions for analyzing the plurality of profiles. These data analysis instruction sets can be selected from a plurality of data analysis instruction sets. In some embodiments, the data analysis instructions for analyzing the profiles are for applying a classification scheme to the intensity measurements in the plurality of profiles. The classification scheme can be a supervised or unsupervised classification scheme. An embodiment of a supervised classification scheme is a linear discriminant analysis or linear regression. Examples of such schemes include, but are not limited to, multiple linear regression, partial least squares regression, principal component analysis and principle component regression. An embodiment of a unsupervised classification scheme is a hierarchical cluster analysis. Examples of such schemes include, but are not limited to, a hierarchical cluster analysis, non-hierarchical cluster analysis, a neural network, a self-organizing map, k-means clustering, and Jarvis-Patrick clustering. The agglomerative clustering can use, for example, a nearest neighbor algorithm, a farthest-neighbor algorithm, an average linkage algorithm, a centroid algorithm, or a sum of squares algorithm. In some embodiments, the data analysis instructions for analyzing the profiles are for applying a parametric statistical test. The parametric statistical test can comprise, for example, a fractional factorial design, analysis of variance, a t-test, least squares, a Pearson correlation, simple linear regression, nonlinear regression, multiple linear regression, or multiple nonlinear regression. Alternatively, the parametric statistical test can comprise a one-way analysis of variance, two-way analysis of variance, or repeated measures analysis of variance. In other embodiments, the data analysis instructions specify the application of a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test.

A third aspect of the invention provides a data structure. The data structure comprises an n-dimensional data cube formed by the cross product of each level of each experimental factor in a plurality of experimental factors. In some embodiments, the datacube is a two-dimensional or a three-dimensional data cube. The datacube has higher dimensionality when the cells are cross products of the levels of four or more experimental factors, up to ten, or more than ten experimental factors. The data structure also comprises a plurality of scans from one or more biological experiments that are assigned to at least one cell in the n-dimensional data cube, and the instructions for processing the scans. In some embodiments, a single scan or more than one scan is assigned to a cell in the n-dimensional data cube. The one or more biological experiments can comprise, for example, microarray or two-dimensional gel experiments.

As is the case for the first aspect of the invention, an experimental factor can be specified as a trend factor or as a baseline for a ratio or re-ratio experiment. As non-limiting examples, each experimental factor of the plurality of experimental factors represents time, compound type, compound dosage, tissue type, or species in the one or more biological experiments.

In some embodiments according to the third aspect of the invention, the instructions for processing the one or more scans comprise instructions for correcting errors in the scans. These include instructions for normalizing intensity measurements in each scan, for example, corresponding to those listed for other aspects of the invention. There are also instructions for storing, as a profile in the data structure, scan data that has been error corrected and normalized, where there is a one to one correspondence between each scan and each profile. In some embodiments, the profile is stored in the cell in the n-dimensional data cube where the corresponding scan is stored. In some embodiments, the instructions specify taking a ratio between an experimental factor or a level in a first set of profiles and an experimental factor or level in a second set of profiles, each corresponding to scans in the plurality of scans. In other embodiments, the instructions are for combining a plurality of profiles, where each of the scans corresponding to the profiles to be combined are replicates. In yet other embodiments, the instructions are for analyzing a plurality of profiles, for example, corresponding to the analyses listed for the second aspect of the invention. The data structure can be stored in a relational database, such as an Oracle9i database.

A fourth aspect of the invention provides a computer program product for use in conjunction with a computer system. The computer program product comprises a computer readable storage medium and an embedded computer program mechanism. The computer program mechanism comprises a database having a plurality of experiment definitions. The mechanism also comprises an experiment definition system for processing a plurality of scans from one or more biological experiments. The experiment definition system comprises instructions for assigning the plurality of scans to an experiment definition, instructions for storing the experiment definition in the database, and instructions for executing the experiment definition for processing the plurality of scans. The instructions for executing the experiment definition can be executed at a time prior to or subsequent to the instruction for storing the experiment definition in the database.

In some embodiments according to the fourth aspect of the invention, the experiment definition is a factorial design experiment definition. The instructions for assigning the plurality of scans to the experiment definition comprise (i) instructions for generating an n-dimensional datacube by taking the cross product of a level from each of the one or more experimental factors defined in the experiment definition; (ii) instructions for assigning a scan to a cube in the n-dimensional datacube; and (iii) instructions for repeating the instructions for assigning scans to cubes until each scan in the plurality of scans has been assigned to a cube in the n-dimensional datacube. In some embodiments, only a portion of the cubes in the n-dimensional datacube are assigned one or more scans. Replicates can be assigned to a first cube in the n-dimensional datacube, where the first cube has an expected and actual replicates count. In some embodiments, the n-dimensional datacube is a two-dimensional datacube, a three-dimensional datacube or has a higher dimension if between four and ten experimental factors, or more then ten experimental factors are assigned. As for the other aspects of the invention, the fourth aspect of the invention can include instructions for designating an experimental factor of the one or more experimental factors as a trend factor, or for marking a level in an experimental factor in the one or more experimental factors as a baseline for building a ratio or re-ratio experiment.

In some embodiments according to the fourth aspect of the invention, the experiment definition further comprises an error correction model for correcting errors in the plurality of scans. For each scan in the plurality of scans, such instructions for executing the experiment definition includes (i) instructions for normalizing intensity measurements in the scan; (ii) instructions for applying the error correction model to a scan; and (iii) instructions for storing the normalized, corrected scan data as a profile that corresponds to the scan. In some embodiments, the experiment definition further comprises instructions for specifying a ratio between an experimental factor or a level in a first set of profiles and an experimental factor or a level in a second set of profiles, where the instructions for executing the experiment definition comprise instructions for taking the ratio between experimental factors or levels in the sets of profiles. In other embodiments, the experiment definition further comprises instructions for combining a plurality of profiles, where each scan corresponding to a profile is a replicate, and where the instructions for executing the experiment definition further comprises instructions for combining the plurality of profiles to form a replicate profile. In yet other embodiments, the experiment definition further comprises instructions for analyzing a plurality of profiles, where the instructions for executing the experiment definition further comprises instructions for analyzing the plurality of profiles.

In some embodiments according to the fourth aspect of the invention, the instructions for assigning the plurality of scans to an experiment definition further comprise instructions for selecting the experiment definition from the database comprising the plurality of experiment definitions.

In some embodiments according to the fourth aspect of the invention, the instructions for processing the one or more scans comprise instructions for correcting errors in the scans. These include instructions for normalizing intensity measurements in each scan, for example, corresponding to those listed for other aspects of the invention. There are also instructions for storing, as a profile in the data structure, scan data that has been error corrected and normalized, where there is a one to one correspondence between each scan and each profile in a given experiment definition. The profile is stored in the cell in the n-dimensional data cube where the corresponding scan is stored. In some embodiments, the instructions specify taking a ratio between experimental factor or levels in a first set of profiles and a second set of profiles, each corresponding to scans in the plurality of scans. In other embodiments, the instructions are for combining a plurality of profiles, where each of the scans corresponding to the profiles to be combined are replicates. In yet other embodiments, the instructions are for analyzing a plurality of profiles, for example, corresponding to the analyses listed for other aspects of the invention.

In some embodiments according to the fourth aspect of the invention, the database that comprises the plurality of experiment definitions is a relational database, such as an Oracle9i database.

In some embodiments according to the fourth aspect of the invention, where the experiment definition is a combinatorial experiment definition, the instructions for assigning the plurality of scans to the experiment definition comprise (i) instructions for defining one or more treatment groups; (ii) instructions for assigning a scan to a treatment group in the one or more treatment groups; and (iii) instructions for repeating the assignment of scans to treatment groups until each scan in the plurality of scans has been assigned to a treatment group.

A fifth aspect of the invention provides a computer system for processing a plurality of scans from one or more biological experiments. The computer system comprises a central processing unit, and a memory, coupled to the central processing unit. The memory stores a database that comprises a plurality of experiment definitions and an experiment definition system, where the experiment definition system comprises instructions for assigning the plurality of scans to an experiment definition, instructions storing the experiment definition in the database, and instructions for executing said experiment definition for processing the plurality of scans.

In some embodiments according to the fifth aspect of the invention, the experiment definition is a factorial design experiment definition. The instructions for assigning the plurality of scans to the experiment definition comprises (i) instructions for generating an n-dimensional datacube by defining one or more experimental factors and defining one or more levels for each experimental factor, where each cube in the n-dimensional datacube is the cross product of a level from each of the one or more experimental factors; (ii) instructions for assigning a scan to a cube in the n-dimensional datacube; and (iii) instructions for repeating the assignment of scans to cubes until each scan in the plurality of scans has been assigned to a cube in the n-dimensional datacube. In some embodiments, the experiment definition further comprises instructions for specifying a ratio between experimental factors or levels in a first set of profiles and a second set of profiles. In other embodiments, the experiment definition further comprises instructions for combining a plurality of profiles, where each scan that corresponds to a profile in the plurality of profiles is a replicate, and the instructions further comprise instructions for combining the plurality of profiles to form a replicate profile. In yet other embodiments, the experiment definition further comprising instructions for analyzing a plurality of profiles.

In some embodiments according to the fifth aspect of the invention, the experiment definition further comprises an error correction model for correcting errors in the plurality of scans. For each scan in the plurality of scans, the instructions for executing the experiment definition comprises (i) instructions for normalizing intensity measurements in said scan; (ii) instructions for applying said error correction model to a scan; and (iii) instructions for storing the normalized, error-corrected scan data as a profile that corresponds to the scan.

In some embodiments according to the fifth aspect of the invention, a scan in the plurality of scans represents a microarray or a two-dimensional gel.

In some embodiments according to the fifth aspect of the invention, where the experiment definition is a combinatorial experiment definition, the instructions for assigning the plurality of scans to the experiment definition comprises (i) instructions for defining one or more treatment groups; (ii) instructions for assigning a scan to a treatment group in the one or more treatment groups; and (iii) instructions for repeating the assignment of scans to treatment groups until each scan in the plurality of scans has been assigned to a treatment group.

The present invention provides a data structure comprising: an n-dimensional data cube, wherein each cell in the n-dimensional data cube is formed by the cross product of a level of each experimental factor in a plurality of experimental factors, wherein a plurality of scans from one or more biological experiments are assigned to at least one cell in the n-dimensional data cube; and instructions for processing the scans.

In some embodiments, a single scan in the plurality of scans is assigned to a cell in the n-dimensional data cube. In some embodiments more than one scan in the plurality of scans is assigned to a cell in the n-dimensional data cube. In some embodiments, the one or more biological experiments comprise microarray experiments or two-dimensional gel experiments. In some embodiments, the n-dimensional data cube is a two-dimensional data cube or a three-dimensional data cube. In some embodiments, the plurality of experimental factors comprises between four and ten experimental factors or more than ten experimental factors.

In some embodiments, each experimental factor in the plurality of experimental factors represents time, compound type, compound dosage, tissue type, or species in the one or more biological experiments. In some embodiments, an experimental factor in the plurality of experimental factors is a trend factor or a baseline for a ratio or a re-ratio experiment. In some embodiments, the instructions for processing the scans comprise instructions for correcting errors in the one or more scans. In some embodiments, the instructions for processing the scans comprise instructions for normalizing intensity measurements in each scan in the plurality of scans. In some embodiments, the instructions for processing the scans comprise, for each scan in the plurality of scans, instructions for storing, as a profile in the data structure, scan data that has been error corrected and normalized, wherein there is a one to one correspondence between each scan and each profile. In some embodiments, a profile is stored in the cell in the n-dimensional data cube in which the scan corresponding to the profile is stored. In some embodiments, the data structure further comprises instructions for specifying a ratio between a first set of profiles and a second set of profiles, wherein each profile in the first set of profiles and each profile in the second set of profiles corresponds to a scan in the plurality of scans. In some embodiments, the data structure further comprises instructions for combining a plurality of profiles, wherein each profile in the plurality of profiles corresponds to a scan in the plurality of scans and wherein each scan that corresponds to a profile in the plurality of profiles is a replicate. In some embodiments, the data structure further comprises instructions for analyzing the plurality of profiles, where each profile in the plurality of profiles corresponds to a scan in the plurality of scans. In some embodiments, the data structure is stored in a relational database. In some embodiments, the relational database is an ORACLE9I database.

In some embodiments, a scan in the plurality of scans has between 10 and 100 intensity measurements in a spatial array, between 100 and 500 intensity measurements in a spatial array, between 500 and 1000 intensity measurements in a spatial array, between 1000 and 5000 intensity measurements in a spatial array, between 5000 and 10000 intensity measurements in a spatial array, more than 100 intensity measurements in a spatial array, or less than 10000 intensity measurements in a spatial array.

In some embodiments, a scan in the plurality of scans represents levels of a plurality of cellular constituents in a biological sample that are measured during the one or more biological experiments. In some embodiments, each cellular constituent in the plurality of cellular constituents is a gene, a protein, an mRNA, a cDNA, a cRNA, or a degree of protein modification.

In some embodiments, the instructions for normalizing intensity measurements in each scan in the plurality of scans comprises a Z-score of intensity protocol, a median intensity normalization protocol, a log median intensity protocol, a Z-score standard deviation log of intensity protocol, a Z-score mean absolute deviation of log intensity protocol, a user normalization gene set protocol, or a ratio median intensity correction protocol.

In some embodiments, a scan in the plurality of scans represents data from a microarray or a two-dimensional gel. In some embodiments, a scan in the plurality of scans represents data from a microarray having probes arranged with a density of 100 non-identical probes per 1 $cm^2$ or higher. In some embodiments, a scan in the plurality of scans represents data from a microarray having probes arranged with a density of at least 2,500 different probes per 1 $cm^2$. In some embodiments, a scan in the plurality of scans represents data from a microarray having at least 20,000 probes.

In some embodiments, the instructions for analyzing the plurality of profiles comprise instructions for applying a classification scheme to intensity measurements in the plurality of profiles. In some embodiments, the classification scheme is a supervised classification scheme, such as linear discriminant analysis or linear regression. In some embodiments, the supervised classification scheme is multiple linear regression, partial least squares regression, principal component analysis or principle component regression.

In some embodiments, the classification scheme is an unsupervised classification scheme. In some embodiments, the-unsupervised classification scheme is hierarchical cluster analysis, non-hierarchical cluster analysis, a neural network, a self-organizing map, k-means clustering, or Jarvis-Patrick clustering. In some embodiments, the unsupervised classification scheme is a hierarchical cluster analysis. In some embodiments, the hierarchical cluster analysis is agglomerative clustering, clustering with Pearson correlation coefficients, or divisive clustering. In some embodiments, the agglomerative clustering uses a nearest neighbor algorithm, a farthest-neighbor algorithm, an average linkage algorithm, a centroid algorithm, or a sum of squares algorithm. In some embodiments, the instructions for analyzing the plurality of profiles comprise instructions for applying a parametric statistical test. In some embodiments, the parametric statistical test comprises fractional factorial design, analysis of variance, a t-test, least squares, a Pearson correlation, simple linear regression, nonlinear regression, multiple linear regression, or multiple nonlinear regression. In some embodiments, the parametric statistical test comprises one-way analysis of variance, two-way analysis of variance, or repeated measures analysis of variance. In some embodiments, the instructions for analyzing the plurality of profiles comprise instructions for applying a nonparametric statistical test. In some embodiments, the nonparametric statistical test comprises a Wilcoxon signed-rank test, a Mann-Whitney test, a Kruskal-Wallis test, a Friedman test, a Spearman ranked order correlation coefficient, a Kendall Tau analysis, or a nonparametric regression test.

4. BRIEF DESCRIPTION OF THE DRAWINGS

FIGS. 1A, 1B and 1C illustrate interaction graphs. For FIG. 1A there is no effect of either drug or time. FIGS. 1B and 1C illustrate interaction graphs where there is a main effect only for time, or only for drugs, respectively.

FIGS. 2A and 2B illustrate two cases for two different types of interaction between the experimental factors drug and time.

Figure 7A:
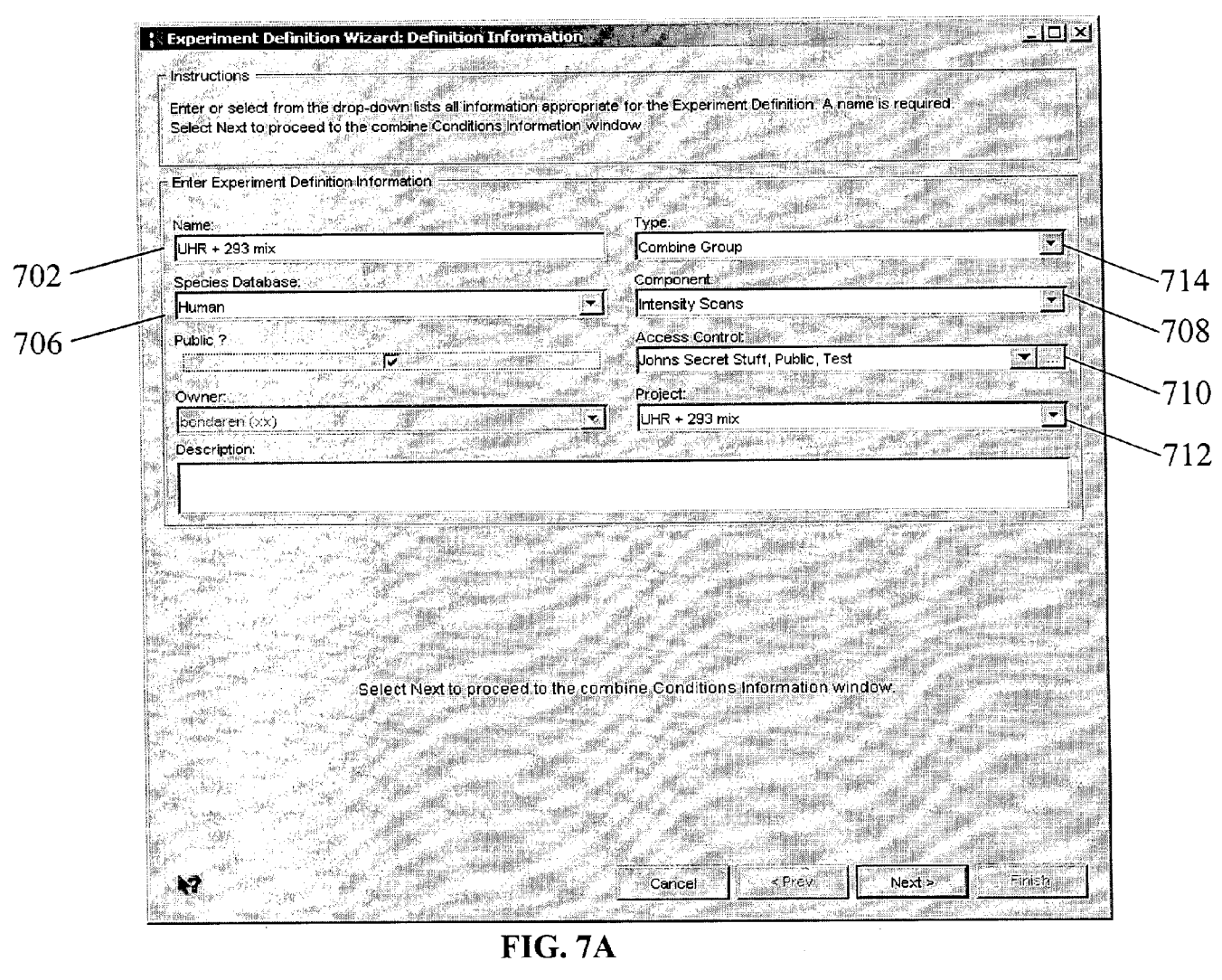
Figure 7B:
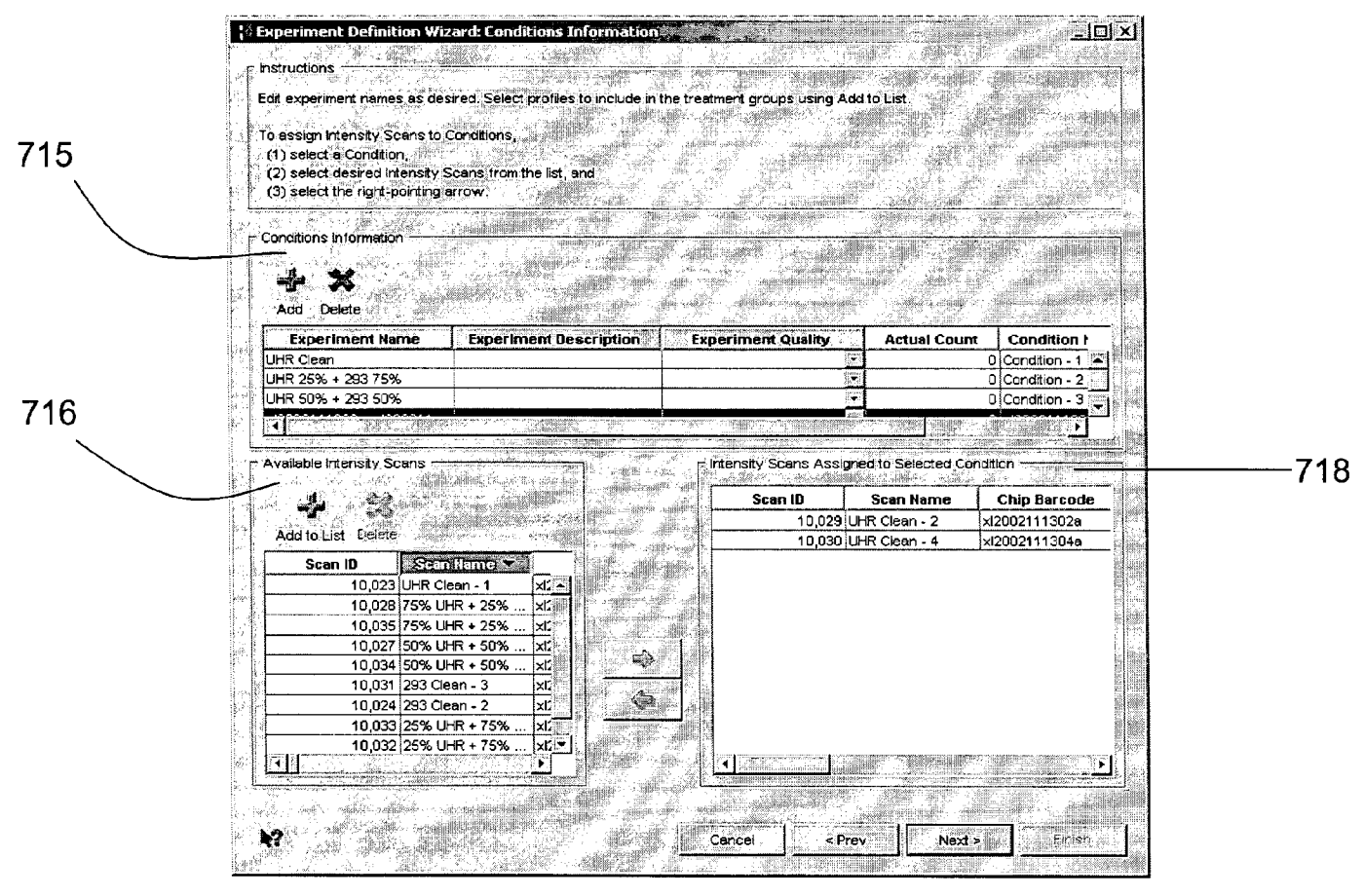
Figure 7C:
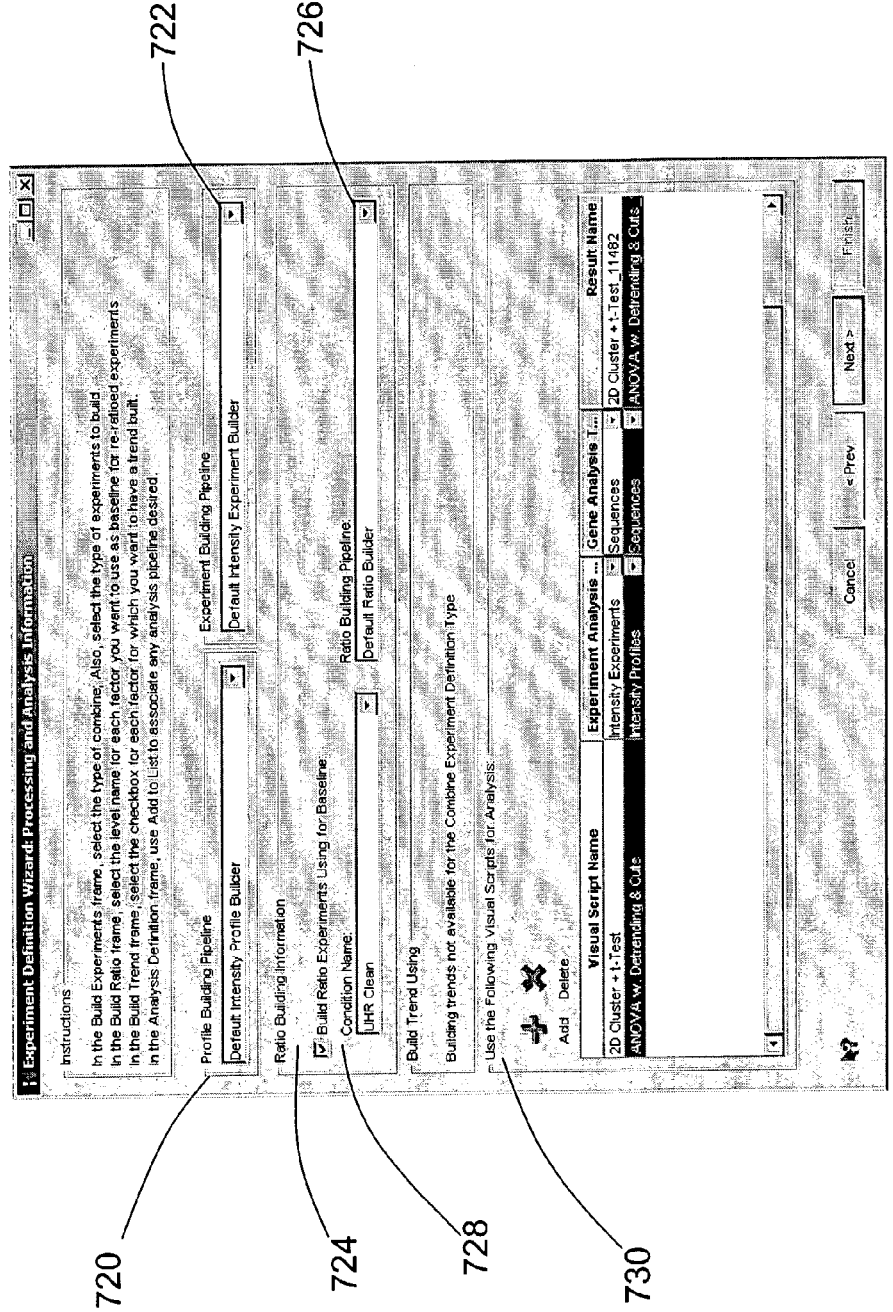
Figure 7E:
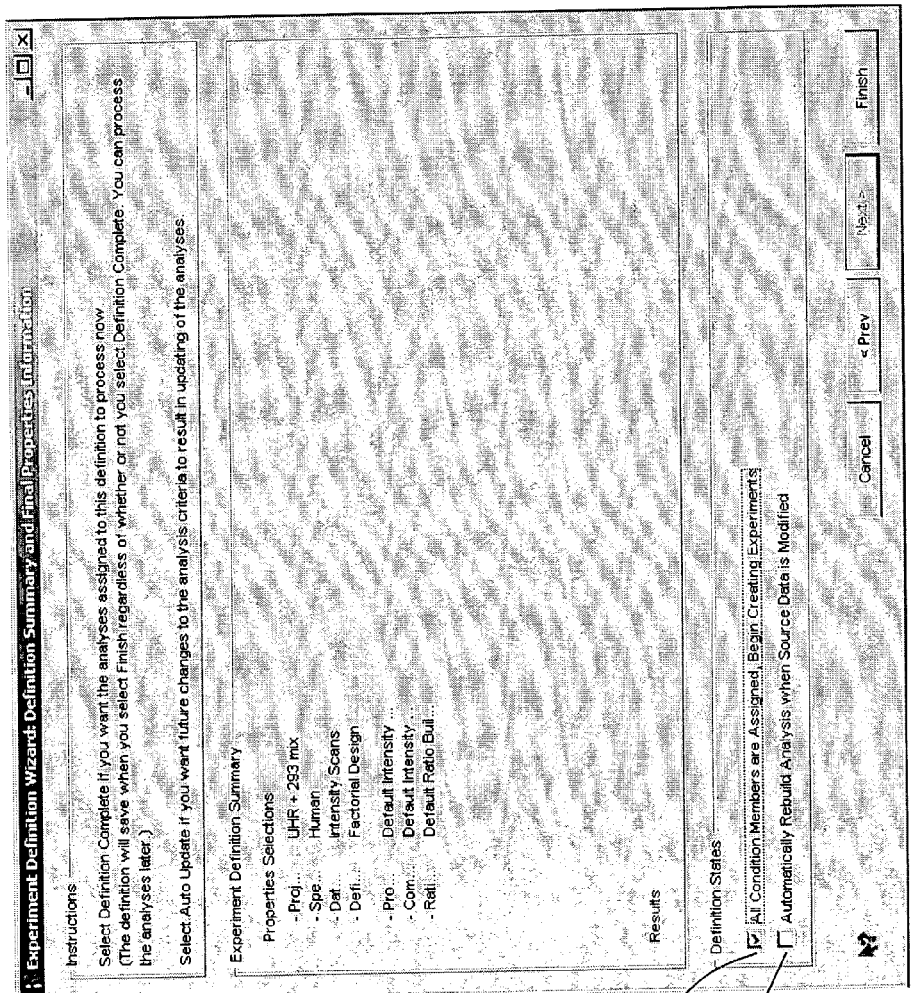

FIGS. 7A-E show screen shots of an experiment definition set up module. FIGS. 7A, 7B and 7C are presented with a choice of a combine group experiment definition, while FIGS. 7D and 7E are presented with a choice of either a combine group or a factorial experiment definition.

FIGS. 8A-D show screen shots of the experiment definition set up module.

Figure 9A:
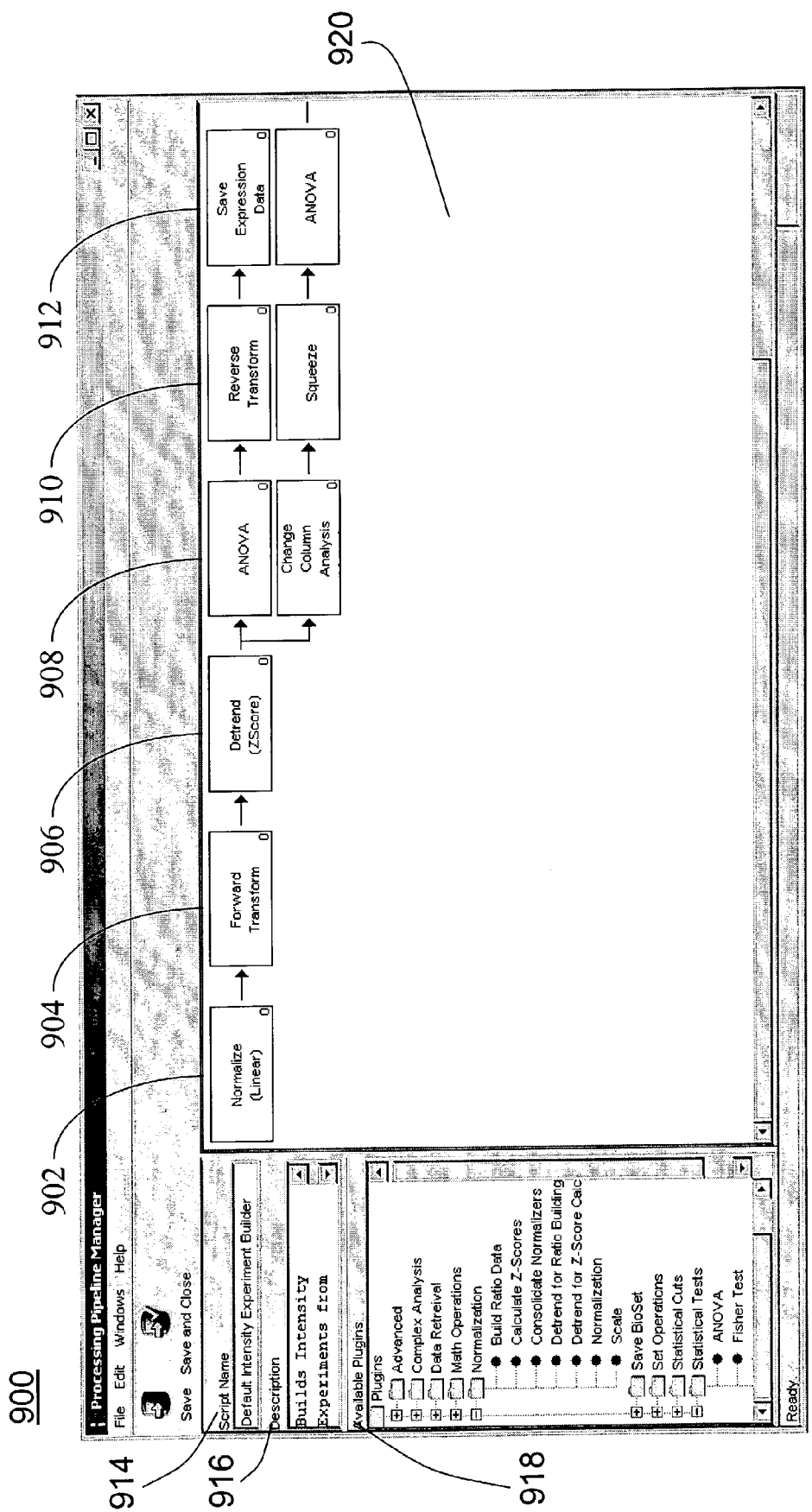
Figure 9B:
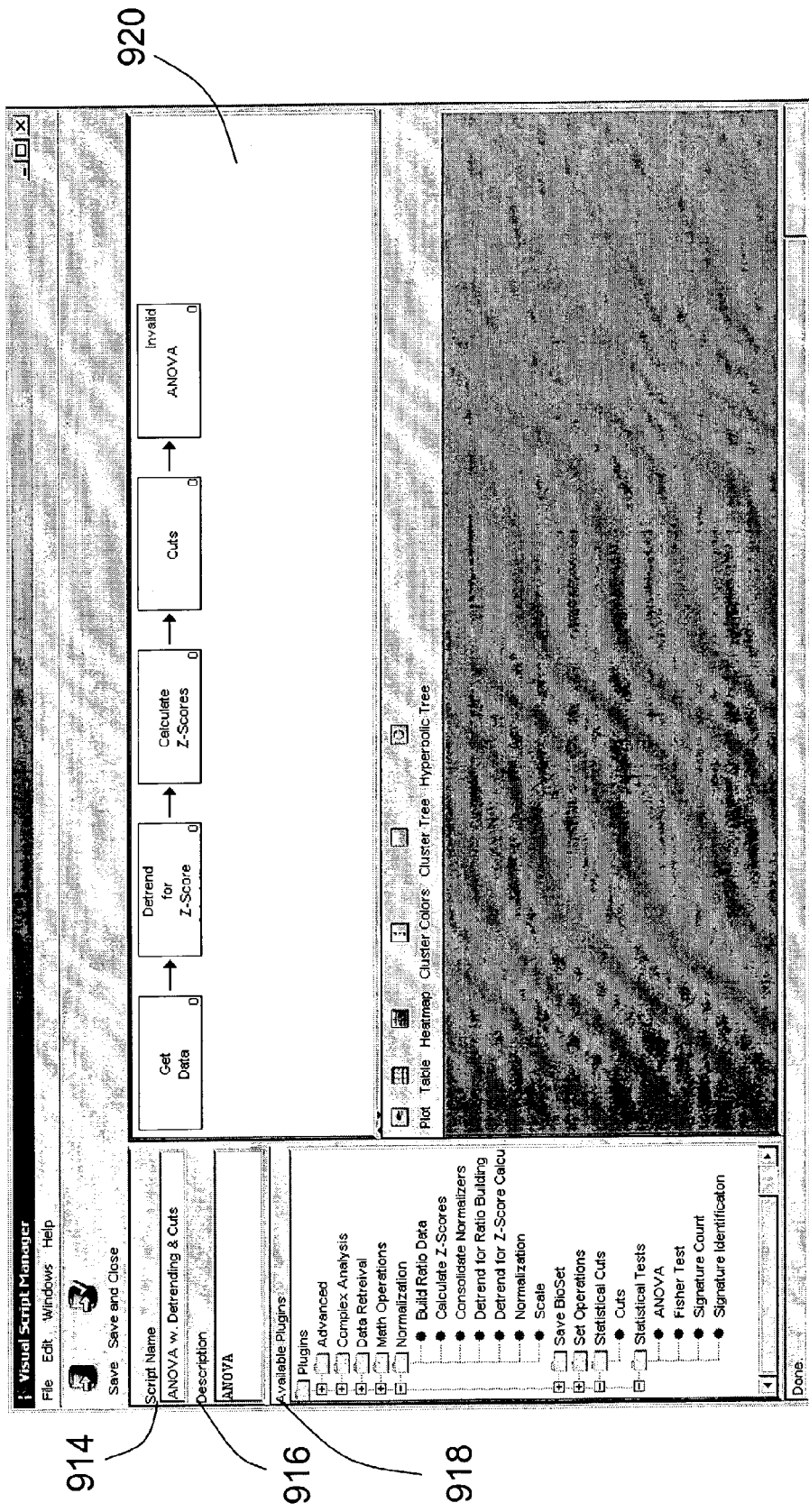
Figure 9C:
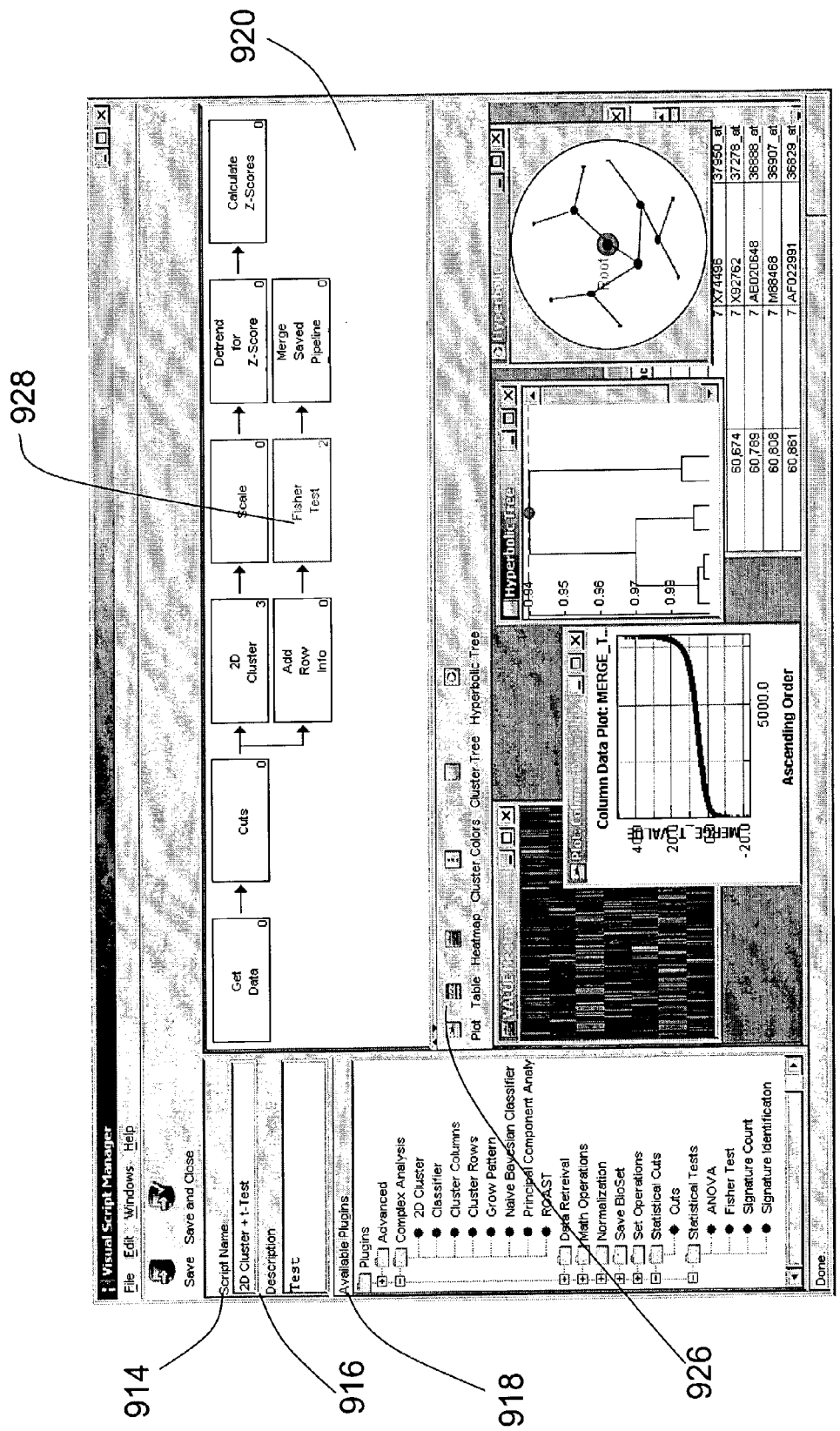

FIG. 9A-C shows screen shots of a visual scripting wizard for constructing an experiment builder pipeline (FIG. 9A), and two different data analysis types, namely ANOVA analysis (FIG. 9B), and clustering (FIG. 9C).

Figure 10:
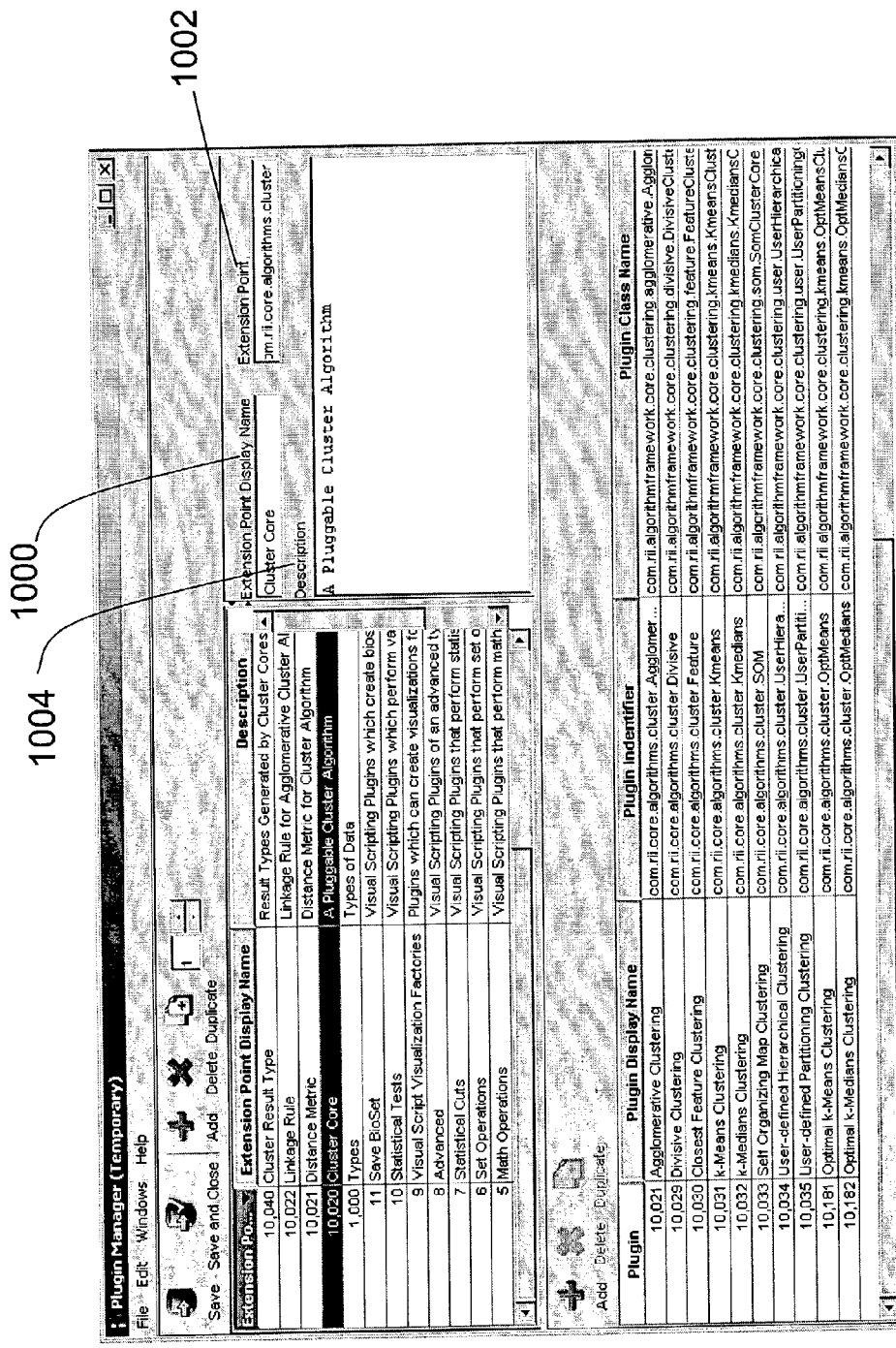

FIG. 10 shows a screen shot of a Plug-in Manager in accordance with the present invention.

Figure 11:
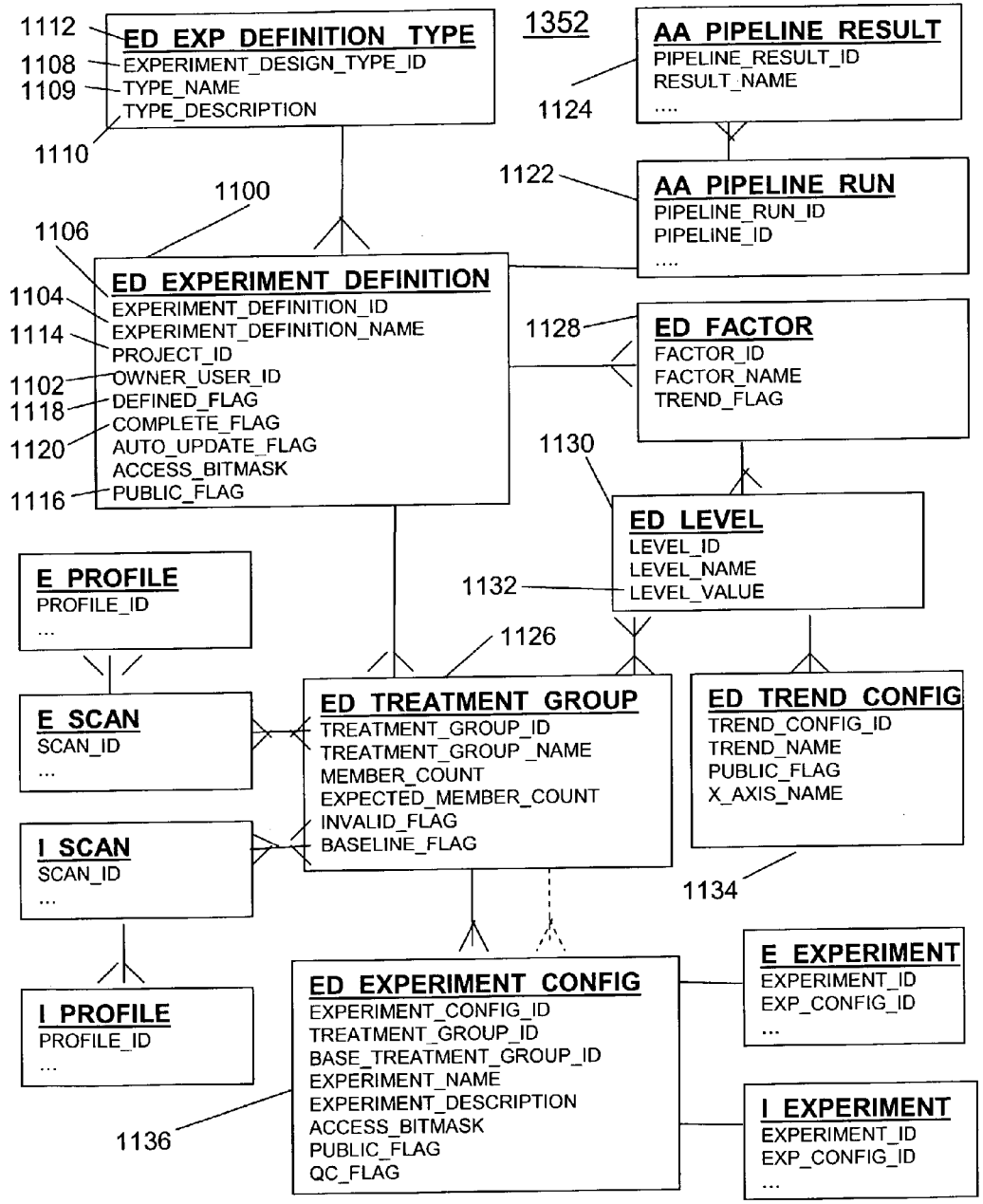

FIG. 11 illustrates an experiment definition database schema in accordance with an embodiment of the invention.

Figure 12:
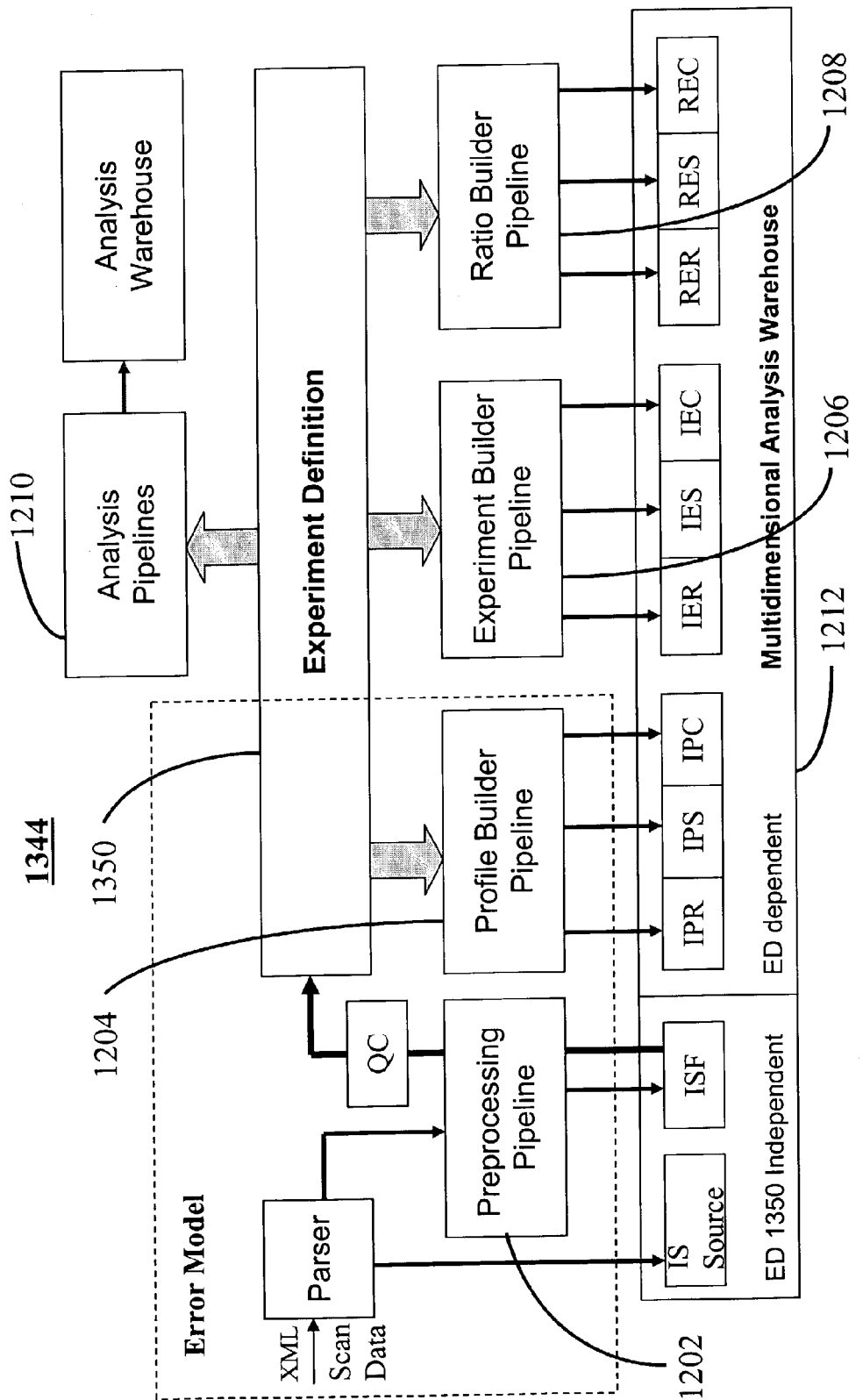
Figure 13:
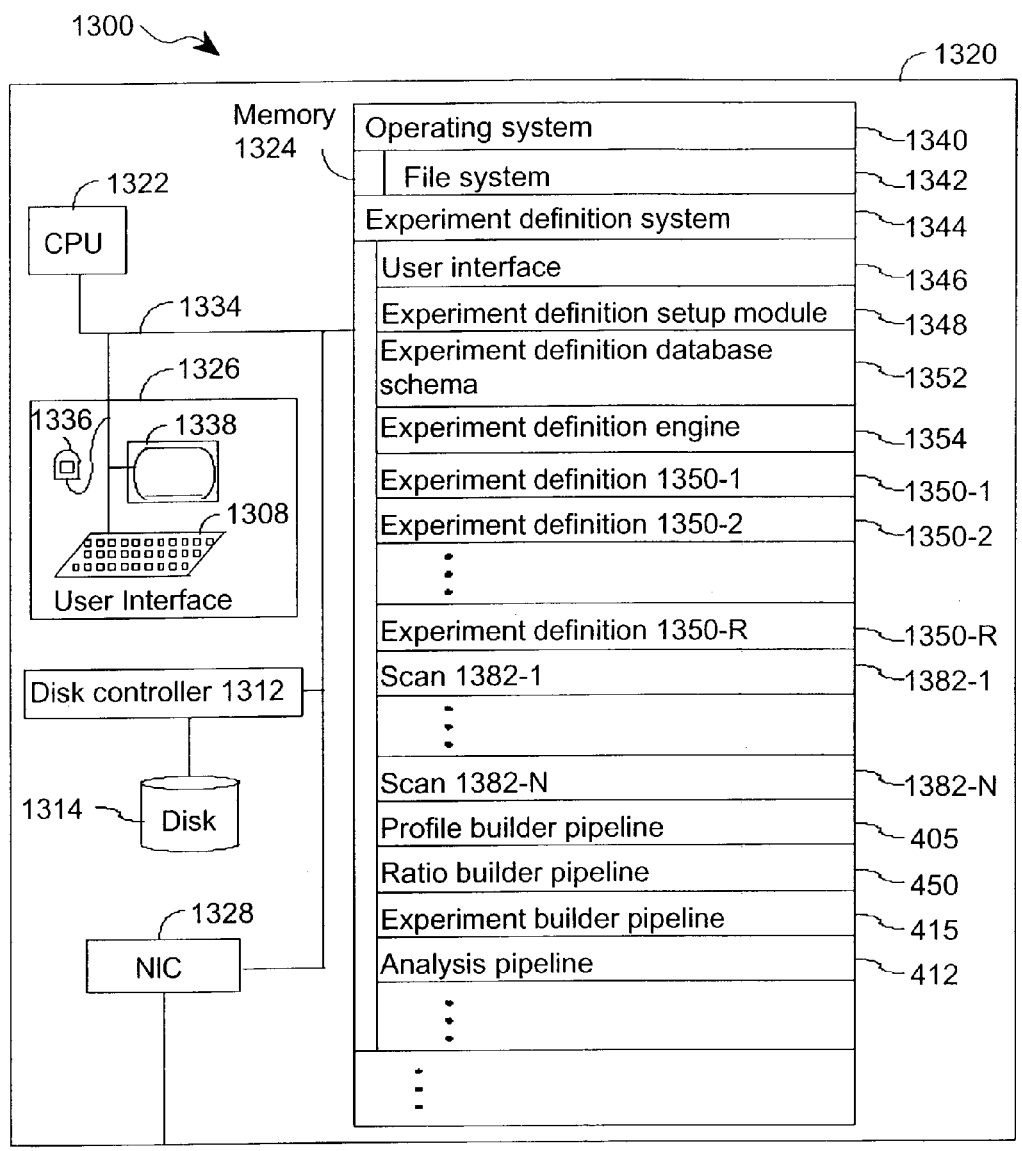

FIG. 12 illustrates the data loading framework of the experiment definition system FIG. 13 illustrates an embodiment of a computer system useful for implementing the methods of the invention.

FIG. 14 illustrates an experiment definition in accordance with one embodiment of the invention.

Figure 15:
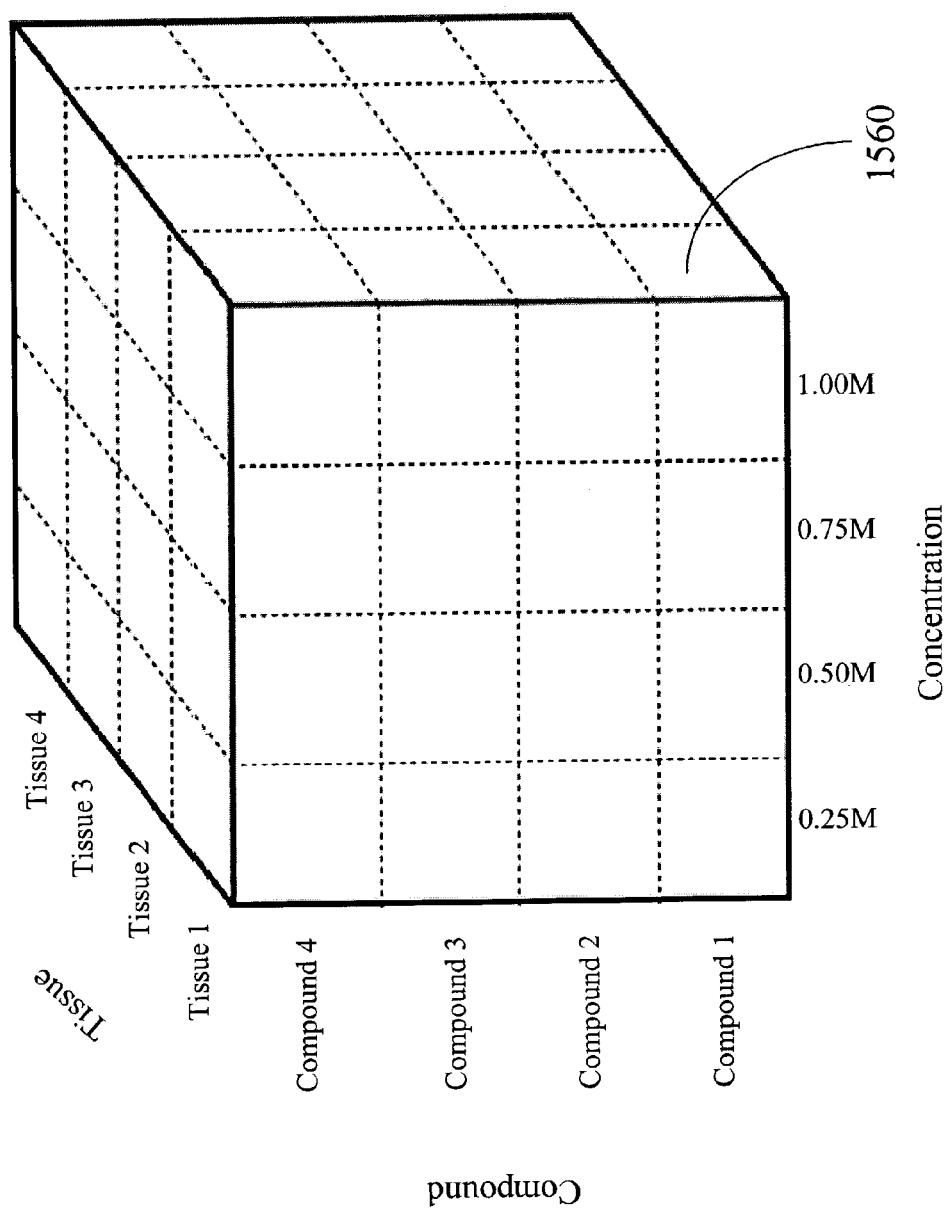

FIG. 15 illustrates a three-dimensional datacube in accordance with one embodiment of the invention.

Like reference numerals refer to corresponding parts throughout the several views of the drawings.

5. DESCRIPTION OF THE INVENTION

The present invention provides an experiment definition system for use as a data manipulation and analysis tool. The present invention allows scientists and engineers to subject their experimental design to automated data analysis. As a result, they can automatically formulate answers to research questions. The experiment definition system comprises a set of tools for automating data analysis and enforcing data consistency. The experiment definition system also provides database storage for experiment definitions. The experiment definition system further provides a user interface for creating or modifying experiment definitions, viewing data analysis results, and monitoring experiment progress.

FIG. 13 shows a system 1300 that facilitates exploratory analysis and processing of biological data in accordance with one embodiment of the present invention. Many different types of data can be processed using system 1300 including, but not limited to, microarray data and two-dimensional gel data.

System 1300 preferably comprises a computer 1320 that includes:

- a central processing unit 1322;
- a main non-volatile storage unit 1314, preferably including one or more hard disk drives, for storing software and data, the storage unit 1314 typically controlled by disk controller 1312;
- a system memory 1324, preferably high speed random-access memory (RAM), for storing system control programs, data, and application programs, including programs and data loaded from non-volatile storage unit 1314; system memory 1324 may also include read-only memory (ROM);

a user interface 1326, including one or more input devices, such as a mouse 1336, a keypad 1308, and a display 1338;

an optional network interface card 1328 for connecting to any wired or wireless communication network; and an internal bus 1334 for interconnecting the aforementioned elements of the system.

Operation of computer 1320 is controlled primarily by operating system 1340, which is executed by central processing unit 1322. Operating system 1340 can be stored in system memory 1324. In some embodiments, operating system 1340 includes a file system 1342. In addition to operating system 1340, a typical implementation of system memory 1324 includes a variety of program software modules, databases, and files that are regulated by experiment definition system 1344.

Experiment definition system 1344 comprises:

a user interface 1346 that provides access to experiment definition system 1344 that is described in more detail in Section 5.3.1, below;

an experiment definition setup module 1348, which is described in more detail in Section 5.3.2 below, for creating experiment definitions 1350;

an experiment definition database schema 1352 that provides the database schema used to store each experiment definition 1352, which is described in further detail in Section 5.3.3, below; and an experiment definition engine 1354 for ensuring consistency of experiment design and expression data and analysis results, which is described in further detail in Section 5.3.4, below.

Experiment definition system 1344 further comprises one or more experiment definitions 1350 that are designed to process scans 1382 in order to answer biological questions, import scans 1382 into system 1320, or export scans 1382 from system 1320. Experiment definition system 1344 also comprises one or more scans 1382. For ease of illustration, scans 1382 are illustrated in memory 1324. However, those of skill in the art will appreciate that all or a portion of scans 1382, as with any data structure or program module illustrated in memory 1324 of FIG. 13, can in fact reside in storage device 1314 or on any computer that is addressable by system 1300.

In general, data considered by experiment definition system 1344 is in the form of scans 1382. A scan 1382 is a dataset that represents a scanned image. The image consists of intensity spots in a spatial array. Typically, the image is a microarray experiment. However, the image can be generated from any form of biological experiment that involves a biological measurement technique that generates intensity data in a spatial array format (e.g., two-dimensional gels). The intensity data can represent, for example, levels of cellular constituents in a biological sample. Experiment definition system 1344 processes each scan 1382 by applying error correction techniques that are specified by an experiment definition 1350. In various embodiments, there are between 10 and 100, between 100 and 500, between 500 and 1000, between 1000 and 2000, between 2000 and 3000, between 3000 and 5000, between 1000 and 5000, between 5000 and 10000, between 5000 and 50000, more than 100, or less than 10000 intensity measurements in a scan 1382. These intensity measurements are arranged in a spatial array. In other words, each intensity measurement is addressable in a coordinate system, such as a Cartesian coordinate system. In some embodiments each of these intensity measurements corresponds to a level of a cellular constituent in a biological sample, as described herein.

A processed scan 1382 is referred to as a profile 1380. In other words, a profile 1380 is a normalized scan. To generate a profile 1380 from a scan 1382, errors (e.g., systematic errors) in the scan 1382 are corrected by applying the error model specified by the controlling experiment definition 1350 as will be described in more detail below.

The types of error corrected by an error model comprise systematic error and random errors. One form of systematic error arises in instances where the scanner used to digitize the raw image is not entirely uniform. Thus, the scanner can make systematic errors in intensity values in scans 1382. In one hypothetical example, a scanner consistently downweights intensity values in a particular quadrant of each scan 1382. This represents a systematic error. To identify and correct for such systematic error, the error model specified by the controlling experiment definition 1350 is trained against reference images that have been scanned by the scanner. Then, the trained error model is used to adjust for systematic errors as scans are processed into profiles in accordance with the experiment definition 1350.

In addition to correcting for systematic errors, error models can be used to correct random errors. Random errors can be corrected using many different types of techniques. For example, a given scan 1380 can include multiple reporters for the same cellular constituent (e.g., gene, protein, metabolite, etc.). These reporters can be statistically combined (e.g., by a weighted averaging) to create a more accurate measurement of the cellular constituent.

In addition to the modules and data structures described above, experiment definition system 1344 includes the following pipelines (FIGS. 4 and 13):

a profile builder pipeline 405 for processing (e.g., intensity normalization, detrending and error model application) scans 1382 into profiles 1380 in the manner specified by a controlling experiment definition 1350;

a ratio builder pipeline 450 for taking the ratio of experimental factors or levels in a specified groups of profiles 1380 in the manner specified by a controlling experiment definition 1350;

an experiment builder pipeline 415 for combining replicates (profiles of scans that were obtained under the same conditions) in accordance with a controlling experiment definition 1350; and an analysis pipeline 412 ("visual script") for analyzing (e.g., ANOVA, clustering, application of classifiers, pattern discovery) processed scans in accordance with an experiment definition 1350.

Figure 4:
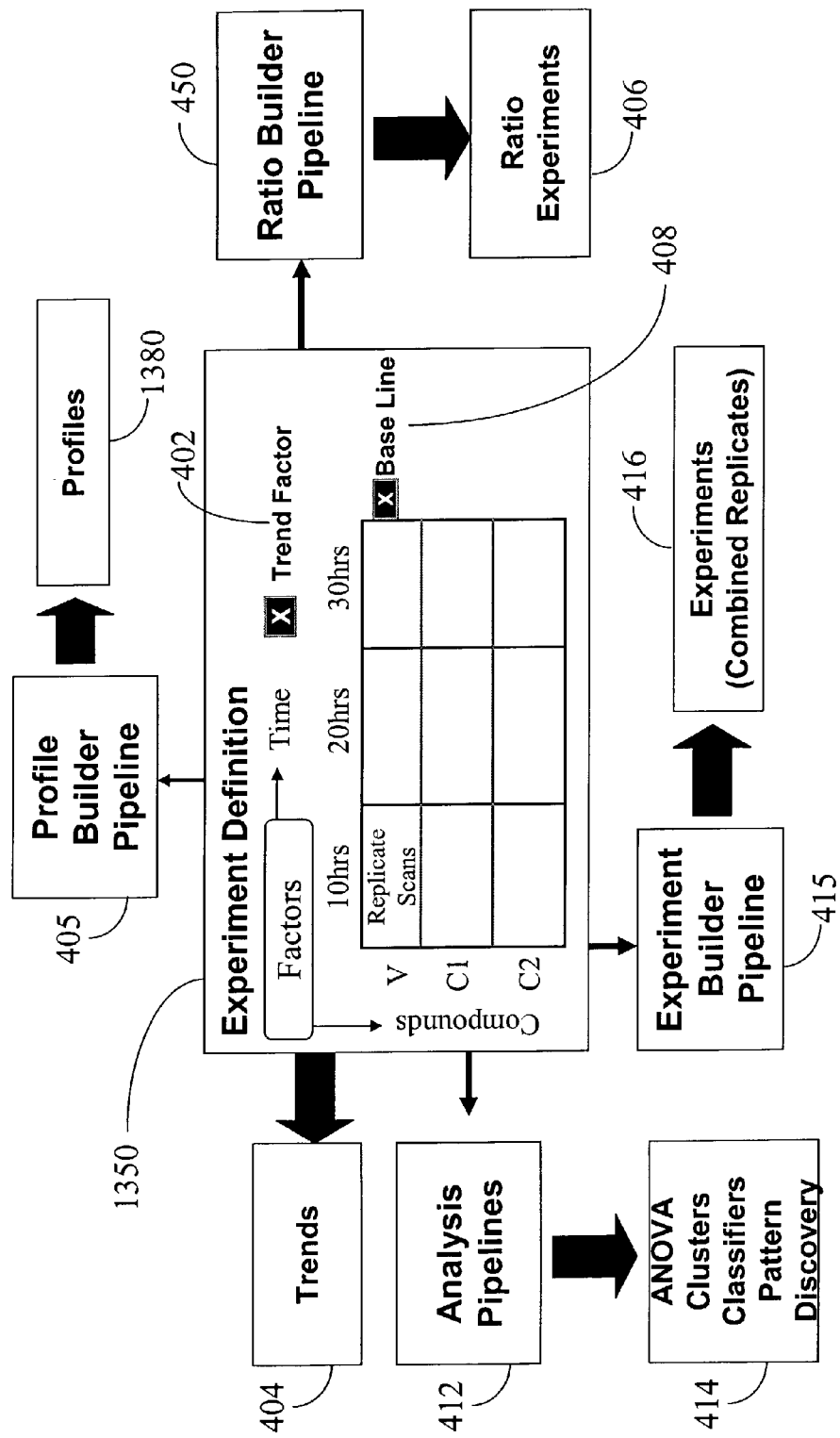
FIG. 4 illustrates an experiment definition that corresponds to the factorial design experiment of FIG. 3, as well as the automated pipelines of the experiment definition system.

Each experiment definition 1350 can include a description or reference to a project and instructions on how to process a plurality of scans 1382. As used herein, a project is a collection of experiment definitions that have some common purpose. These instructions for processing scans 1382 can invoke any combination of profile builder pipeline 405, ratio builder pipeline 450, and experiment builder pipeline 415 in order to prepare a multidimensional data structure. Then, this multidimensional structure is analyzed by analysis pipeline 412. The exact nature of the analysis performed by analysis pipeline 412 is determined by instructions stored in the experiment definition 1350. Representative forms of analysis that can be performed by analysis pipeline 412 include, but are not limited to ANOVA, clustering, application of classifiers, and pattern discovery (FIG. 4).

One advantage of the present invention is that different error models can be applied to scans 1382. Thus, there can be a plurality of profiles 1380 corresponding to a single scan 1382 (or group of scans 1382), where each profile 1380 in the plurality of profiles is the result of the application of a different error model to the scan 1382 (or group of scans 1382). This advantageous application is possible through usage of novel experiment definitions 1350. In some embodiments of the present invention, an experiment definition 1350 is a data structure that contains all the information needed to process scans 1382, including an error model. In a preferred embodiment, experiment definitions 1350 are stored in a database so that they can be accessed by multiple users. In some embodiments this database is a relational database. For example, in some embodiments this database is an Oracle9i database (Oracle, Redwood Shores, Calif.). Thus, different people can process the same scans 1380 and thereby derive different profiles 1380. This is advantageous when different people are attempting to address different biological questions using the same raw data.

The novel experiment definitions 1350 of the present invention allow researchers more control over how biological data is processed. Each experiment definition 1350 is capable of specifying every aspect of biological data analysis, including which error model is used to process scans, which scans are to be used in a statistical analysis, and how the statistical analysis is applied to the scans. In the present invention, experimental definitions 1350 can be shared with other users or designated as private. In other words, access privileges can be assigned to experimental definitions 1350 to ensure experimental analysis integrity in a shared environment.

The novel experiment definitions 1352 of the present invention allow researchers to more easily analyze data starting at a lower level (application of an error model to the raw data). One example where this capability can be used is the case in which error estimation is applied across multiple scans 1382. Using the present invention, such error estimation techniques are more easily implemented when scans 1382 are similar to each other or are replicates. The term replicate refers to scans that are taken under the same conditions (e.g., same compound exposure, same time course, etc.). The experiment definitions 1350 of the present invention can be used to designate specific scans 1382 in a database of scans as replicates. Then, more advanced error models that exploit advanced multiple scan statistical error correction techniques (e.g, normalization, detrending) can be designated in an experimental definition 1350. The experimental definition 1350 can then be used to process and analyze the replicates. Thus, when replicates are incorporated into a particular experiment definition 1350, the scans 1382 can be reprocessed all the way from the raw image in a manner that is consistent with the specific biological question under study, thereby reducing errors in the analysis.

Experimental definitions 1350 provide a convenient way to control how data is processed. For example, if advanced multiscan error correction techniques are applied at a low level, then more crude higher level error correction techniques that are designed to simulate such error correction techniques can be skipped. All this can be easily specified in the experimental definition 1350.

Those of skill in the art will appreciate the many advantages of the present invention. Two researchers working in a shared environment can study the same scans 1382 using completely different assumptions that require application of completely different error models. To accomplish this, each researcher customizes their own experiment definition 1350. No conflict arises, even in the case where the researches are using the same scans 1382. Further, a researcher seeking to address a biological question can specify an experiment definition 1350 that is consistent with the biological question down to the level of how raw data is processed by simply modifying an experiment definition 1350.

Some embodiments of the present invention allow for the modification of experimental definitions 1350 using wizards and other forms of graphical user interface techniques as will be described in more detail in the following sections and the Figures.

5.1. Experimental Design

Many measurement experiments use experimental design, a formal plan that details the specifics for conducting an experiment to answer experimental questions about a particular system. The experiment design provides the structure for the research. In other words, it provides the framework that holds the various elements in a research project together, such elements including bio-samples, microarrays, measurements, groups, and assignment to a group. As used herein, an experiment design refers to a structured research project that is geared towards providing answers to research questions.

As used herein, a scan 1382 refers to one or more measurements for a specific bio-sample, such as a scanned image from a microarray, a scanned image of a two dimensional-gel, or mass spectrometry data, such as liquid chromatography/mass spectrometry (LC/MS), matrix-assisted laser desorption/ionization-time of flight mass spectrometry (MALDI-TOF MS), etc. Types of experimental systems and samples amenable to the present invention include cholesterol level in the blood, DNA level measurements, two-dimensional protein gels, microarrays of expression data (whether single color or two-color labeling), and molecular profiling. During the performance of an experiment design, an experimenter can collect any number of scans 1382. Exemplary techniques for collecting such data are discussed in Section 5.9 below. Depending on the complexity of the experiment design, the experimenter can collect any number of scans, e.g., between 1 and 3 scans, up to 10 scans, up to 40 scans, up to 100 scans, more than 100 scans or less than 100 scans. The number of scans depends on parameters such as the number of experimental factors and the number of levels per experimental factor used in a subsequent analysis, the number of replicates, etc. An experiment refers to combined replicates, which can be formed, e.g., by applying a weighted error model to combine scans 1382.

A profile 1380 refers to a normalized scan 1382, that results from application of an error model. Multiple profiles 1380 can be built from the same scan 1382 as a result of using different error models, e.g., by using different experiment definitions.

There are many different variations of experimental designs, including two-group design, covariance design, factorial design, randomized-block design, etc. An example of an experiment design is a simple design. In the performance of a simple design, a baseline level for each experimental factor is chosen, and the performance of the subject under the baseline level of all of the experimental factors is measured. The level of the first experimental factor is then varied, and the performance of the subject is measured at the new level. For example, the first level of the experimental factor is one particular drug administered to cells at a minimal dosage level to determine its effect on inhibiting the binding of a target to the cell. The concentration of the drug is then increased to measure that effect on inhibiting binding of the target. The experiment is repeated any number of times at the drug dosage levels desired by the experimenter. The next experimental factor could be another type of drug, which is also administered at a number of different dosage levels. For a total number of experimental factors k, with $n_i$ levels for the $i_{th}$ factor, the total number of independent experiments that are performed is given by the expression:

$$1 + {}^k\Sigma_{i=1}(n_i - 1)$$

The value 1 accounts for the baseline, while the summation accounts for one experiment being performed for each factor at all levels other than baseline. The disadvantage of a simple design is that, since each experiment is performed by varying one experimental factor at a time, it could give false conclusions about factor interactions. An alternate design could give more information about interactions using a similar number of experiments.

One goal of experimental design is to improve the quality of research by increasing the signal-to-noise ratio. This can be accomplished by either working to increase the signal in a measurement or to reduce the noise, such as that from non-specific binding on a microarray. Accordingly, an experiment design is generally classified into the two categories, namely signal enhancing experimental designs and noise reducing experiment designs. A signal-enhancing experimental design is the factorial design, which is described in greater detail in Section 5.1.1, infra. Two types of noise-reducing experimental designs are covariance designs and randomized-blocking designs, where, e.g., information about the sample is used to remove some of the noise in the measurement. Different statistical analysis methods, such as ANOVA, can be applied to the responses measured using the various different experimental designs to determine, e.g., if there is a statistically significant difference between the average of the value of the responses measured at two different levels, etc. An example of a one-way ANOVA combine group experiment design is testing the variance of sequences among groups, such as five replicates of a drug level in five animals. The results of the one-way ANOVA combine group experiment design indicate the most differentially expressed among the groups.

5.1.1. Factorial Design

Factorial design refers to a matrix arrangement of multiple levels and experimental factors of an experiment. A typical factorial design examines a number of different variations of a treatment. Examples of experimental factors to serves as the major independent variable in factorial design, include, time, dosage, compound, etc. As used herein, the terms "factor" and "experimental factor" are used interchangeably. Two types of factorial design are the full factorial design and the fractional factorial design.

In the full factorial design, the experimenter exhaustively tries every possible combination of all levels of all factors. In this case, for a total number of factors k, with $n_i$ levels for the $i_{th}$ factor, the total number of experiments performed is:

$$^k\pi_{i=1}(n_i) = (n_1)(n_2)(n_3) \ldots (n_k)$$

For example, to monitor the effect of drug 1, administered at three different dosage levels, and drug 2, administered at four different dosage levels, requires a minimum of 12 experiments.

Figure 3:
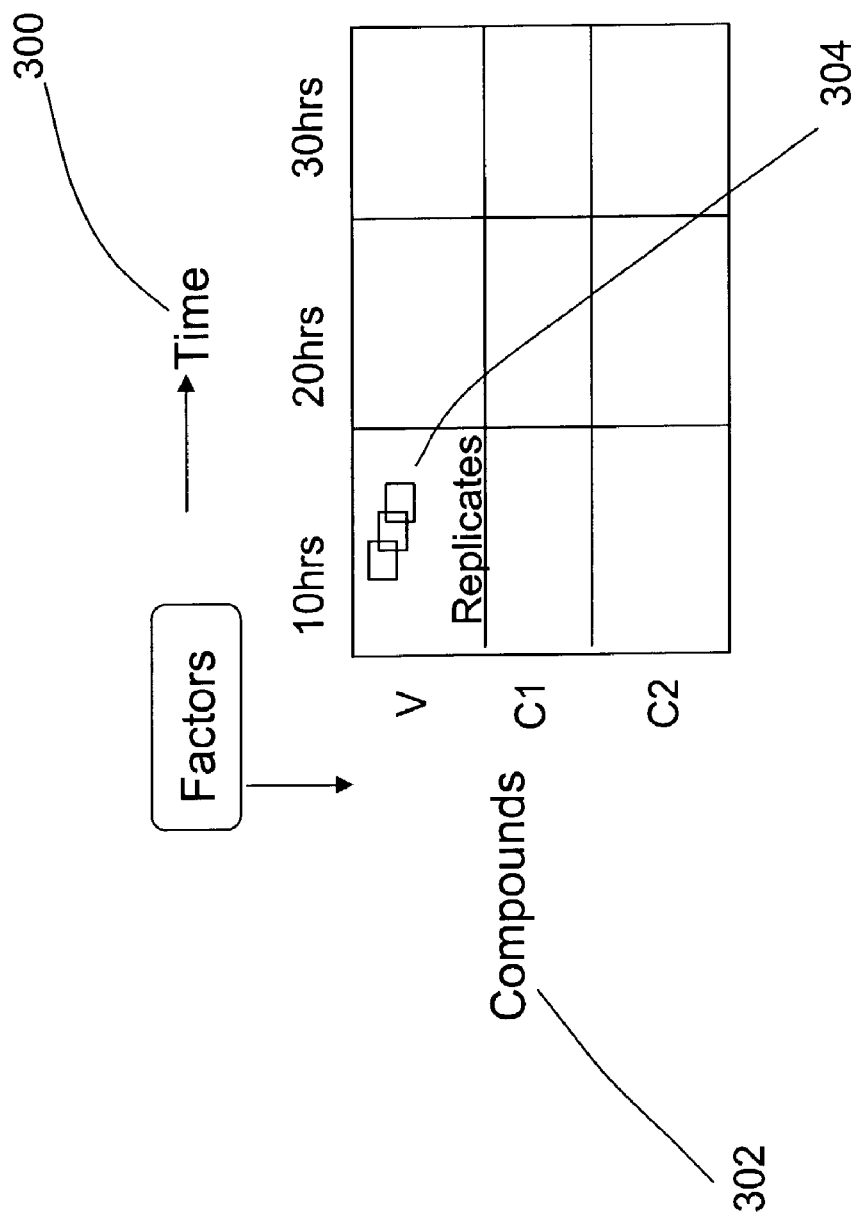
FIG. 3 illustrates a two-dimensional factorial design experiment, where the experimental factor time has three levels of 10, 20 and 30 hours, and the experimental factor of compounds have three levels of vehicle (V), compounds C1 and C2.

FIG. 3 illustrates a 3×3 two-dimensional factorial design for the two factors of treatment time and compound using a matrix. In the illustration, the experimental factor time 300 has the three levels, 10 hours, 20 hours, and 30 hours, while the experimental factor compound 302 has the three levels: V, C1, and C2 (where V indicates vehicle and C indicates compound). A two-dimensional factorial design for ANOVA is commonly referred to as a two-way ANOVA. The intersection of the levels of the two experimental factors is called a treatment group, such as 10 hours in the presence of the vehicle. A given treatment group comprises the statistical replicates 304 of the treatment, e.g., the replications with the vehicle at 10 hours. A treatment group member refers to an intensity profile, a ratio profile, an intensity experiment, or a ratio experiment assigned to the treatment group.

One advantage of a full factorial design is that the main effect of every factor can be found, including any secondary factors, as well as any interaction effects operative between the factors. One disadvantage of a full factorial study is that the number of experiments can become quite large for a large number of factors and/or levels.

One way to reduce the number of experiments performed in a full factorial design is to reduce the number of levels for each factor. An extreme case might be to try just two levels for each factor, a low and a high value. A full factorial design, with only two levels for each factor, is called a $2^k$ design. Analysis of the outcome of a $2^k$ design could give useful information for structuring an experiment design with additional levels. Another way to reduce the number of experiments performed is to reduce the number of factors. If the factors could be divided into primary and secondary categories, then only factors in the primary category could be varied. Yet another way to reduce the number of experiments is to use a fractional factorial design.

A fractional factorial design use only a fraction of the full factorial design, and can be used as a screening experiment to determine which factors should be examined more closely. For example, performing only half of the experiments in a $2^k$ design gives a $2^{(k-1)}$ fractional factorial design, also called a half-replicate of a $2^k$ design. A general expression for the number of experiments performed is a $2^{(k-p)}$ design for some integer p. Initially, the number factors can be reduced by, e.g., choosing to apply only the primary factors. Next, with a priori knowledge that interactions between certain factors would be negligible, the number of experiments can be further reduced to a number $2^{(k-p)}$. In planning a fractional factorial design, it is preferable to consider the contributions of a given factor to the total variance of the results if fewer than a full factorial number of experiments are performed. While a fractional factorial design can help to reduce the time or cost of experimentation, care should be taken in choosing constructing the experiment design, as the experimenter runs the risk of overlooking a critical relationship with a poorly design.

5.2. Experiment Definition System

The present invention uses an experiment definition 1350 that digitally represents the design of an experiment. Experiment definition 1350 provides the logical structure of the way an experimenter performs data analysis in accordance with an experiment design, including combining replicates, building ratio or re-ratio experiments, and performing statistical tests like ANOVA, or t-test, creating trends, clusters, etc. An experiment design addresses a biological question. An experiment design can be complex. For example, an experiment design can include multiple compounds, multiple dosing, multiple time courses, and multiple animals. Data analysis of the measuring experiments performed in accordance with an experiment design is complex and laborious using known systems.

Experiment definition 1350 is a collection of instructions on how to process the data from measurements. As the instructions for performing the experiment design are saved, each user can create their own personal experiment definitions 1350. The invention provides an experiment definition system 1344 that structures raw data, provides a flexible digital framework for structuring the research project, and analyses of the data. Through experiment definition system 1344, the experimenter defines how the major parts of the research project, including the samples or groups, measures, treatments, and methods of statistical analysis along with the data analysis results, etc., work together to address research questions.

Figure 2A:
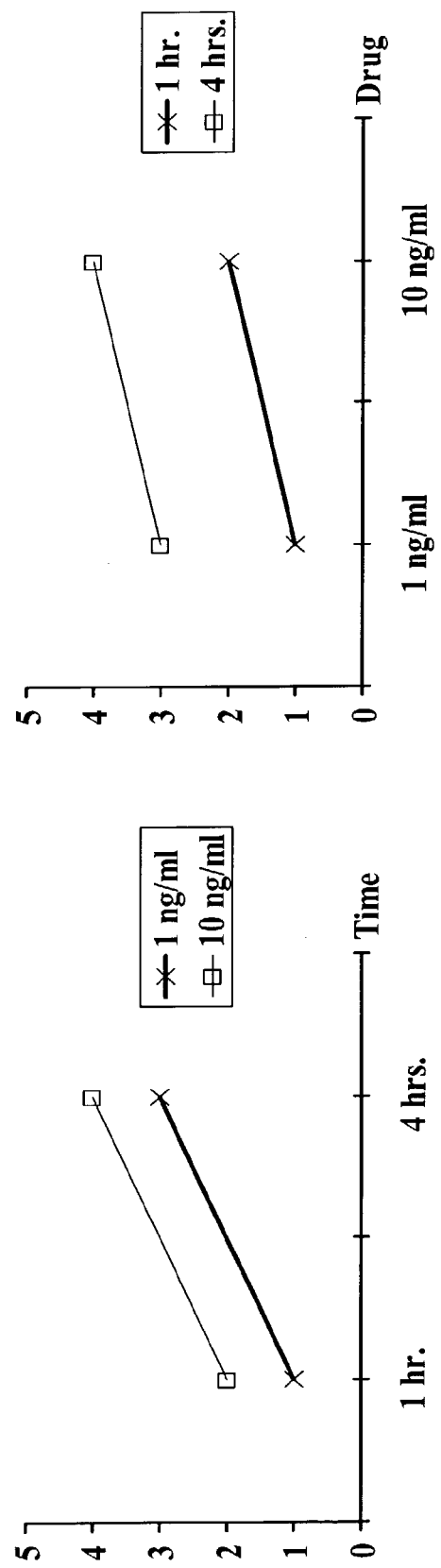
FIG. 2A illustrates an interaction graph for the case where there is a main effect for both experimental factors, but with no interaction.
Figure 2B:
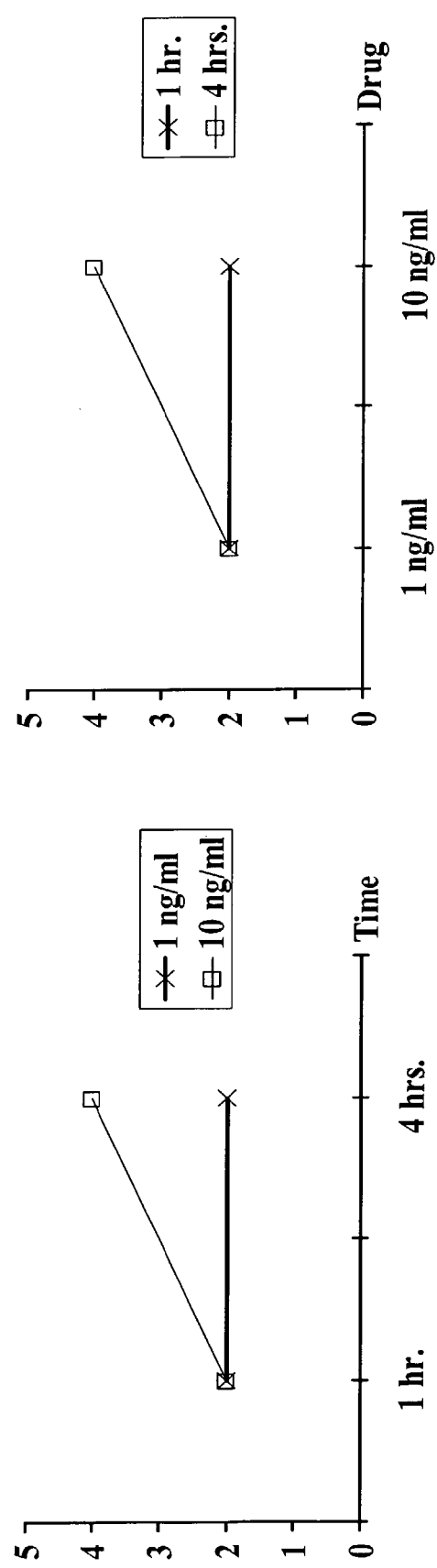
Figure 2C:
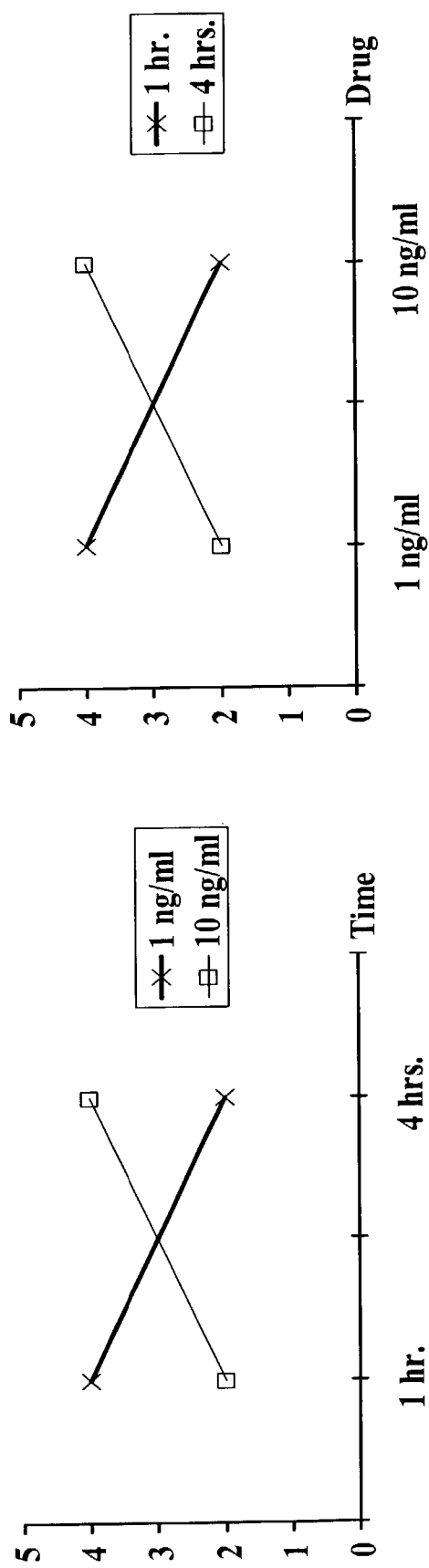

Experiment definition system 1344 automates statistical analysis by reflecting knowledge about the experiment design in an experiment definition 1350, as illustrated in FIG. 4. Experiment definition system 1344 provides for automatic combination of statistical or biological replicates, building of ratio experiments from intensity (single channel technologies) or re-ratio experiment from ratio (two or more channels technologies) using a specified base line 408, statistical test analysis like one or two way ANOVA, t-test, etc., and building of trends 404, clusters, and classifiers 414. Experiment definition 1350 also provides for the building of profiles 404 from scans 1382 using profile builder pipeline 405. FIG. 4 is an illustration of an experiment definition 1350 of the 3×3 two-dimensional factorial experiment design of FIG. 3. Experiment definition 1350, includes non-sample related information. For example, the experimenter can specify a trend factor 402 as the basis for evaluating the results of an experiment design. In FIG. 4, the trend factor is time. The use of a trend factor is illustrated in FIGS. 2A and 2B, where for example, the trend factor is time (FIG. 2A), or a drug (FIG. 2B). Experiment definition 1350 can then return results from an analysis of trends 404. For ratio and re-ratio experiments 406, the experimenter can specify a baseline 408 level of one of the factors, which is the level V (vehicle) in the illustration. The experiment definition 1350 would also include a choice of statistical test 410 employed for, e.g., analyzing the profiles.

In the embodiment illustrated in FIG. 4, the experiment design is a two-dimensional factorial design. However, the addition of one or more factors, e.g., tissue and/or dosage, to the example of FIG. 3 changes the dimensionality of the factorial design to a three-dimensional or even a four-dimensional factorial design. The complexity of a factorial design grows considerably when there are more than two factors. One constraint on factorial designs is the complexity of statistical analysis, e.g., ANOVA analysis with more than two factors. An experiment definition 1350 would need to provide ways to support factorial designs with three or more factors for factorial data analysis. In a preferred embodiment, the present invention provides an experiment definition 1350 with the capability of creating one or two way ANOVA. In embodiments where more than two factors are used in an experiment definition 1350, they can be spliced on multiple two-dimensional factorial designs. For example, if a third factor that has two different levels is added to the factorial design of FIG. 3, then the 2×3×3 three-dimensional factorial design could be represented by two different 3×3 two-dimensional factorial designs, i.e., one two-dimensional matrix corresponding to each level of the third factor.

While experiment definition system 1344 can be made to reflect the experiment design in a direct one-to-one relationship, as illustrated in FIG. 4, in other embodiments of the invention, the experiment definition 1350 is user specified. For example, an experimenter can redefine an experiment definition 1350 by, e.g., redefining one or more treatment groups, or can change the assignment of scans to a treatment group, in order to answer different scientific questions. As a result, users of the invention can create their own experiment definition 1350 or even multiple experiment definitions 1350 based on the same experiment design.

5.2.1. Capabilities of the Experiment Definition System

Experiment definition system 1344 provides increased flexibility over currently available forms of experiment representations and data analysis, such as the Rosetta Resolver® gene expression data analysis system. The experiment definition system 1344 provides the capability of storing the instructions for performing a data analysis according to an experiment definition 1350. This is particularly advantageous to the user who repeatedly performs the same type of analysis.

One embodiment of the invention provides a single Experiment Definition (ED) Wizard that prompts the user to define the experiment definition 1350 and specify the data analysis to be performed.

Experiment definition system 1344 supports any class of experiment design, including two-group design, covariance design, factorial design, and randomized-block design. These experiment designs are encoded in experiment definitions 1350. There are two types of experiment definitions 1350. They are the "factorial design" experiment definition 1350 and the "combine group" experiment definition 1350. In fact, the "combine group" experiment definition 1350 is a subset of the "factorial design" experiment definition. In other words, the "combine group" experiment definition 1350 is a simplified form of the "factorial design" experiment definition 1350 that includes less attributes and less structure than the "factorial design" experiment definition.

Experiment definitions 1350 will now be described in further detail with reference to FIGS. 14 and 15 so that the many advantages of such data structures can be further appreciated. FIG. 14 illustrates a "factorial design" experiment definition 1350. The data structure provides annotation fields such as name 1402 for naming the experiment definition. Such annotation fields are a useful way for a researcher to categorize experiment definitions 1350 and to track them. However, such annotation fields are not used to process data. Other types of annotation fields (not shown) include, but are not limited to, experiment definition identification and owner.

Next, in the case of "factorial design" experiment definitions 1350, a number of factors 1452 are specified. Examples of factors 1452 include, but are not limited to, tissue, compound, and concentration. Such factors are user specified but generally correspond to experimental conditions used to generate scans 1382. For example, consider the case in which a mouse is exposed to 0.5 mM of drug X for ten hours. After this, the animal is sacrificed and the cellular constituent levels in the liver are measured to form a scan 1382. Then, an experiment definition 1350 that will use this scan 1382 could use any combination of the following factors: species (mouse), concentration (0.5 mM), compound (drug X), time (ten hours), or tissue (liver). The present invention does not provide any practical limit on the number of factors that can be specified. In some instances only one factor is specified. In other instances two factors are specified. In more complex instances, between 3 and 5 factors are specified, between 4 and 10 factors are specified, or more than 10 factors are specified.

Experiment definition 1350 provides the ability to define levels 1454 for each factor specified. In other words, a level is a degree of a factor. For example, concentration can be considered a level of the factor compound. In another example, tissue types (e.g., brain, heart, liver) are levels for the factor "tissue".

Factors can be thought of as forming the dimensions of an n-dimensional datacube. For example, in the case where three factors 1452 are defined in an experiment definition 1350 (e.g., tissue, compound, and concentration), the n-dimensional datacube is a three dimensional datacube as illustrated in FIG. 15. Each cell in the n-dimensional datacube is a cross product of a level from each of the dimensions (factors) represented by the n-dimensional datacube. For example, cell 1560 (FIG. 15) represents the cross product of level "Compound 1" from the factor compound, level "1.0M" from the factor concentration, and factor "Tissue 1" from the factor tissue.

Those of skill in the art will appreciate that the term n-dimensional datacube is merely descriptive for a particular form of data structure. An n-dimensional datacube is a multiple dimensional array. Each dimension in the array is a set of sets representing a content domain (factor) so that the whole objected defines a multidimensional array of cells. A datacube can be implemented in many types of databases, including but not limited to structured query language databases, on-line analytical processing (OLAP) databases, multidimensional OLAP databases, and relational OLAP databases.

In the case where there are more than three factors, the visual construct illustrated in FIG. 15 breaks down and is no longer easy to graphically visualize. However, data cubes with more than three dimensions are a form of data structure that is well known in the art. The concept of a cell remains the same regardless of the number of dimensions (factors) in an experimental definition. A cell is the intersection of a level from each factor represented in the data cube of an experimental definition. Thus, in the case where there are four factors, each treatment group is the intersection (cross product) of a level from each of the four treatment groups.

In the case where the experiment definition 1350 is a "factorial design", each cell in the n-dimensional datacube defined by the experiment definition 1350 is referred to as a treatment group. Once the n-dimensional datacube has been defined, a user assigns scans 1382 to each treatment group. For example, in the case of cell (treatment group) 1560, the user assigns scans 1350 to cell 1560 that are from experiments involving "Compound 1" at "1.0M" with "Tissue 1." The assignment of scans 1382 to treatment groups is facilitated with user interface 1326 and other various modules, as described in more detail below. Each scan 1382 assigned to each treatment group in the n-dimensional datacube is processed into a corresponding profile 1380 in accordance with instructions provided by the experiment definition 1350, as described in further detail below.

In the case where an experiment definition 1350 is of the class "combine group" rather than "factorial design", factors and levels are not specified. Therefore, an n-dimensional datacube is not constructed. Rather, treatment groups are given by a user and scans 1382 are manually assigned to each treatment group. Thus, "combine group" experiment definitions 1350 contain significantly less information about the scans 1382 in such definitions. Thus, the "combine group" experiment definitions 1350 can not be used in all the forms of analysis supported by "factorial design" treatments groups. However, "combine group" experiment definitions 1350 have significant utility. They are easier to set up because factors and levels do not need to be defined. Further, "combine group" experiment definitions 1350 can be used to merge replicates, to export scans 1382 (or profiles 1380) from experiment definition system 1344 to other experiment processing architectures, or to import scans 1382 from other experiment processing architectures.

There are many different ways in which the instructions within experiment definition 1350 can be conceptualized. One way of conceptualizing these instructions is described with reference to FIG. 14. In FIG. 14, experiment definition 1350 includes instructions 1480 for profile builder pipeline 405 (FIG. 14, 1480). Instructions 1480 specify how scans 1382 in treatment groups in the n-dimensional datacube defined by experiment definition 1350 are processed by profile builder pipeline 405 to form profiles 1380. In fact, instructions 1480 can be in the form of a file in a directory of instructions 1480. A user can select a file of instructions 1480 in the same manner that a file is selected from a directory listing. See, for example, element 720 of FIG. 7C. It will be appreciated that there is no requirement to populate every single treatment group in an n-dimensional data cube with scans 1382. Typically, only those treatment cubes that will be subjected to analysis are populated with scans 1382 by a user. Thus, instructions 1480 typically only process select treatment groups. In some embodiments, the n-dimensional data cube comprises only those cells of a theoretical n-dimensional data cube that in fact have been populated.

Instructions 1484 for experiment builder pipeline 415 (FIG. 14, element 1484), are used in instances where a collection of profiles 1380 represent scans 1382 assigned to a particular treatment group (cell) that are replicates. As described herein, the term replicate refers to scans 1382 that are obtained under common (e.g., similar, identical) experimental conditions. Instructions 1484 direct experiment builder pipeline 415 on how to statistically combine profiles of such replicates in order to produce experiments. As used herein, the term "experiment" means the combination of profiles of replicates (e.g. profiles 1380 that represent scans 1382 taken under the same conditions). The data structure of an experiment is the same as that of a profile 1380. Indeed, the input used by experiment builder pipeline 415 is in fact a collection of profiles that, in turn, represent replicate scans. The only difference between an experiment and a profile is that the experiment is formed by combining profiles of replicate scans in an attempt to achieve more accurate data whereas a profile represents a single scan. Thus, to avoid confusion, an experiment can be alternatively termed a "replicate profile."

An advantage of the present invention is that instructions 1484 can be selected from a plurality of such instructions 1484 in the same way that a file is selected from a plurality of files in a directory using an operating system that has a graphical user interface. FIG. 9A illustrates the case in which the instructions 1484 with the name "Default Intensity Experiment Builder" have been selected for processing replicates in a treatment group in a given experiment definition 1350. Those of skill in the art will appreciate that there are many different ways in which replicates can be combined to form an experiment (replicate profile). Such different methods can each be represented as a set of processing instructions. Advantageously, the present invention allows the user to quickly select such processing instructions from a list of such instructions and store the selection in experiment definition 1350.

FIG. 9A provides a graphic overview of the processing instructions 1484 for "Default Intensity Experiment Builder". In step 902, each intensity value in each profile 1380 of a replicate (scan 1382) is adjusted to the same level of brightness. This adjustment is referred to in the art as normalization. In the case of the example illustrated in FIG. 9A, a linear normalization 902 is performed on intensity values in profiles in a given treatment group. In step 904 a forward transform is performed. In some embodiments, the forward transform changes the intensity values in each profile from an absolute form to a mathematical form that can be used to generate p-values (e.g., a logarithmic form). In step 906, systematic errors are removed from the profiles by experiment builder pipeline 415. In step 908, p-values for each intensity measurement in each profile that is being combined are determined. A p-value is a representation in the variance of a measurement. Measurements that have smaller p-values are more trusted. ANOVA step 908 is the step in which profiles are actually combined into an experiment (replicate profile). In step 910, a reverse transform is done. Reverse transform essentially undoes step 904, in essence putting intensity data values back to their original (profile) format. Then, in step 912, the expression data (experiment, replicate profile) is saved. Thus, the net effect of the process illustrated in FIG. 9A is that profiles that represent replicates are statistically combined to form a single profile that is now interchangeably termed an experiment or replicate profile.

Instructions 1482 for ratio builder pipeline 450 (FIG. 14, element 1482) are optional. This can be seen in FIG. 7C, where a toggle is left unmarked when experiment definition 1350 will not include instructions for ratio builder pipeline 450. In other words, there will only be instructions for ratio builder pipeline in specific instances where ratio experiments 406 are desired. A ratio experiment is defined herein as the combination of ratio profiles derived from replicates. Replicates are scans taken under identical experimental conditions. Ratio experiments are derived from the combination of ratio profiles in order to improve data reliability. In instances where ratio experiments are desired, toggle 724 (FIG. 7C) is triggered. Then, a file that includes instructions for ratio builder pipeline 450 can be selected from a plurality of such files using the interface illustrated in FIG. 7C and described in more detail below. When such a file is selected, it is included within the experiment definition 1350 and the ratio profiles derived from replicates designated by instructions 1482 are combined to produce a ratio experiment 406 in accordance with instructions 1482. Such ratio computations are performed by ratio builder pipeline 450.

At this stage, an example of a ratio profile as well as a ratio experiment is instructive. Ratio analysis is used to compare levels of factors to relative to a level of a factor that is designated as the baseline. Consider the case of a two factor factorial experiment in which each factor has two levels:

|  |  | Time | |
| --- | --- | --- | --- |
|  |  | 1 hour | 2 hours |
| Compound | Vehicle | V1 | V2 |
|  | Drug | D1 | D2 |

Assume that profile builder pipeline 405 (FIG. 4) has generated a profile for each of the scans V1, V2, D1, and D2 and the respective profiles are named V1', V2', D1', and D2'. Any of the levels (1 hour, 2 hours, vehicle, or drug) can be specified as a base line. For example, if Time—1 hour is specified as the baseline, then the following ratio profiles can be computed, V2'/V1' and D2'/D1'. If Compound—Vehicle is specified as the baseline, then the following ratios can be computed: D1'/V1' and D2'/V2'. The job of ratio builder pipeline 450 is to combine replicate ratio profiles in order to obtain a ratio experiment. A replicate ratio profile is obtained from replicates. For example, to create a ratio experiment for D1'/V1', scans $V1_a$, $V1_b$, . . . $V1_n$ are collected under the same conditions. $V1_a$, $V1_b$, . . . $V1_n$ are replicates because they are scans collected under the same conditions. In addition, $D1_a$, $D1_b$, . . . $D1_n$ are collected under the same conditions. $D1_a$, $D1_b$, . . . $D1_n$ are replicates of each other because they are scans collected under the same conditions. Each scan is then processed by profile builder pipeline to produce profiles $V1_a'$, $V1_b'$, . . . $V1_n'$ as well as $D1_a'$, $D1_b'$, . . . $D1_n'$ in accordance with instructions 1480 of experiment definition 1350 (FIG. 14). Then, the following ratio profiles are generated: $D1_a'$, $/V1_a'$, $D1_b'/V1_b'$, . . . $D1_n'/V1_n'$. Instructions for ratio builder pipeline 450 then direct ratio builder pipeline to combine $D1_a'/V1_a'$, $D1_b'/V1_b'$, . . . $D1_n'/V1_n'$ to form the ratio experiment D1'/V1' where D1'/V1' is the combination of $D1_a'/V1_a'$, $D1_b'/V1_b'$, . . . $D1_n'/V1_n'$.

In addition to forming ratio experiments, the present invention provides for the possibility of computing re-ratio experiments. Re-ratio experiments are experiments that contain ratios of one factor to another at a particular factor level. Typically, ratio experiments include a pooled standard present in each replicate whereas in re-ratio experiments, the pooled standard is removed.

Thus, instructions 1480, 1482, and 1484 direct pipelines 405, 450, and 415 on how to prepare scans 1382 in the n-dimensional datacube defined by experiment definition 1350 for analysis. Instructions 1480 are directed to converting scans 1382 into profiles 1380. Instructions 1482 are directed to construction ratio experiments from ratio profiles. Instructions 1484 are directed to combining replicates to form experiments. Once such data preparation has been accomplished, instructions for analysis pipeline 412 (FIG. 14, 1486) can be invoked. Instructions 1486 are used to analyze the processed data in the n-dimensional datacube. In typical embodiments, only designated treatment groups (cells) within the n-dimensional datacube are analyzed. Instructions for analysis pipeline 412 direct analysis pipeline 412 to perform specific analyses on specific treatment groups (cells) (e.g., ANOVA, Fisher Test, signature count, signature identification, etc.) in order to address a biological question. Each treatment group can contain profiles, ratio profiles, ratio experiments (combinations of ratios profiles), and experiments (combinations of profiles). Any of these data types can be analyzed using analysis pipeline 412 in accordance with instructions 1486 of experiment definition 1350 (FIGS. 4 and 14).

Experiment definition system 1344 allows for the specification of sets of profiles that should be analyzed together to answer a specific biological question. The user can specify grouping information (treatment groups), their structure (factorial design), and even trend factors (for factorial designs) for the profiles in the experiment definition system 1344. As described above, the user also specifies the processing pipelines for building profiles, experiments, and ratio experiments, and also data analysis pipelines (e.g., ANOVA, t-Test, clustering, classifiers, etc). Various types of clustering that can be performed using the data analysis pipeline of the present invention are described in Section 5.7 below. Various types of classifiers that can be applied using the data analysis pipeline of the present invention are described in Section 5.12, below. Other exemplary forms of analysis that can be performed using the data analysis pipeline are described in Section 5.13. Experiment definition system 1344 adds the flexibility that the same set of scans can be used to answer different biological questions (for example, by changing groups or group structure) or even to apply different processing pipelines to get optimal results.

Advantageously, the experiment definition system 1344 provides the user with the ability to maintain consistency of data analysis by rebuilding analyses if the experiment definition 1344 is changed. For example, if one or more profiles assigned to a treatment group are reloaded, the experiment definition system 1344 detects that change and all affected analysis results are recalculated. Experiment definition system 1344 also provides very quick re-processing and re-calculation with error models if a value was cut due to its inconsistency with the remainder of the data sets. Normalization processing can be performed at the level of raw data in the experiment definition system 1344 and not later on processed data, thereby simplifying the analysis. Exemplary normalization techniques that can be performed using the present invention are described in section 5.8, below.

In yet another embodiment, experiment definition system 1344 allows for the creation of a preferred experiment definition 1350 on the same set of scans 1382. This is accomplished by creating treatment groups and assigning scans 1382 to those groups. The experiment definition system provides greater flexibility for data analysis, by allowing for the combination of replicates in different ways, based on the scientific questions posed. For example, for a set of samples from animal A1 treated with drug X over different time courses 10 hours, 20 hours, and 30 hours, and a set of samples from animal A2 treated with the same drug over the same time courses, an effect of time differences can be studies by assigning both animal A1 and animal A2 profiles to the same treatment groups. Alternately, if animal to animal variations are being studied, the time profiles could be assigned to the same treatment groups.

In another embodiment, experiment definition system 1344 provides the ability to browse data using a top-down approach. By selecting the experiment definition, a list of profiles linked to the experiment definition, experiments (e.g., combined replicates), ratio or re-ratio experiments, ANOVA results, biosets, clusters, classifiers, etc. can be obtained. All information and analysis results related to the experiment definition are compiled together, thereby providing easy access to the structure of the experiment definition, all components, and analysis results. Both biosets and bioset groups can be associated with the experiment definition 1350 as results of data analysis, where the biosets are experiments ordered in terms of axes definitions. Also, biosets can be associated with the experiment definition as treatment groups.

In some embodiments, the user can partition the n-dimensional datacube of factors. Such partitioning results in two lists (groups). The first list (group) is a set of fixed factors and the second list (group) is the set of factors to iterate through. Some forms of analysis require such partitioning (e.g., 1 or 2-way ANOVA) whereas other forms of analysis do not require such partitioning (e.g., clustering).

5.3. Experiment Definition System Architecture

Experiment definition system 1344 has a set of tools for automating data analysis and for enforcing data consistency. Experiment definition system 1344 also provides for database storage of the instructions for the experiment definitions, and a user interface to create or modify experiment definitions 1350, view data analysis results, and monitor the progress of an experiment. The present invention also provides modules, components and a database schema 1352 for use in implementing the experiment definition system 1344.

In a preferred embodiment, experiment definition system 1344 provides a user interface 1346 (described in Section 5.3.1 infra) to create new experiment definitions 1350, search for experiment definitions 1350, and open associated profiles, experiments, and analysis results. Experiment definition system 1344 also provides an experiment definition setup module 1348 (described in Section 5.3.2 infra) for creating new or modifying existing experiment definitions 1350. The experiment definition database schema 1352 provides for storing and manipulating experiment definitions 1350 as described in Section 5.3.3 infra. The invention also provides an experiment definition engine 1354 (described in Section 5.3.4 infra) to manage data pipeline components, execute different analytical tools, and maintain consistency among all parts of the experiment definition 1350 (e.g., expression data, statistical analysis results, and data analysis results).

5.3.1. Experiment Definition User Interface

Figure 5:
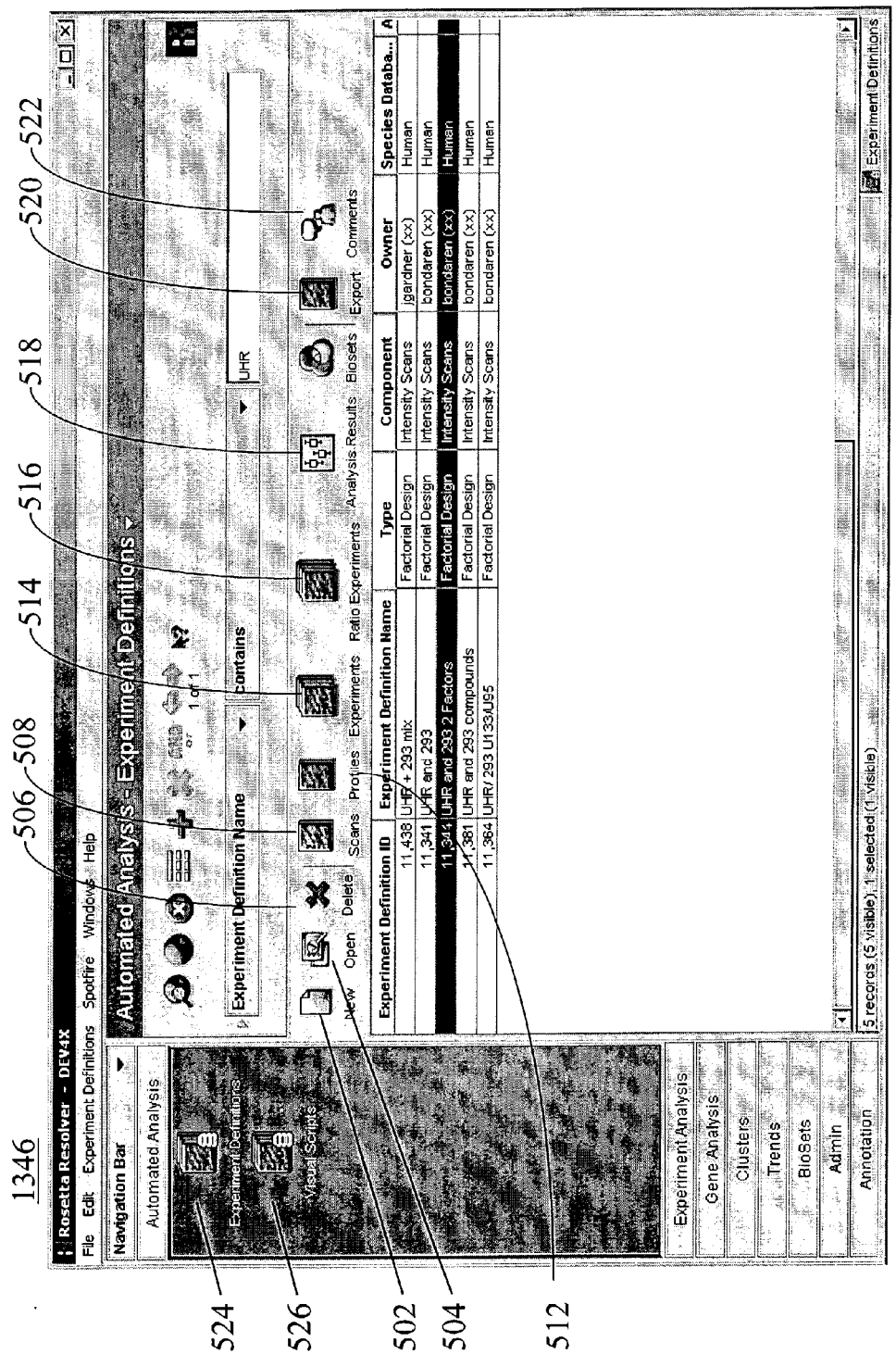
FIG. 5 illustrates a user interface in accordance with one embodiment of the present invention.

FIG. 5 illustrates an embodiment of the user interface 1346 that provides access to experiment definition system 1344. In some embodiments, a user can use interface 1346 to search the experiment definitions 1350 using a Rosetta Resolver® FlexQuery™ search engine (Rosetta BioSoftware, Kirkland, Wash.) or to perform the operations involved in constructing a new experiment definition 1350. Experiment Definitions icon 524 (FIG. 5) provides a list of all experiment definitions 1350 stored in system 1320 (FIG. 13).

The user is able to launch the experiment definition setup module 1348, discussed in greater detail below, to create new experiment definitions 1350 using a "New" command 502. The user is also able to open existing experiment definitions 1350 for modification using an "Open" command 504, or delete existing experiment definitions 1350 using a "Delete" command 506. In some embodiments, for system security, the New, Open, and Delete commands are enabled only for users who have been assigned the privilege to create, update, or delete experiment definitions 1350.

Interface 1356 also allows the user to launch different types of viewer tables for examination of data and for data analysis. The user can view scans 1382 using the "Scans" command 508 and/or the profiles 1386 that have been built using the "Profiles" command 512. In some cases, a scan 1382 is a data set that represents the scanned, imaged expression data from a microarray. A profile 1380 is the normalized scan that results from an error model applied to a scan 1382 in accordance with an experiment definition 1350. As different error models can be applied in normalizing data, multiple profiles 1380 can be built from the same scan 1382. The user can launch a table to view the experiments and treatment-groups for an experiment definition 1350 using the "Experiments" command 514. Launching a table using the "Ratio Experiments" command 516 allows a user to view the ratio experiments built from intensity profiles or re-ratio experiments built from ratio experiments. The user is also able to launch a table using the "Analysis Results" command 518 to view all experiment definition analysis results for the expression data, including biosets, clusters, classifiers, grow, trends, ANOVA summaries, and pathways. The user can also export the experiment definition with the expression data using an "Export" command 520, or comment on any experiment definition using the "Comments" command 522.

Interface 1346 also provides for the launching of a pipeline builder 900 using the "Visual Scripts" icon 526. Pipeline builder 900 provides for the assembly of automated data analysis instructions, which in turn automates data analysis.

5.3.2. Experiment Definition Setup Module

Figure 6:
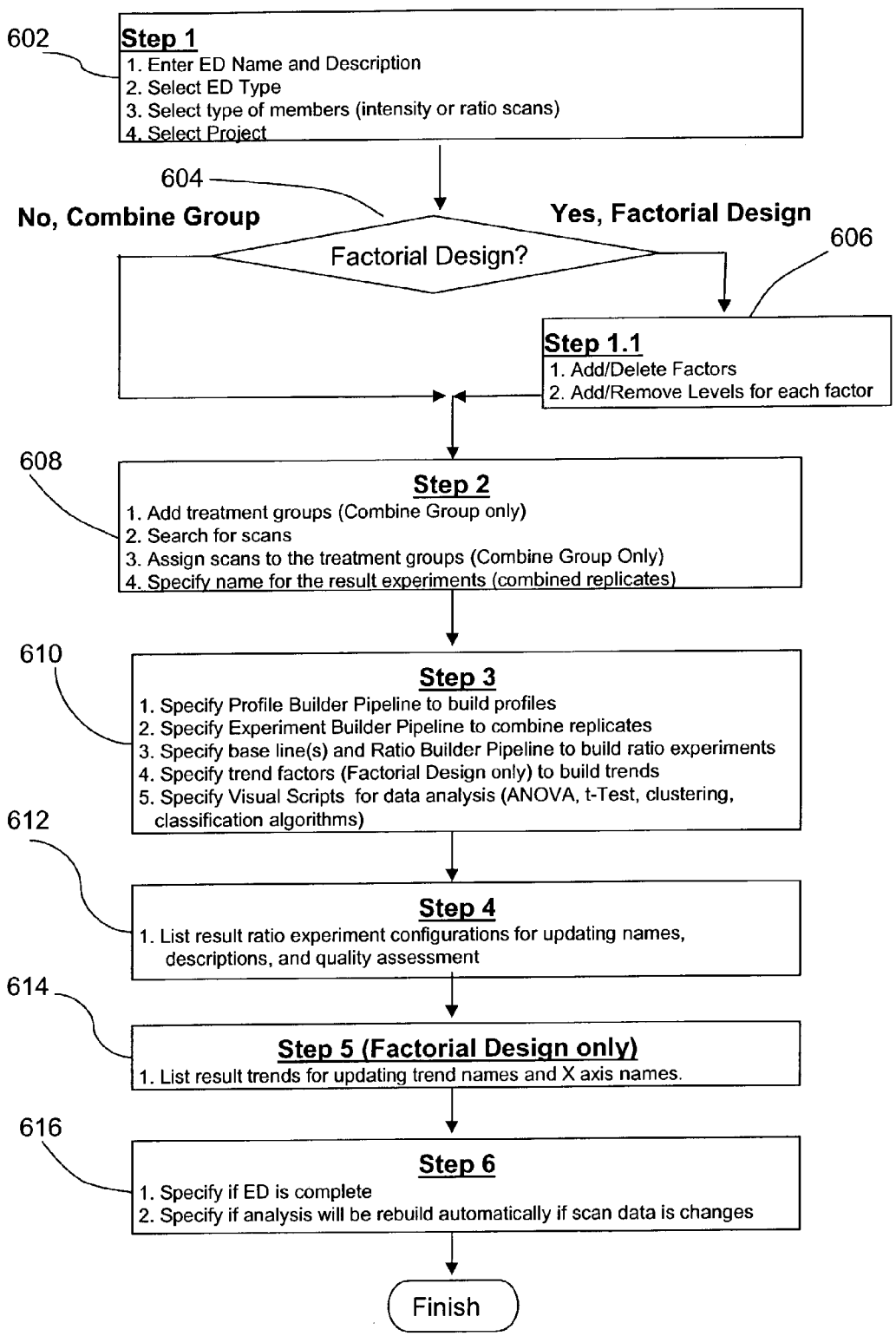
FIG. 6 is a flow chart illustrating the construction of an experiment definition for combine group or factorial design experiment definitions.

The present invention provides an experiment definition setup module 1348 (FIG. 13) to create experiment definitions 1350. Module 1348 is designed to be extendable for different experiment definition types. FIG. 6 shows a flow chart that illustrate the construction of an experiment definition using module 1348 for combine group or factorial design types of experiment definitions. The choice of experiment design is made in step 602 of the method illustrated in FIG. 6. The specific requirements for the experiment definition 1350 differ somewhat depending on the type of experiment design specified (e.g., whether "combine group" or "factorial design"). FIGS. 7A-E and 8A-D show screen shots of module 1348 corresponding to the steps of the method of constructing an experiment definition 1250 using the method illustrated in FIG. 6. These figures will be described in the following subsections.

5.3.2.1. Navigation of the Experiment Definition Wizard

Module 1348 can be launched by selecting the "New" command 502 in an embodiment of user interface 1346 or the "Experiment Definitions" icon 524. FIG. 7A shows module 1348 when it is first launched. As summarized in step 602 of FIG. 6, a name (ED Name 702) is assigned to the experiment definition 1350. Also, a description of the experiment definition can be entered. The user is also able to select the species database 706, and associate the project 712 in step 602. As used herein, a project is a collection of related experiment definitions. Each species database 706 includes scans derived from biological samples that belong to the same species. In the art, researchers have typically chosen to organize scans on a species specific basis so that all scans from a given species are assigned to a specific database created for that species. Accordingly, some embodiments of the present invention include a tag 706 for selecting a particular species database. However, some embodiments do not require that a species database and allow the user to organize scans in any type of database or collection of databases desired.

Figure 8A:
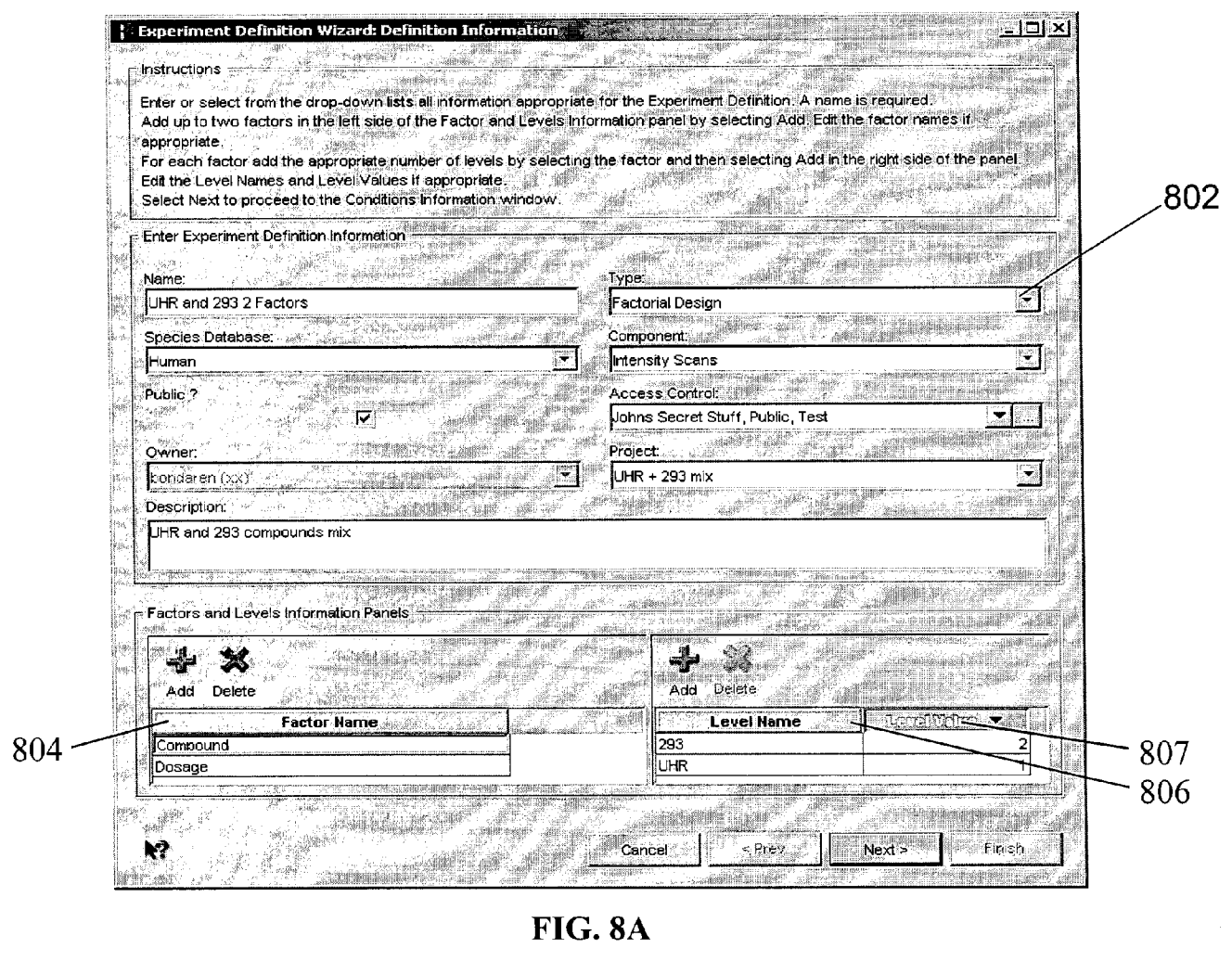
Figure 8B:
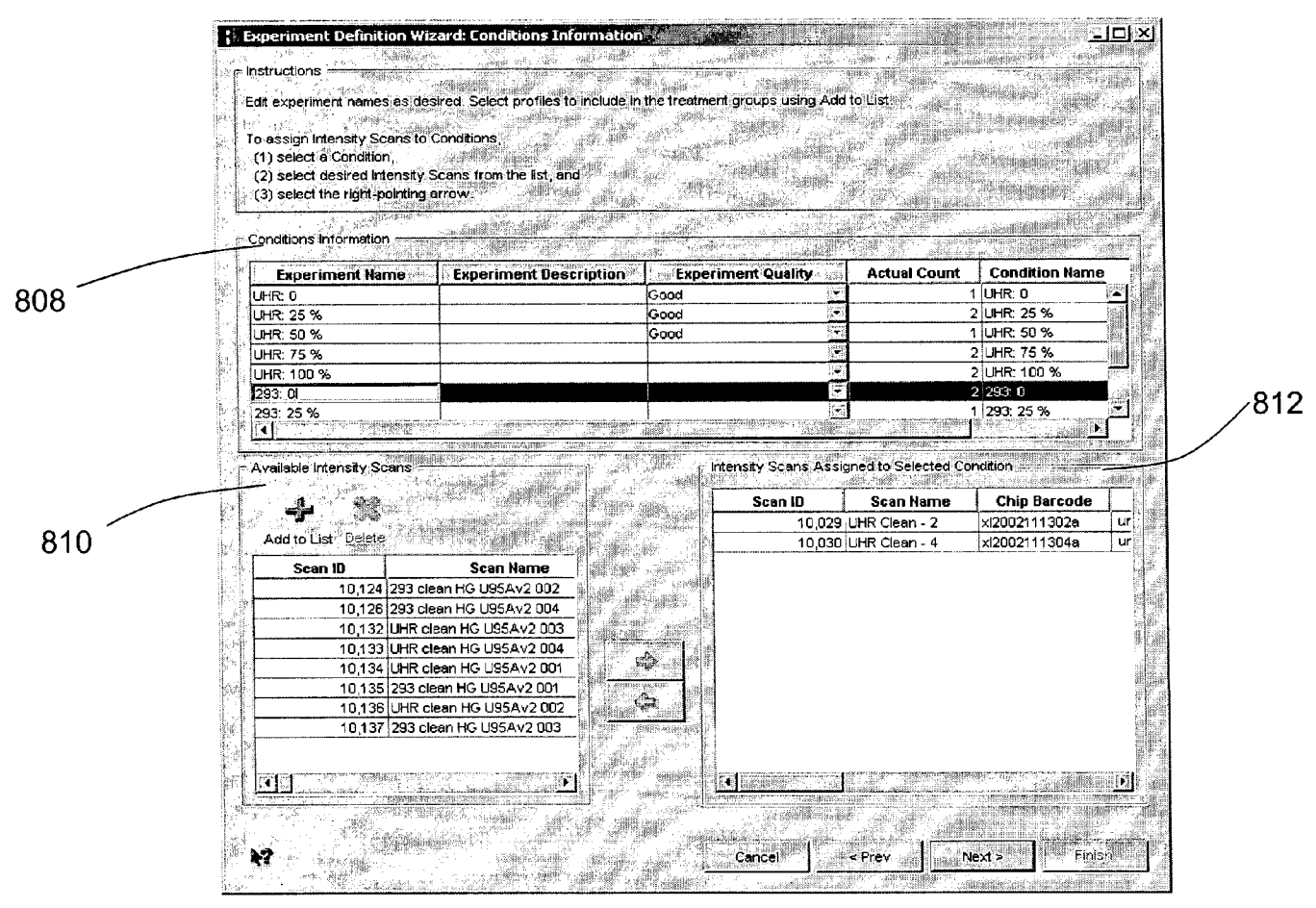

Scan (treatment group member) type is selected using components 708 menu. Potential scan types include, but are not limited to, intensity scans and ratio scans. At this stage, module 1348 also provides the user with access control 710 to the experiment definition, e.g., whether it will be public or private. A choice 604 (see FIG. 6) of an experiment type is made using a pull-down menu 714. In one embodiment, module 1348 supports two types of experiment definitions. They are "combine group" and "factorial design". Depending on the experiment definition type specified, module 1348 will generate an additional set of steps as illustrated in FIG. 6. If the "combine group" experiment type 714 is selected (604-No), module 1348 remains as shown in FIG. 7A. However, if the "factorial design" experiment type 802 is selected (604-Yes), the lower portion of module 1348 is activated as shown in FIG. 8A, where the names of the factors 804 and levels 806 to be used in the factorial design are entered or modified. FIG. 8A shows the additional steps needed for defining a factorial design (element 606 of FIG. 6).

When a factorial design experiment definition is chosen, one or more factors is entered, through the factor name frame 804 of module 1348. Any number of factors may be entered. Examples of factors include, but are not limited to type of compound, time, dosage, and animal used. Each factor optimally has one or more levels, that are added and edited through Level Name 806. Further, each level has a data type 807. For example, the data type for the levels of factors "time" and "dosage" is floating numbers, while the data type for the levels of factors "compound" and "animal" is string values. The user is able to enter any number of levels for each factor. In some embodiments, the mandatory fields for each level include name, text value, and numeric value. If the data type for the factor is a string value, then the numeric-value field is filled with a sequential number.

In step 608 of the experiment definition system session, the user is able to add treatment groups to the experiment definition 1350. This is done using "Conditions Information" frame 715 of module 1348 (see FIG. 7B). In an embodiment, at least two treatment groups are added. Since for a factorial design, the treatment groups are the cross products of the multiple levels of the factors, the treatment groups are already defined in step 606 when the factors and levels were assigned. When a given treatment group is selected, the user is able to search for intensity profiles, ratio profiles, intensity experiments, or ratio experiments in the available intensity scans frame 716 for inclusion in a list 718 for a given treatment group (FIG. 7B). Module 1348 offers the added flexibility that the user is able to assign one or more intensity profiles, ratio profiles, intensity experiments or ratio experiments to each treatment group as members, with the possibility that some treatment groups may not have members, or that the same profile or experiment is assigned to multiple treatment groups.

In instances where the experiment design is a "factorial design", the equivalent module 1348 for the factorial design experiment definition (FIG. 8B), the "Conditions Information" frame 808 does not typically provide the user with the ability to add treatment groups. Module 1348 again provides the user with the flexibility to search available intensity profiles, ratio profiles, intensity experiments or ratio experiments in the "Available Intensity Scans" frame 810, and assign one or more of them to each treatment group as members in the "Intensity Scans Assigned to Selected Conditions" frame 812.

Figure 8C:
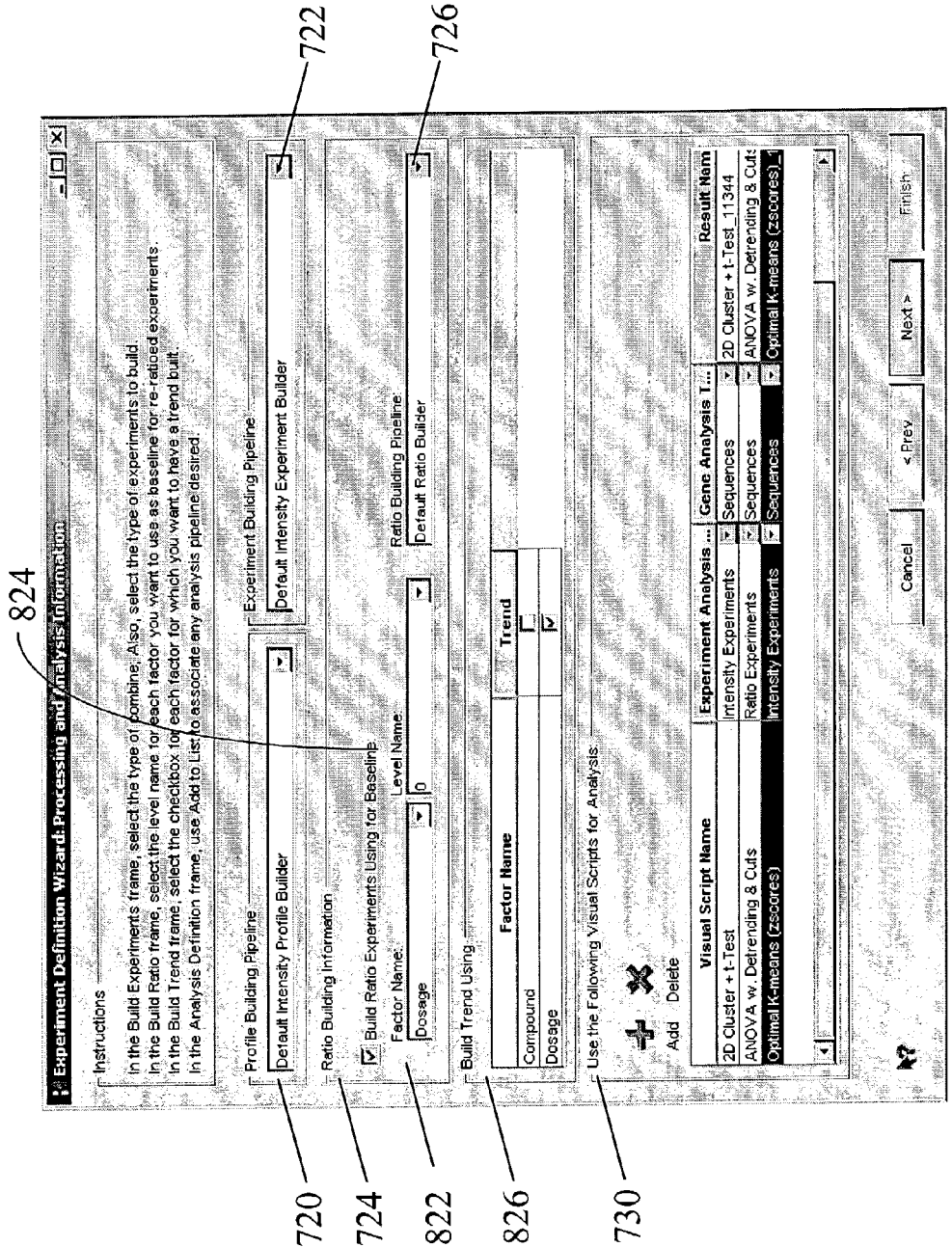
Figure 8D:
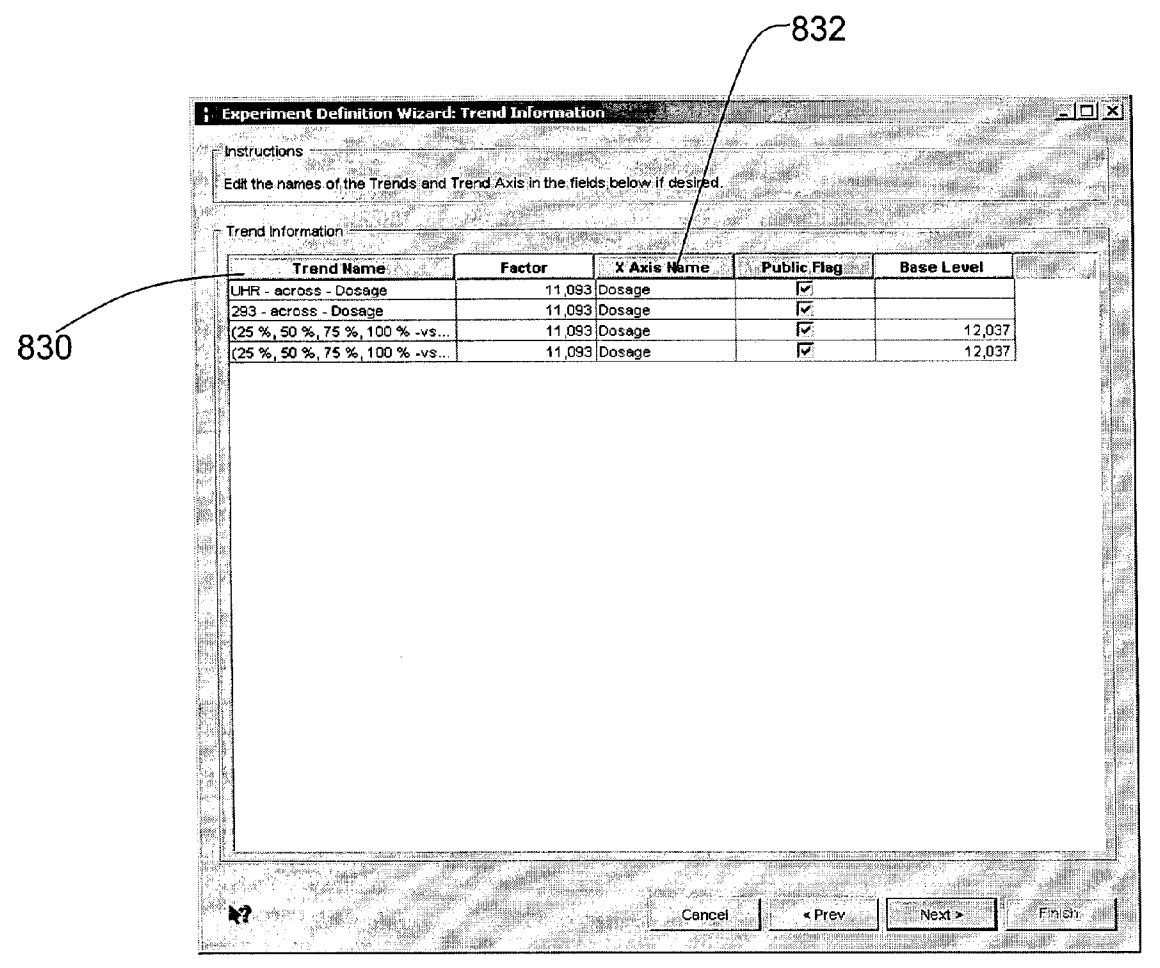

In step 610 of the experiment definition system session, the user uses module 1348 to specify what types of data analyses are to be performed. FIGS. 7C and 8C show the module 1348 screen for step 610 of the experiment definition session. The user specifies the instructions for profile builder pipeline 405 to be used for constructing profiles 1380 using field 720. If the user wishes to process replicates, the user selects instructions for experiment builder pipeline using field 722. In the ratio building information 724 frame the user can optionally instruct experiment definition system 1344 to construct ratio experiments (for intensity based data) or re-ratio experiments (for ratio based data) by choosing instructions for ratio building pipeline 415 using field 726 and specifying the base treatment group through condition name 728 (for combine group), or the base-line factor level through factor name 822 and level name 824, to be used as the baseline in the ratio or re-ratio experiment. Alternatively, there are a number of ways in which a baseline can be defined. For example, one of the levels of one of the factors can be marked as a baseline. Alternatively, the average of all of the scans in the experimental definition can be used as a baseline. In still another example, the average of any specified scans within or outside the experimental definition can be used as a baseline. In still another embodiment, a baseline can be established using one level of the factor with or without partitioning across other factors by averaging all scans in the selected level across all other factors. In addition, custom sets of scans from treatment groups can be used independently or in conjunction with other techniques to establish a baseline. An experiment definition 1350 with intensity-based treatment-group members can generate, e.g., profiles, combined replicates, ratio from intensity, or reratios from ratios, while an experiment definition with ratio-based treatment-group members can generate combined replicates and re-ratio experiment types. For the factorial design, the user can optionally choose to specify a trend factor (see, e.g., FIG. 4, Trend Factor 402) to be used to build trends automatically through build trend frame 826. The user is also able specify the visual script 730 to be used for data analysis (e.g., ANOVA, t-test, clustering, etc.). As used herein, the terms "visual script 730" and "instructions for data analysis pipeline 412" are interchangeable. The user is able to construct instructions for automated analysis through a visual scripting wizard discussed in greater detail in Section 5.3.2.2, below.

In step 612 (FIG. 6) of the experiment definition system session, for both combine group and factorial design experiment definitions (see FIG. 7D), module 1348 lists the experiment definitions for the ratio experiment, and provides the option of performing a quality assessment of the experiment definitions (by viewing the assigned ratio experiments 732), as well as updating or editing the names and descriptions of experiment definitions.

For factorial design experiment definitions (see FIG. 8D), module 1348 also builds a list of treatment groups defined by the factors and the levels of the factors. Module 1348 next lists the factor trend names 830 and the x-axis name 832, and also provides the user with the option of editing or updating them (step 614, FIG. 6). In a specific embodiment, the name of each treatment group is represented by a concatenation of level names from all factors, separated by dashes. Additionally, the user is able to view the specification of the public flag, and is then also able to change the access control label of the trend.

In the final step of the experiment definition system session (FIG. 6, 616), the user is able to specify through module 1348 whether the experiment definition 1350 is complete. The user is also able to specify if the analysis should be rebuilt automatically if any treatment group member is changed, e.g., if scan data changes, when a profile is reloaded, or an experiment is recombined (see 736, FIG. 7E). The specification that the experiment definition 1350 is complete serves as the instruction to the experiment definition system 1344 that the condition members have been assigned and the system can begin executing the experiment definitions 1350 through the experiment definition engine (discussed in greater detail in Section 5.3.4, infra), which submits the jobs into the different specified pipeline queues to perform defined tasks. Alternatively, the user can opt to save the experiment definition 1350 for execution at a later time, e.g., after having collected all of the scans 1382.

5.3.2.2. Visual Scripting Wizard

The experiment definition system 1344 also provides a visual scripting wizard 900, which is a processing pipeline manager for defining and constructing various pipelines used in the system. Examples of pipelines include data preprocessing pipelines, the profile building pipeline 720 to build profiles, the experiment builder pipeline 722 for combining profiles into experiments, the ratio building pipeline 726 for ratioing intensity data or re-rationing ratio data, and the visual script for analysis 730 for data analysis. User interface 1346 provides for the launching of visual scripting wizard using the "Visual Scripts" icon 526 of viewer 500 (see FIG. 5). FIG. 9A shows a screen shot of the processing pipeline manager for construction of an experiment builder pipeline 722. FIGS. 9B-C show the visual scripting manager for construction of a visual script for analysis 730 for two different data analysis types, ANOVA analysis (FIG. 9B), and clustering (FIG. 9C). The user is able to plug processing pipelines into the data loading framework and the analysis pipelines into the analysis framework in the experiment definition system The different pipelines provide for automation of the tasks and analyses as customized by the user for implementing the experiment definition.

Experiment definition system 1344 provides a plugins framework architecture that provides the user with the ability to create processing and analysis pipelines constructed from multiple plug-ins. Referring to FIGS. 9A, 9B, and 9C, the user provides the visual scripting wizard with a script name 914, a description 916 of the pipeline being constructed, and a set of available plugins 918 that are added to the pipeline in the order determined by the experimenter. The pipelines are constructed by selecting plugins from panel 918 and adding them to viewing frame 920. Viewing frame 920 of the visual script wizard provides the user with a representation of the pipeline. It shows the type of processing that is to be performed (e.g., normalize 902 the data), and the order in which the different processes are to be performed (e.g., normalize 902, followed by a forward transform 904). The sequence of plugins in the pipeline can be customized. The system provides that no two plugins are incompatible, in that the same data structure is used by each plugin.

The experiment building pipeline of FIG. 9A allows the user to construct the stages for combining profiles into experiments, which can include normalization 902, ANOVA analysis 908, etc. When a statistical test is selected in the viewing frame 920 of FIG. 9B, the visual scripting wizard provides an additional frame 926 to edit the parameters of the statistical test plugin, e.g., the fisher test 928. The experiment definition system launches the pipelines using a general execution mechanism, and persist the results into an expression data warehouse (MDW) and an analysis warehouse. The user is also able to save the results into data warehouses, e.g., by specifying save expression data 912. The user is also able to save and retrieve custom fields such as expression data, experiment, and sequence information, which are built as a result of execution of the custom pipelines.

The visual scripting wizard 900 is not linked to any experiment definition 1350. The user can access visual scripting wizard 900, input data, and perform analyses according to an experiment definition 1350. However, independently of the experiment definition system 1344. In an alternative embodiment, the user constructs one or more experiment definitions 1350 using visual scripting wizard 900. This alternative embodiment could, however, be labor intensive.

Visual scripting wizard 900 provides plugins for customizing pipelines that can later be selected for implementation of an experiment definition 1350. As used herein, a "customized pipeline" means instructions for a pipeline. Visual scripting wizard 900 provides plugins for data retrieval. These plugins allow for performing a simple search, performing an advanced search, adding column or row information, and merging saved pipeline results. Plugins also provide for mathematical operations include multiplying, dividing, adding and subtracting, and operations on sets (including union, intersect and minus operations). Visual scripting wizard 900 also provides a Plugin Manager for creating user-defined plugins and adding them to the list of available plugins 918. Visual scripting wizard 900 also provides the user with an ability to add or delete custom plug-ins and insert them in custom pipelines. The user is able to view the extension point display name 1000 attributed to the plugin, the extensions of the plugin at extension point 1002, and the description 1004. The user is also able to create their own plugins, such as a new clustering algorithm, using, e.g., Matlab (integrated through Java), etc.

5.3.3. Database Schema Requirements

The invention provides an experiment definition database schema 1352 for the data manipulation and analysis. FIG. 11 illustrates an experiment definition database schema 1352 according to the invention. Database schema 1352 centers on the ED_EXPERIMENT_DEFINITION 1100 (the experiment design experiment definition template) that comprises input fields for experiment definition 1350. The user sets the properties for the ED_EXPERIMENT_DEFINITION 1100 template and other templates using module 1348 (Section 5.3.2 supra). The user of the experiment definition session is identified by OWNER_USER_ID 1102. The user provides a name for the session within EXPERIMENT_DEFINITION_NAME field 1104 and an ID for the session through EXPERIMENT_DEFINITION_ID field 1106. The user chosen type of experiment design, which is reflected as an experiment definition type through specifying the fields of EXPERIMENT_DESIGN_TYPE_ID 1108, TYPE_NAME 1109, and TYPE_DESCRIPTION 1110, is linked to ED_EXPERIMENT_DEFINITION 1100 by ED_EXP_DEFINITION_TYPE template 1112. In an embodiment of the invention, the experiment definition type is specified using a controlled vocabulary. Other user-specified fields within ED_EXPERIMENT_DEFINITION template 1100 are the PROJECT_ID 1114 (using controlled vocabulary in a preferred embodiment) and PUBLIC_FLAG 1116 information for controlling access. If PUBLIC_FLAG 1116 is turned on, this indicates that all profiles, experiments, ratio experiments, and analysis results are to be shared with others. Otherwise only the owner has access. The experiment definition subsystem is linked to intensity and ratio experiments and profiles subsystems, bioset subsystem for data analysis results, and an automated analysis subsystem.

The experiment definition template comprises a DEFINED_FLAG 1118, which indicates that the treatment groups defined and treatment group members are assigned data analysis is to be performed. Schema 1352 also has a COMPLETE_FLAG 1120, which toggles to signal if all experiment definition fields are properly built and can be persisted. The template also comprises a delete experiment flag, which requests if the experiment results should be deleted if a treatment group member is deleted from the system. The delete flag is not used when only the association between a treatment group member and a treatment group is removed. Database schema 1352 also provides the capability of access to one or more species databases, and 21 C.F.R. Part 11 audit fields.

The ED_EXPERIMENT_DEFINITION 1100 template links to an ED_TREATMENT_GROUP 1126 template either directly, or via the ED_FACTOR 1128 and ED_LEVEL 1130 templates. The type of experiment design/definition selected, whether "combine group" or "factorial design", dictates how the treatment groups are created. If a combine group experiment definition is chosen, the ED_EXPERIMENT_DEFINITION 1100 template links to the ED_TREATMENT_GROUP 1126 template for the user to assign the treatment group members to the treatment groups. In an embodiment where a combine group or ratio group experiment design type is specified, a treatment group can be associated directly with an experiment definition. An intensity or ratio scan or profile can be a member of a single treatment group in a single experiment definition, or of many treatment groups of different experiment definitions. Preferably, each treatment group should have an expected count and an actual replicates count. The expected replicates count represents how many replicates should be assigned to a treatment group based on the experiment design. The actual replicates count is how many replicates (e.g., intensity or ratio scans) are actually assigned. The user can further specify the treatment-group member types (e.g., intensity profiles, ratio profiles, intensity experiments, or ratio experiments) using the ED_TREATMENT_GROUP 1126 template fields, including a group ID, name, experiment definition ID, member count, expected member count.

With choice of a factorial design experiment definition, the treatment groups are the cross product of the multiple levels of the factors, the ED_EXPERIMENT_DEFINITION 1100 template links to the ED_TREATMENT_GROUP 1126 template via the ED_FACTOR 1128 and ED_LEVEL 1130 templates. The experiment definition 1350 can have one or more factors 1452, as specified in the ED_FACTOR 1128 template. If a factorial design experiment definition is indicated as the type of experiment design (EXPERIMENTAL_DESIGN_TYPE_ID 1108), it will be mandatory to specify at least one factor. If more than two factors are specified, the experiment design can be treated as multiple two-dimensional factorial designs, depending on the number of factors beyond two and the number of levels within the one or more extra factors. Each factor is specified by an ID and is assigned a name. Preferably, the factor name is specified by a controlled vocabulary. Each factor is assigned one or more levels (ED_LEVEL 1130), where each level has a name, a numeric value, and an identification of the level data type (LEVEL_VALUE 1132), as well as an ID of the factor to which it belongs. Each level can be assigned to multiple treatment groups. One of the levels can be marked as a baseline (see FIG. 4) for building ratio and re-ratio experiments using a ratio base flag (not shown). In an alternate embodiment, one factor is specified as a trend factor. Any given level can have multiple trend templates for the different experiment types, as assigned under the experiment definition trend configuration template ED_TREND_CONFIG 1134. The template provides the trend name, the x-axis name, and public flag information to the experiment definition engine for building trends.

The same intensity profile, ratio profile, intensity experiment or ratio experiment can be a member of several treatment groups of different experiment definitions and/or a member of only one treatment group in a given experiment design. In such cases, the link between a treatment group and a hybridization protocol ("hyb") can be provided for intensity and ratio profiles as members of the treatment group. A laboratory information management system (LIMS) loader can create this link before the profiles are loaded into the system. Additionally, this link can be used to associate newly loaded profiles with the treatment group.

In some embodiments, experiments in the experiment definition system are based on an experiment configuration using the ED_EXPERIMENT_CONFIG 1136 template. In one embodiment, all ratio and intensity experiments built by the system are based on an experiment configuration. The ED_EXPERIMENT_CONFIG 1136 template provides the name of the experiment and description information for the data-pipeline components that are building the experiments. The experiments inherit the PUBLIC_FLAG 1116 from the experiment definition. A pair sample treatment-group and base treatment-group define the template for the experiment. The base treatment group will be optional for the template and used just for building ratio and re-ratio experiments. For a given experiment configuration, the combination of sample treatment-group, base treatment-group, and experiment type is unique. Module 1348 provides the capability to combine statistical replicates and to change experiment names.

Any number of external parameter-value pairs can be associated with each treatment group member for data analysis or regression testing. The ED_EXPERIMENT_DEFINITION 1100 template can be associated with one or more automated analysis pipelines (AA_PIPELINE_RUN 1122), that link to warehouses for saving the results of pipeline executions for further viewing (AA_PIPELINE_RESULTS 1124). The experiment definition can be associated with multiple statistical tests algorithms (such as ANOVA, t-tests, etc.) and algorithm parameters. Preferably, the algorithm results are stored as a binary large object (BLOB) and linked to the experiment definition. BLOB is a representation (mapping) of an SQL BLOB value. An SQL BLOB in the Java™ programming language is a built-in type that stores a binary large object as a column value in a row of a database table. In different embodiments, any number of summaries can be built for the same experiment definition.

5.3.4. Experiment Definition Engine

The experiment definition system of the invention also provides an experiment definition engine 1354, that provides for the execution of an experiment definition 1350. The purposes of engine 1354 include submitting jobs into the different data pipeline components, watching for the dependencies, job completions, and experiment definition changes, and triggering actions to ensure consistency of the experiment design expression data and analysis results.

Engine 1354 serves multiple functions in system 1344. Engine 1354 switches the COMPLETE_FLAG 1120 from 1 to 0 when selected changes are made to the experiment definition 1350. Non-limiting examples of such changes include changing the number of factors, levels, or treatments group, adding or removing treatment-group members, and removing an intensity profile or associated ratio. Engine 1354 submits jobs to the combine server when the COMPLETE_FLAG 1120, included in the ED_EXPERIMENT_DEFINITION template of FIG. 11, is switched from 0 to 1, as indicated in the Definition States field 734 (FIG. 7E). The jobs are submitted through the different data processing and analysis pipelines that were customized using visual scripting wizard 900 (FIGS. 9A-C).

Engine 1354 updates the treatment group member when the profile is reloaded for ratio and intensity profile members. Engine 1354 associates profiles with a treatment group when the profile is reloaded using a link between a treatment group member and hyb. Additionally, engine 1354 removes a treatment group member if an experiment is deleted from the system.

In another embodiment, engine 1354 submits jobs to the Ratio-Builder-Server-Component when either the base line level is specified and the COMPLETE_FLAG 1120 switches from 0 to 1, or the COMPLETE_FLAG is 1 and a new base line level is specified. When all requirements for the input experiments are met, the COMPLETE_FLAG switches from 0 to 1, and engine 1354 submits jobs to the automated server components for each automated analysis pipeline associated with the experiment definition.

Engine 1354 also provides the capability of checking existing trends against new trends to build that are specified within the ED_TREND_CONFIG 1134 template. Trends can be created for all combine group and ratio experiment types, including combined replicates, ratio or re-ratio, ANOVA (for intensity based data), and ANOVA ratio (for intensity based data). Engine 1354 removes trends that are not in a list to build and rebuild missing trends.

The experiment definition system offers the increased flexibility that data pipeline components are independent of each other, and do not submit jobs into the queues. Engine 1354 tracks the dependencies between pipeline components, distributes jobs, and enforces business rules to ensure completion of data analysis. Module 1348 queues the change to use the experiment template for building any type of experiment, including combine, ratio, etc. The experiment definition system 1344 of the present invention also provides migration capabilities from other systems.

5.3.5. Data Pipeline Requirements

FIG. 12 illustrates the data loading and manipulation framework of experiment definition system 1344. Systematic error in the scan data can be removed using a preprocessing pipeline 1202, and can be stored independently of an experiment definition multidimensional analysis warehouse 1212. The experiment definition system 1344 then provides the profile building pipeline 1204, the experiment builder pipeline 1206, ratio builder pipeline 1208 and the analysis pipelines 1210. The results of any of the given pipelines are stored in the experiment definition multidimensional analysis warehouse 1212.

For increased compatibility with external systems, experiment definition system 1344 will create a treatment group under the "Default" experiment definition for each scan 1382 combine group loaded using a LIMS loader. Experiment definition system 1344 creates an experiment definition 1350 for each project loaded using the LIMS loader, and moves treatment groups from the "Default" experiment definition 1350 to the experiment definition project defined by the user. The PUBLIC_FLAG 1116 propagates from the experiment definition to the experiments and data analysis results.

The data pipeline system supports "import" and "export" experiment definitions 1350 using a microarray gene expression markup language (MAGE-ML) format. MAGE-ML is a language that describes and communicates information about microarray-based experiments xml.coverpages.org/mageML.html). MAGE-ML is based on XML and is used to describe microarray designs, microarray manufacturing information, microarray experiment setup and execution information, gene expression data and data analysis results.

5.4. Measured Signals

The present invention provides systems and methods for manipulating and analyzing measured signals obtained using an experiment design type, e.g., measured intensity signals obtained in a microarray gene expression experiment. Measured signals from any experiment design can be manipulated and analyzed by the experiment definition system of the present invention. For example, the measured signals can represent measurements of the abundances or activities of cellular constituents in a cell or organism; or measurements of the responses of cellular constituents in a living cell or organism to a perturbation to the living cell or organism. As used herein, the term "cellular constituent" comprises individual genes, proteins, mRNA expressing a gene, a cDNA, a cRNA, and/or any other variable cellular component or protein activities, degree of protein modification (e.g., phosphorylation), for example, that is typically measured in a biological experiment by those skilled in the art. Furthermore, the term "cellular constituents" comprises biological molecules that are secreted by a cell including, but not limited to, hormones, matrix metalloproteinases, and blood serum proteins (e.g., granulocyte colony stimulating factor, human growth hormone, etc.). Such measured intensity signals permit analysis of data using traditional statistical methods, e.g., ANOVA and regression analysis (e.g., to determine statistical significance of measured data).

The experiment definition system 1344 of the invention is applicable to measured signals obtained by both single-channel measurement and two-channel measurement. As used herein, a "single-channel measurement" refers broadly to where measurements of cellular constituents are made on a single sample (e.g., a sample prepared from a living cell or organism having been subjected to a given condition) in a single experimental reaction, whereas a "two-channel measurement" refers to where measurements of cellular constituents are made distinguishably and concurrently on two different samples (e.g., two samples prepared from cells or organisms, each having been separately subjected to a given condition) in the same experimental reaction. The cells or organisms from which the two samples in a two-channel experiment are derived can be subjected to the same condition or different conditions. The expression "same experimental reaction" means in the same reaction mixture, for example, by contacting with the same reagents in the same composition at the same time (e.g., using the same microarray for nucleic acid hybridization to measure mRNA, cDNA or amplified RNA; or the same antibody array to measure protein levels). In this disclosure, a measurement in a "same-vs.-same" experiment is referenced. As used herein, such a measurement refers to either a two-channel measurement performed in an experiment in which the two samples are derived from cells or organism having been subjected to the same condition or a measurement obtained in two single-channel measurements performed separately with two samples which are derived from cells or organisms having been subjected to the same condition.

While the experiment design is described in terms of using measured signals obtained from a microarray experiment, it will be clear to a person of ordinary skill in the art that the experiment definition systems of the present invention used for digitally reflecting experiment design are equally applicable to signals measured in many other kinds of experiments, e.g., signals measured in a protein array experiment or signals measured in a 2D protein gel experiment.

5.4.1. Biological State and Expression Profiles

The state of a cell or other biological sample is represented by cellular constituents (any measurable biological variables) as defined in Section 5.4.1.1, infra. Those cellular constituents vary in response to perturbations such as time or dosage, or under different conditions. The measured signals can be measurements of such cellular constituents or measurements of responses of cellular constituents.

5.4.1.1. Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms. In preferred embodiments, the biological sample comprises a living cell or organism.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample) e.g., of mRNA or proteins, or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by a vector S, where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on"

indicates a transcriptional rate above a predetermined threshold and value "off" indicates a transcriptional rate below that threshold.

In preferred embodiments, the measured signals are measured in a microarray gene expression experiment. In other preferred embodiments, the measured signals are measured in a protein array experiment or a 2D gel protein experiment.

In one preferred embodiment, the measured signals are signals obtained in an microarray experiment in which two spots or probes on a microarray are used for obtaining each measured signal, one comprising the targeted nucleotide sequence, i.e., the target probe, e.g., a perfect-match probe, and the other comprising a reference sequence, i.e., a reference probe, e.g., a mutated mismatch probe. The RP probe is used as a negative control, e.g., to remove undesired effects from non-specific hybridization. In one embodiment, the measured signal obtained in such a manner is defined as the difference between the intensities of the target probe and reference probe.

5.4.1.2. Biological Rresponses and Expression Profiles

The responses of a biological sample to a perturbation, e.g., under a condition, such as the application of a drug, one of the factors in an experiment design, can be measured by observing the changes in the biological state of the biological sample. For example, the responses of a biological sample can be responses of a living cell or organism to a perturbation, e.g., application of a drug, a genetic mutation, an environmental change, and so on, to the living cell or organism. A response profile is a collection of changes of cellular constituents. In the experiment design, the response profile of a biological sample (e.g., a cell or cell culture) to the perturbation m can be represented by a vector $v^{(m)}$, where $v_i^m$ is the amplitude of response of cellular constituent i under the perturbation m. Each $v_i^m$ is then the value assigned to one of the levels of a factor of the experiment design. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes.

In another preferred embodiment of the invention, the biological response to the application of a drug, a drug candidate or any other perturbation, is measured by the induced change in the expression levels of a plurality of exons in at least 2 genes, preferably more than 10 genes, more preferably more than 100 genes and most preferably more than 1,000 genes. In some embodiments of the invention, the response is simply the difference between biological variables before and after perturbation. In some preferred embodiments, the response is defined as the ratio of cellular constituents before and after a perturbation is applied.

5.5. Measurement of Drug Response Data

Drug responses are obtained for use in the experiment design and experiment definition system of the present invention by measuring the gene expression state changed by drug exposure. The biological response described on the exon level can also be measured by exon profiling methods. The measured response data include values representing gene expression level values or gene expression level ratios for a plurality of genes.

To measure drug response data, cell can be exposed to graded levels of the drug or drug candidate of interest. When the cells are grown in vitro, the compound is usually added to their nutrient medium. The drug is added in a graded amount that depends on the particular characteristics of the drug, but usually will be between about 1 ng/ml and 100 mg/ml. In some cases a drug will be solubilized in a solvent such as DMSO.

The exon expression profiles of cells exposed to the drug and of cells not exposed to the drug are measured according to the methods described in the previous section. Preferably, gene transcript arrays are used to find the genes with altered gene expression profiles due to exposure to the drug.

It is preferable for measurements of drug responses, in the case of two-colored differential hybridization described above, to measure with reversed labeling. Also, it is preferable that the levels of drug exposure used provide sufficient resolution of rapidly changing regions of the drug response, e.g., by using approximately ten levels of drug exposure.

5.6. Methods of Analyzing Measured Signals

The present invention provides methods of analyzing measured signals from the experiment designs. Statistical data processing and analysis methods known in the art can be used in conjunction with the experiment definition system.

In one embodiment, the invention provides a method of analyzing measured signals based on the experiment design. Most statistical tests, such as ANOVA and t-test, require that the variance of the data is a constant. In preferred embodiments of the invention, the measured signals can be transformed by methods known in the art to have this property, i.e., statistical tests performed on such a transformed signal satisfy the underlying requirement of constant variance.

5.7. Clustering Techniques

The subsections below describe exemplary methods for clustering data in accordance with the present invention. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; Backer, 1995, *Computer-Assisted Reasoning in Cluster Analysis*, Prentice Hall, Upper Saddle River, N.J.; and Duda et al., 2001, *Pattern Classification*, John Wiley & Sons, New York, N.Y.

5.7.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n−1 clusters, the next is a partition into n−2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, *Pattern Classification*, John Wiley & Sons, N.Y., 2001, p. 551.

5.7.1.1. Agglomerative Clustering

Agglomerative (bottom-up clustering) procedures start with n singleton clusters and form a sequence of partitions by successively merging clusters. The major steps in agglomerative clustering are contained in the following procedure, where c is the desired number of final clusters, $D_i$ and $D_j$ are clusters, $x_i$ is an element, and there are n such elements:

| | |
|---|---|
| 1 | begin initialize c, $\hat{c} \leftarrow n$, $D_i \leftarrow \{x_i\}$, $i = 1, \ldots, n$ |
| 2 | do $\hat{c} \leftarrow \hat{c}-1$ |
| 3 | find nearest clusters, say, $D_i$ and $D_j$ |
| 4 | merge $D_i$ and $D_j$ |
| 5 | until $c = \hat{c}$ |
| 6 | return c clusters |
| 7 | end |

In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-neighbor algorithm. The nearest-neighbor algorithm uses the following equation to measure the distances between clusters:

$$d_{\min}(D_i, D_j) = \min_{\substack{x \in D_i \\ x' \in D_j}} \|x - x'\|.$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest subsets. The merging of $D_i$ and $D_j$ corresponds to adding an edge between the nearest pari of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., id, pp. 553-554.

Farthest-neighbor algorithm. The farthest-neighbor algorithm uses the following equation to measure the distances between clusters:

$$d_{\min}(D_i, D_j) = \max_{\substack{x \in D_i \\ x' \in D_j}} \|x - x'\|.$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average linkage algorithm. Another agglomerative clustering technique is the average linkage algorithm. The average linkage algorithm uses the following equation to measure the distances between clusters:

$$d_{avg}(D_i, D_j) = \frac{1}{n_i n_j} \sum_{x \in D_i} \sum_{x' \in D_j} \|x - x'\|.$$

Hierarchical cluster analysis begins by making a pair-wise comparison of all gene analysis vectors 84 or gene expression vectors 304 in a set of quantitative trait locus vectors or gene expression vectors. After evaluating similarities from all pairs of elements in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n–1 times until only a single element remains. Consider six elements, A-F having the values:

A{4.9}, B{8.2}, C{3.0}, D{5.2}, E {8.3}, F{2.3}.

In the first partition, using the average linkage algorithm, one matrix (sol. 1) that could be computed is:

A{4.9}, B-E{8.25}, C{3.0}, D{5.2}, F{2.3}. (sol. 1)

Alternatively, the first partition using the average linkage algorithm could yield the matrix:

A{4.9}, C{3.0}, D{5.2}, E-B{8.25}, F{2.3 1}. (sol. 2)

Assuming that solution 1 was identified in the first partition, the second partition using the average linkage algorithm will yield:

A-D{5.05}, B-E{8.25}, C{3.0}, F{2.3} (sol. 1-1)

or

B-E{8.25}, C{3.0}, D-A{5.05}, F{2.3}. (sol. 1-2)

Assuming that solution 2 was identified in the first partition, the second partition of the average linkage algorithm will yield:

A-D{5.05}, C{3.0}, E-B{8.25}, F{2.3}    (sol. 2-1)

or

C{3.0}, D-A{5.05}, E-B{8.25}, F{2.3}.    (sol. 2-2)

Thus, after just two partitions in the average linkage algorithm, there are already four matrices. See Duda et al., Pattern Classification, John Wiley & Sons, N.Y., 2001, p. 551.

Centroid algorithm. In the centroid method, the distances or similarities are calculated between the centroids of the clusters D.

Sum-of-squares algorithm. The sum of squares method is also known as the "Wards' method." In the Wards' method, cluster membership is assessed by calculating the total sum of squared deviations from the mean of a cluster. See Lance and Williams, 1967, A general theory of classificatory sorting strategies, *Computer Journal* 9: 373-380.

5.7.1.2. Clustering with Pearson Correlation Coefficients

In agglomerative hierarchical clustering with Pearson correlation coefficients, similarity is determined using Pearson correlation coefficients between data elements. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.7.1.3. Divisive Clustering

In some embodiments, a divisive clustering procedure is used. Divisive (top-down clustering) procedures start with all of the samples in one cluster and form the sequence by successively splitting clusters. Divisive clustering techniques are classified as either a polythetic or a monthetic method. A polythetic approach divides clusters into arbitrary subsets.

5.7.2. K-Means Clustering

In k-means clustering, data elements are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., id., pp. 526-528. A related approach is the fuzzy k-means clustering algorithm, which is also known as the fuzzy c-means algorithm. In the fuzzy k-means clustering algorithm, the assumption that every gene analysis vector 84 or gene expression vector 304 is in exactly one cluster at any given time is relaxed so that every vector has some graded or "fuzzy" membership in a cluster. See Duda et al., id., pp. 528-530.

5.7.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22:1025-1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and $k_{min}$ in are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom).

5.7.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based on training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

5.7.5. Self-Organizing Maps

A self-organizing map is a neural-network that is based on a divisive clustering approach. The aim is to assign genes to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identify of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.8. Exemplary Normalization Routines

This section describes representative normalization routines that can be performed by profile builder pipeline 405. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publically available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For. microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$\text{Z-score}_{ij}=(I_{ij}-mnI_i)/sdI_i,$$

and $$\text{Zdiff}_j(x,y)=\text{Z-score}_{xj}-\text{Z-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (medianI$_i$) for all of the spots in that sample. Thus, upon normalization by the median intensity normalization method, the raw intensity $I_{ij}$ for probe i and spot j, has the value Im$_{ij}$ where, $$Im_{ij}=(I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianI$_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value Im$_{ij}$ where, $$Im_{ij}=\log(1.0+(I_{ij}/\text{median}I_i)).$$

Yet another normalization protocol is the Z-score standard deviation log of intensity protocol. In this protocol, raw expression intensities are normalized by the mean log intensity (mnLI$_i$) and standard deviation log intensity (sdLI$_i$). For microarray data, the mean log intensity and the standard deviation log intensity is computed for the log of raw intensity of control genes. Then, the Z-score intensity ZlogS$_{ij}$ for probe i and spot j is:

$$Z\log S_{ij}=(\log(I_{ij})-mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)-mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLI$_i$ and the mean absolute deviation log intensity madLI$_i$ are computed for the log of raw intensity of control genes. Then, the Z-score intensity ZlogA$_{ij}$ for probe i and spot j is:

$$Z\log A_{ij}=(\log(I_{ij})-mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5-medianBkgdCy5)/(medianCy3-medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.9. Transcriptional State Measurements

The section provides some exemplary methods for measuring the expression level of genes, which are one type of cellular constituent. One of skill in the art will appreciate that this invention is not limited to the following specific methods for measuring the expression level of genes in each organism in a plurality of organisms in order to derive scan 1382 (FIG. 13) data.

5.9.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays for simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

Exemplary microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (ie., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least about 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a CDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. In some embodiments, such polynucleotides are of the length of 15 to 200 bases. In other embodiments, such polynucleotides are of length 20 to 100 bases. In still other embodiments, such polynucleotides are of length 40 to 60 bases. However, the size of such polynucleotides is highly application dependent. Accordingly, other sizes are possible. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000, or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 50 bases (See The Genome Sequencing Consortium, 2001, Initial sequencing and analysis of the human genome, Nature 409, 860-921). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways.

More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occur in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that a low more advantageous use of different probe schemes are also encompassed.

In some embodiments, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately 30,000 to 40,000 genes (see Venter et al., 2001, The Sequence of the Human Genome, *Science* 291:1304-1351).

In some embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exon expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual*, 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.9.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.9.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251: 767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510, 270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.9.1.3. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo-dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716, 785; 5,545,522 and 6,132,997; see also, U.S. Pat. No. 6,271,002, and PCT Publication No. WO 02/44399 dated Jun. 6, 2002). Both oligo-dT primers (U.S. Pat. Nos. 5,545, 522 and 6,132,997) or random primers (PCT WO 02/44399 dated Jun. 6, 2002) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, $^{15}N$ and $^{125}I$. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.9.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins-or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al., are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.9.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of differences of an order of about 1.5 fold to about 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.9.2. Other Methods of Transciptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci.* USA 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.9.3. Measurement of Other Aspects of the Biological State

In various embodiments of the present invention, aspects of the biological state other than the transcriptional state, such as the translational state, the activity state, or mixed aspects can be measured. Thus, in such embodiments, cellular constituent data can include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in Sections 5.10 and 5.11, below.

5.10. Translational State Measurements

Measurement of the translational state can be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad.* Sci. USA 93:1440-1445; Sagliocco et al., 1996, *Yeast* 12:1519-1533;

Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.11. Measuring Other Aspects of the Biological State

Even though methods of this invention are illustrated by embodiments involving gene expression or translation, the methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from the organism of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes may be recorded as often as several times each hour. During one incubation, more than 5,000 phenotypes can be tested. See, for example, Bochner et al, 2001, *Genome Research* 11, 1246-55.

In some embodiments of the present invention, the cellular constituents that are measured are metabolites. Metabolites include, but are not limited to, amino acids, metals, soluble sugars, sugar phosphates, and complex carbohydrates. Such metabolites may be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, *J. Gen. Microbiol.* 137, 69-79; Naumann et al., 1991, *Nature* 351, 81-82; Naumann et al., 1991, In: *Modern techniques for rapid microbiological analysis*, 43-96, Nelson, W. H., ed., VCH Publishers, New York), Raman spectrometry, gas chromotagraphy-mass spectroscopy (GC-MS) (Fiehn et al., 2000, *Nature Biotechnology* 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods may be combined with established chemometric methods that make use of artificial neural networks and genetic programming in order to discriminate between closely related samples.

5.12. Classification Schemes

The data analysis pipeline of the present invention can apply a wide range of classification schemes. A few representative classification schemes are present in this section. In some embodiments the classification scheme is a supervised classification scheme whereas in other embodiments the classification scheme is unsupervised. Supervised classification schemes in accordance with the present invent use techniques that include, but are not limited to, linear discriminant analysis and linear regression. Linear regression is a broad category of statistics that includes, but is not limited to, multiple linear regression, partial least squares regression, and principal components regression. Unsupervised classification schemes in accordance with the present invention include, but are not limited to, hierarchical cluster analysis, non-hierarchical cluster analysis, artificial neural networks, and self-organizing maps. Unsupervised classification schemes are discussed in Section 5.7, above.

Figure 1A:
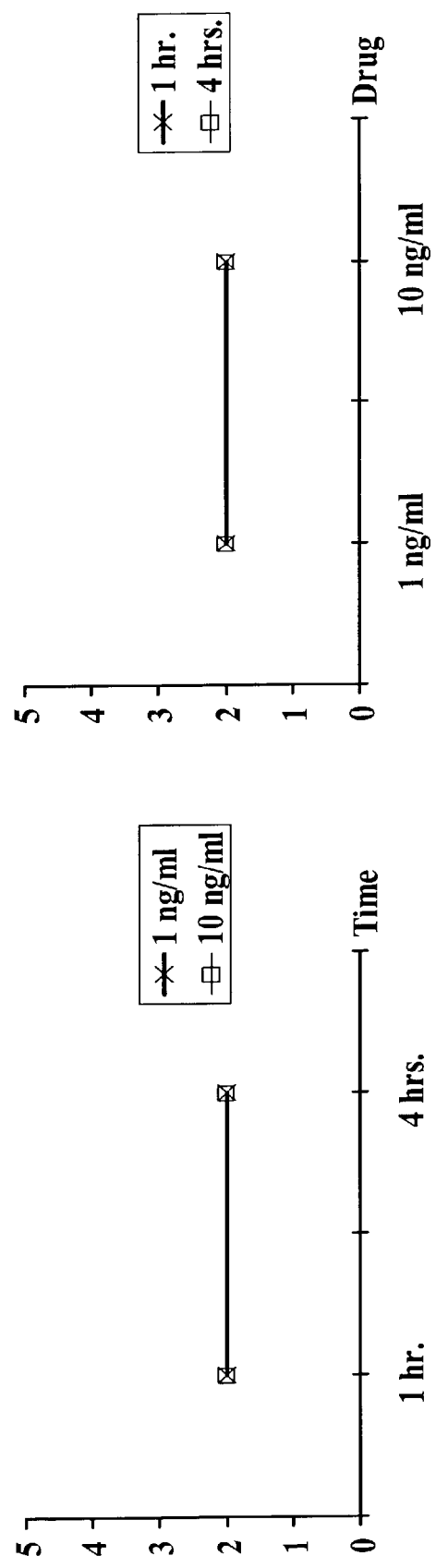
Figure 1B:
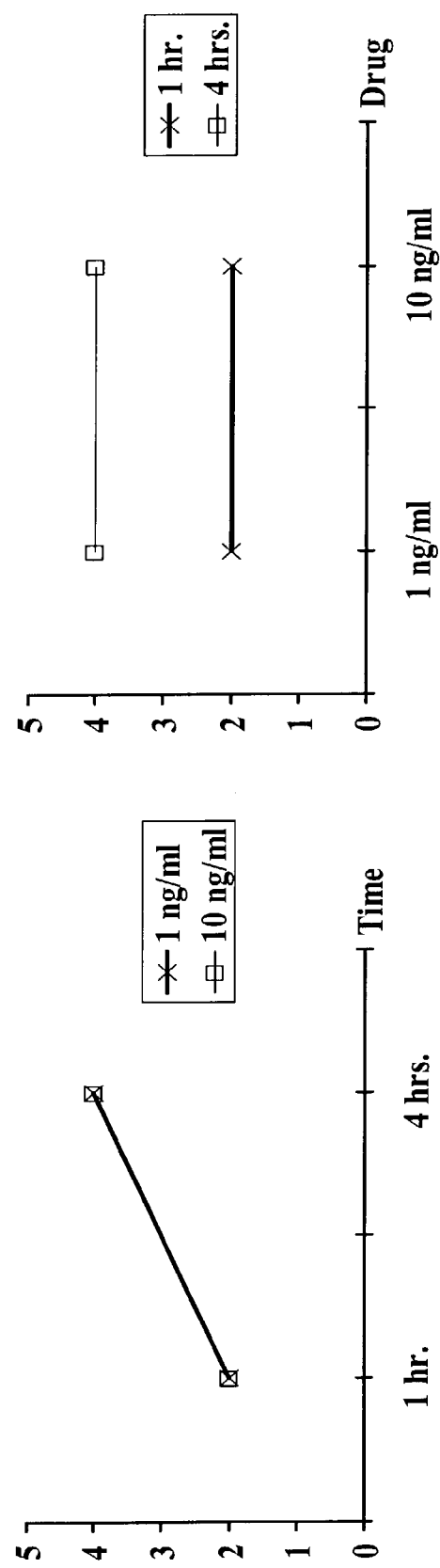
Figure 1C:
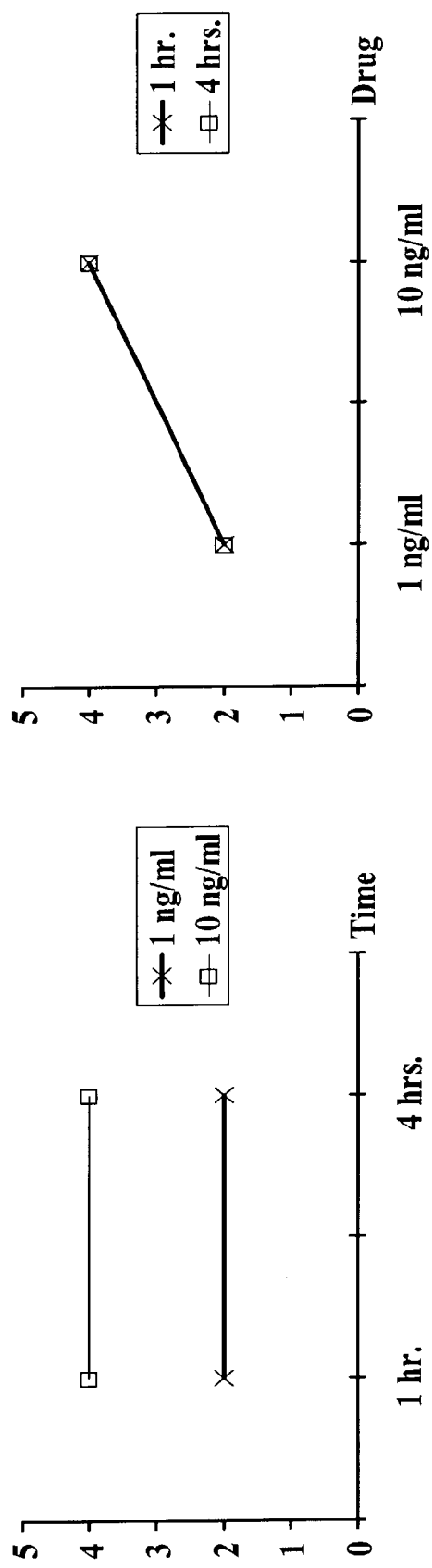

One supervised classification scheme is illustrated by Golub et al., 1999, *Science* 286: 531. These workers defined an idealized expression pattern c that corresponds to a gene that is uniformly high in one subclass of a complex trait and uniformly low in other subclasses. Next, the expression patterns of a plurality of genes in a series of specimens were examined to identify genes that correlate to expression pattern c by more than would be expected by chance. Specifically, Golub et al. found, using expression data of 6817 genes in 38 acute leukemia samples, roughly 1100 genes that were more highly correlated with a particular leukemia type distinction than would be expected by chance. This correlation demonstrates that classification can be based on expression data. Golub et al. used 50 of the 1100 genes to construct a class predictor capable of distinguishing whether a given patient has acute myeloid leukemia (AML) versus acute lymphoblastic leukemia (ALL). Twenty-five of the fifty genes are more highly expressed in ALL patients whereas the other twenty-five genes are more highly express in ALL patients. Golub et al. demonstrated that the set of fifty genes serves as a reliable predictor for identifying new samples as AML or ALL. One of skill in the art will appreciate that the supervised classification method of Golub et al. is not limited to gene expression data but is, in fact, applicable to any form of cellular constituent data obtained in step 102 (FIG. 1).

As mentioned above, another supervised classification scheme is linear discriminant analysis. Linear discriminant analysis is reviewed in Ripley, 1996, *Pattern Recognition and Neural Networks*, Cambridge University Press, New York, as well as Hastie et al., 1995, Penalized Discriminant Analysis, *The Annals of Statistics* 23: 73-102. In this approach, a score is given to a gene depending on how consistent its expression profile is with the profiles of genes belonging to one of two pre-specified categories. A positive score is given to a gene that is more similar to the genes in one category, whereas a negative scores is given to a gene that is more similar to genes in the other category. In determining similarity, certain measurements are more important than others. More weight is placed on more important measurements. This approach is used for data sets that have a large number of irrelevant measurements in the expression profile. In particular, the linear discriminant analysis approach may be successfully applied to a leukemia data set that includes measurements of certain ubiquitously expressed genes that are useless for typing. One of skill in the art will appreciate that the linear discriminant analysis classification method is applicable to any form of cellular constituent data obtained in step 102 (FIG. 1).

Additional classification schemes include, but are not limited to, linear regression methods such as multiple linear regression (MLR), partial least squares regression (PLS) and principal components regression (PCR). Such methods are described, for example in (Brereton, 1992, *Multivariate Pattern Recognition in Chemometrics*, Elsievier, Amsterdam; Brown et al., 1992, Chemometrics. Anal. Chem. 64, 22R-49R; Martens and Naes, 1989, *Multivariate Calibration*, John Wiley & Sons, New York; and Meloun et al., 1992, *Chemometrics for Analytical Chemistry* Vol 1, PC-aided Statistical Data Analysis, Ellis Horwood, Chichester, UK (1992). Furthermore, non-linear versions of these techniques may be used. See, for example, Frank et al., 1990, *Chemom. Intell. Lab. Sys.* 8: 109-119; Höskuldsson, 1992, *J. Chemom.* 6: 307-334; Kvalheim et al., 1985, *Anal. Chem.* 57: 2858-2864; Wold, 1992, *Chemom. Intell. Lab. Sys.* 14: 71-84; and Wythoff, 1993, *Chemom. Intell. Lab. Sys.* 20: 129-148. A related approach that may be used is artificial neural networks (ANNs).

The goal of supervised learning is to find a model or mapping that will correctly associate the inputs with the targets. Thus, the basic idea in these supervised learning techniques is that there are minimally four data sets to be studied. The "training data" consist of (i) a matrix of s rows and n columns in which s is the number of objects and n the number of variables and (ii) a second matrix, again consisting of s rows and typically 1 or two columns, in which the columns represent the variable(s) whose value(s) it is desired to know and which for the training set have actually been determined by some existing, "benchmark" method. This variable is paired with the patterns in the same row in (i). The "test data" also consist of two matrices, (iii) and (iv), corresponding to those in (i) and (ii) above, but the test set contains different objects. As the name suggests, this second pair is used to test the accuracy of the system. Alternatively, they may be used to cross-validate the model. That is to say, after construction of the model using the training set (i, ii) the test data (iii) (these may be new spectra) are then "passed" through the calibration model so as to obtained the model's prediction of results. These may then be compared with the known, expected responses (iv). As in all other data analysis techniques, these supervised learning methods are not immune from sensitivity to badly chosen initial data. See, for example, Zupan and Gasteiger, 1993, *Neural Networks for Chemists: An Introduction*, VCH Verlagsgeesellschaft, Weinheim. Therefore, the exemplars for the training set must be carefully chosen.

5.13. Other Exemplary Forms of Analysis

Additional types of analysis that can be performed by analysis pipeline 412 are described in more detail below.

Analysis of variance (ANOVA) is described in *Statistics For Experimenters*, Box, Hunter and Hunter, John Wiley and Sons, 1978; Siegel et al., *Nonparametric statistics for the behavioural sciences*, McGraw Hill, $2^{nd}$ edition, 1998; Conover, *Practical Nonparametric Statistics*, John Wiley and Sons, $3^{rd}$ edition, 1998; Altman, *Practical Statistics for Medical Research*, CRC Press, 1991; Berry, *Statistical Methods in Medical Research*, Blackwell Science, Inc., 2001). ANOVA is a method for detecting whether there are statistical differences among the mean of different measurement groups. As an example, a measurement group can contain a set of gene expression levels under a particular drug treatment. In each group, there can be several replicated measurements of the same treatment. Examples of standard statistical techniques applied to analyze the measured results of an experiment design include t-tests (paired and unpaired), one-way or two-way ANOVA, factorial and fractional factorial designs (e.g., two-level designs), the method of least squares (linear or nonlinear models), and response surface methodology. The statistical analysis methods are used to interpret the data derived from the experiment design, e.g., to indicate if any observed difference in the main effects between groups from the one or more factors is actually statistically valid.

Another form of analysis that can be performed by analysis pipeline 412 is the t-test. The t-test assesses whether the means of two groups are statistically different from each other. The t-test can be used, for example, to identify those cellular constituents that have significantly different mean abundances in various organisms or groups of organisms. For example, in the case where a plurality of organisms is divided into two groups, those that have been treated with a drug and those that have not, the t-test is used to find those cellular constituents that have a significantly different mean expression level in the organisms that were treated with a drug versus those organisms that were not treated with a drug. See, for example, Smith, 1991, *Statistical Reasoning*, Allyn and Bacon, Needham Heights, Mass., pp. 361-365. The t-test is represented by the following formula:

$$t = \frac{\overline{X}_T - \overline{X}_C}{\sqrt{\frac{\text{var}_T}{n_T} + \frac{\text{var}_C}{n_C}}}$$

where, the numerator is the numerator is the difference between the mean level of a given cellular constituent in a first group (T) and a second group (C); and $\text{var}_T$ is the variance (square of the deviation) in the level of the given cellular constituent in group T;

$\text{var}_C$ is the variance (square of the deviation) in the level of the given cellular constituent in group C;

$n_T$ is the number of organisms in group T; and $n_C$ is the number of organisms in group C.

The t-value will be positive if the first mean is larger than the second and negative if it is smaller. The significance of any t-value is determined by looking up the value in a table of significance to test whether the ratio is large enough to say that the difference between the groups is not likely to have been a chance finding. To test the significance, a risk level (called the alpha level) is set. In some embodiments of the present invention the alpha level is set at 0.05. This means that the five times out of a hundred there would be a statistically significant difference between the means even if there was none (i.e., by "chance"). In some embodiments, the alpha level is set at 0.025, 0.01 or 0.005. Further, to test significance, the number of degrees of freedom (df) for the test need to be determined. In the t-test, the degrees of freedom is the sum of the persons in both groups (T and C) minus 2. Given the alpha level, the df, and the t-value, it is possible to look the t-value up in a standard table of significance (see, for example, Table III of Fisher and Yates, *Statistical Tables for Biological, Agricultural, and Medical Research*, Longman Group Ltd., London) to determine whether the t-value is large enough to be significant. In some embodiments, a cellular constituent is considered to discriminate between two groups of organisms (e.g. a first group that is treated with a compound and a second group that is not treated with a compound) when t is 3 or greater, 4 or greater, 5 or greater, 6 or greater, or 7 or greater.

Another method that can be used by data analysis pipeline 412 is the paired t-test. The paired t-test assesses whether the means of two groups are statistically different from each other. The paired t-test is generally used when measurements are taken from the same organism before and after some perturbation, such as injection of a drug. For example, the paired t-test can be used to determine the significance of a difference in blood pressure before and after administration of a compound that affects blood pressure. The paired t-test is represented by the following formula:

$$t = \frac{\bar{d}}{\frac{S_d}{\sqrt{n}}}$$

where, the numerator is the paired sample mean;

$S_d$ is the paired sample deviation; and n is the number of pairs considered.

When statistics are calculated under the assumption that the data follow some common distribution such as the normal distribution it is termed parametric statistics. It follows that statistical tests based on these parametric statistics are called parametric statistical tests. Thus, when the data has a normal distribution, any number of well-known parametric statistical tests can be used. Such tests include, but are not limited to the t-tests described above, analysis of variance (ANOVA), repeated measures ANOVA, Pearson correlation, simple linear regression, nonlinear regression, multiple linear regression or multiple nonlinear regression. For example, regression can be used to see how two variables (two different cellular constituents) vary together.

Tests that do not make assumptions about the population distribution are referred to as non-parametric tests. Examples of non-parametric tests include, but are not limited to, a Wilcoxon signed-rank test, a Mann-Whitney test, a Kruskal-Wallis test, a Friedman test, a Spearman rank order correlation coefficient, a Kendall Tau analysis, and a nonparametric regression test.

5.14. References Cited

All references cited herein are incorporated herein by reference in their entirety and for all purposes to the same extent as if each individual publication or patent or patent application was specifically and individually indicated to be incorporated by reference in its entirety for all purposes.

6. Miscellaneous

The present invention can be implemented as a computer program product that comprises a computer program mechanism embedded in a computer readable storage medium. For instance, the computer program product could contain the program modules shown in FIG. 13. These program modules may be stored on a CD-ROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for processing a plurality of scans from one or more biological experiments, the method comprising:
    (A) assigning said plurality of scans to an experiment definition that is to be used to process said plurality of scans to form a plurality of profiles upon execution of said experiment definition;
    (B) storing said experiment definition in a database that comprises a plurality of experiment definitions;
    (C) executing said experiment definition to form said plurality of profiles from said plurality of scans; and
    (D) storing said plurality of profiles in a memory, a storage device, or a computer, thereby processing said plurality of scans.

2. The method of claim 1 wherein said executing step (C) is performed at a time prior to said storing step (B).

3. The method of claim 1 wherein said executing step (C) is performed at a time subsequent to said storing step (B).

4. The method of claim 1 wherein said experiment definition is a factorial design experiment definition and said assigning said plurality of scans to said experiment definition step (A) comprises:
    (i) generating an n-dimensional datacube by a method comprising
        (1) defining one or more experimental factors; and
        (2) defining one or more levels for each experimental factor defined in step (1); wherein,
    each cube in said n-dimensional datacube is the cross product of a level from each of the one or more experimental factors defined in step (1) of step (i);
    (ii) assigning a scan to a cube in said n-dimensional datacube; and
    (iii) repeating step (ii) until each scan in said plurality of scans has been assigned to a cube in said n-dimensional datacube.

5. The method of claim 4 wherein only a portion of the cubes in said n-dimensional datacube are assigned one or more scans.

6. The method of claim 4 wherein replicates are assigned to a first cube in said n-dimensional datacube.

7. The method of claim 6 wherein said first cube has an expected replicates count and an actual replicates count.

8. The method of claim 4 wherein a first experimental factor and a second experimental factor are defined in step (1) and said n-dimensional datacube is a two-dimensional datacube, wherein each cube in said two-dimensional datacube is the cross product of a level from said first experimental factor and a level from said second experimental factor.

9. The method of claim 4 wherein a first experimental factor, a second experimental factor and a third experimental factor are defined in step (1) and said n-dimensional datacube is a three-dimensional datacube, wherein each cube in said three-dimensional datacube is the cross product of a level from said first experimental factor, a level from said second experimental factor, and a level from said third experimental factor.

10. The method of claim 4 wherein between four and ten experimental factors are defined in step (1).

11. The method of claim 4 wherein more than ten experimental factors are defined in step (1).

12. The method of claim 4 wherein each said experimental factor in said one or more experimental factors is time, compound type, compound dosage, tissue type, or species.

13. The method of claim 4 wherein an experimental factor in said one or more experimental factors is designated a trend factor.

14. The method of claim 4, the method further comprising marking a level in an experimental factor in said one or more experimental factors as a baseline for building a ratio experiment or a re-ratio experiment.

15. The method of claim 1, wherein said experiment definition further comprises an error correction model for correcting errors in said plurality of scans, wherein, for each scan in said plurality of scans, said executing step (C) and storing step (D) comprise:
  (i) normalizing intensity measurements in said scan;
  (ii) applying said error correction model to a scan; and
  (iii) storing scan data that has been normalized by step (i) and error corrected by step (ii) as a profile that corresponds to said scan.

16. The method of claim 15, wherein said experiment definition further comprises a specification of a ratio between a first set of profiles and a second set of profiles, wherein each profile in said first set of profiles and each profile in said second set of profiles corresponds to a scan in said plurality of scans, wherein, said executing step (C) further comprises:
  taking said ratio between said first set of profiles and said second set of profiles in accordance with the specification of said ratio in said experiment definition.

17. The method of claim 15, wherein said experiment definition further comprises instructions for combining said plurality of profiles, wherein each profile in said plurality of profiles corresponds to a scan in said plurality of scans and wherein each scan that corresponds to a profile in said plurality of profiles is a replicate, wherein said executing step (C) further comprises combining said plurality of profiles to form a replicate profile using said instructions for combining.

18. The method of claim 15, wherein said experiment definition further comprises instructions for analyzing said plurality of profiles, wherein each profile in said plurality of profiles corresponds to a scan in said plurality of scans, wherein said executing step (C) further comprises analyzing said plurality of profiles using said instructions for analyzing said plurality of profiles.

19. The method of claim 1 wherein said assigning step (A) further comprises selecting said experiment definition from said database that comprises said plurality of experiment definitions.

20. The method of claim 1 wherein said database that comprises said plurality of experiment definitions is a relational database.

21. The method of claim 1 wherein a scan in said plurality of scans has between 10 and 100 intensity measurements in a spatial array.

22. The method of claim 1 wherein a scan in said plurality of scans has between 100 and 500 intensity measurements in a spatial array.

23. The method of claim 1 wherein a scan in said plurality of scans has between 500 and 1000 intensity measurements in a spatial array.

24. The method of claim 1 wherein a scan in said plurality of scans has between 1000 and 5000 intensity measurements in a spatial array.

25. The method of claim 1 wherein a scan in said plurality of scans has between 5000 and 10000 intensity measurements in a spatial array.

26. The method of claim 1 wherein a scan in said plurality of scans has more than 100 intensity measurements in a spatial array.

27. The method of claim 1 wherein a scan in said plurality of scans has less than 10000 intensity measurements in a spatial array.

28. The method of claim 1 wherein a scan in said plurality of scans represents levels of a plurality of cellular constituents in a biological sample that are measured during said one or more biological experiments.

29. The method of claim 28 wherein each cellular constituent in said plurality of cellular constituents is a gene, a protein, an mRNA, a cDNA, a cRNA, or a degree of protein modification.

30. The method of claim 15 wherein said error correction model is selected from a plurality of error correction models.

31. The method of claim 18 wherein said instructions for analyzing said plurality of profiles is a data analysis instruction set that is selected from a plurality of data analysis instruction sets.

32. The method of claim 15 wherein said normalizing step (i) comprises using a Z-score of intensity protocol, a median intensity normalization protocol, a log median intensity protocol, a Z-score standard deviation log of intensity protocol, a Z-score mean absolute deviation of log intensity protocol, a user normalization gene set protocol, or a ratio median intensity correction protocol.

33. The method of claim 1 wherein a scan in said plurality of scans represents a microarray or a two-dimensional gel.

34. The method of claim 33 wherein a scan in said plurality of scans represents a micro array having probes arranged with a density of 100 non identical probes per 1 $cm^2$ or higher.

35. The method of claim 33 wherein a scan in said plurality of scans represents a microarray having probes arranged with a density of at least 2,500 different probes per 1 $cm^2$.

36. The method of claim 33 wherein a scan in said plurality of scans represents a microarray having at least 20,000 probes.

37. The method of claim 18, wherein said instructions for analyzing said plurality of profiles comprise instructions for applying a classification scheme to intensity measurements in said plurality of profiles.

38. The method of claim 37 wherein said classification scheme is a supervised classification scheme.

39. The method of claim 38 wherein said supervised classification scheme is linear discriminant analysis or linear regression.

40. The method of claim 38 wherein said supervised classification scheme is multiple linear regression, partial least squares regression, principal component analysis or principle component regression.

41. The method of claim 37 wherein said classification scheme is an unsupervised classification scheme.

42. The method of claim 41 wherein said unsupervised classification scheme is hierarchical cluster analysis, non-hierarchical cluster analysis, a neural network, a self-organizing map, k-means clustering, or Jarvis-Patrick clustering.

43. The method of claim 41 wherein said unsupervised classification scheme is a hierarchical cluster analysis.

44. The method of claim 43 wherein said hierarchical cluster analysis is agglomerative clustering, clustering with Pearson correlation coefficients, or divisive clustering.

45. The method of claim 43 wherein said hierarchical cluster analysis is agglomerative clustering that uses a nearest neighbor algorithm, a farthest-neighbor algorithm, an average linkage algorithm, a centroid algorithm, or a sum of squares algorithm.

46. The method of claim 18, wherein said instructions for analyzing said plurality of profiles comprise instructions for applying a parametric statistical test.

47. The method of claim 46 wherein said parametric statistical test comprises fractional factorial design, analysis of variance, a t-test, least squares, a Pearson correlation, simple linear regression, nonlinear regression, multiple linear regression, or multiple nonlinear regression.

48. The method of claim 46 wherein said parametric statistical test comprises one-way analysis of variance, two-way analysis of variance, or repeated measures analysis of variance.

49. The method of claim 18 wherein said instructions for analyzing said plurality of profiles comprise instructions for applying a nonparametric statistical test.

50. The method of claim 49, wherein said nonparametric statistical test comprises a Wilcoxon signed-rank test, a Mann-Whitney test, a Kruskal-Wallis test, a Friedman test, a Spearman ranked order correlation coefficient, a Kendall Tau analysis, or a nonparametric regression test.

51. The method of claim 1 wherein said experiment definition is a combinatorial experiment definition and said assigning said plurality of scans to an experiment definition step (A) comprises:
 (i) defining one or more treatment groups;
 (ii) assigning a scan to a treatment group in said one or more treatment groups; and
 (iii) repeating step (ii) until each scan in said plurality of scans has been assigned to a treatment group.

52. A computer program product that comprises a computer program mechanism embedded in a computer readable storage medium, the computer program mechanism comprising:
 an n-dimensional data cube, wherein each cell in said n-dimensional data cube is formed by the cross product of a level of each experimental factor in a plurality of experimental factors, wherein a plurality of scans from one or more biological experiments are stored in said n-dimensional data cube;
 computer executable instructions for processing said scans into a plurality of profiles; and
 computer executable instructions for storing said plurality of profiles in a memory, a storage device, or a computer.

53. The computer program product of claim 52 wherein a single scan in said plurality of scans is assigned to a cell in said n-dimensional data cube.

54. The computer program product of claim 52 wherein more than one scan in said plurality of scans is assigned to a cell in said n-dimensional data cube.

55. The computer program product of claim 52 wherein said one or more biological experiments comprise microarray experiments or two-dimensional gel experiments.

56. The computer program product of claim 52 wherein said n-dimensional data cube is a two-dimensional data cube or a three-dimensional data cube.

57. The computer program product of claim 52 wherein said plurality of experimental factors consists of between four and ten experimental factors.

58. The computer program product of claim 52 wherein said plurality of experimental factors consists of more than ten experimental factors.

59. The computer program product of claim 52 wherein each experimental factor in said plurality of experimental factors represents time, compound type, compound dosage, tissue type, or species in said one or more biological experiments.

60. The computer program product of claim 52 wherein an experimental factor in said plurality of experimental factors is a trend factor.

61. The computer program product of claim 52 wherein an experimental factor in said plurality of experimental factors is a baseline for a ratio or a re-ratio experiment.

62. The computer program product of claim 52 wherein said computer executable instructions for processing said scans comprise computer executable instructions for correcting errors in said one or more scans.

63. The computer program product of claim 62 wherein said computer executable instructions for processing said scans comprise computer executable instructions for normalizing intensity measurements in each scan in said plurality of scans.

64. The computer program product of claim 62 wherein said computer executable instructions for storing said plurality of profiles comprise, for each scan in said plurality of scans, computer executable instructions for storing, as a profile in said data structure, scan data that has been error corrected and normalized, wherein there is a one to one correspondence between each scan and each profile.

65. The computer program product of claim 64 wherein said profile is stored in the cell in said n-dimensional data cube in which the scan corresponding to said profile is stored.

66. The computer program product of claim 64 said data structure further comprising computer executable instructions for specifying a ratio between a first set of profiles in said plurality of profiles and a second set of profiles in said plurality of profiles, wherein each profile in said first set of profiles and each profile in said second set of profiles corresponds to a scan in said plurality of scans.

67. The computer program product of claim 64 said data structure further comprising computer executable instructions for combining said plurality of profiles, wherein each profile in said plurality of profiles corresponds to a scan in said plurality of scans and wherein each scan that corresponds to a profile in said plurality of profiles is a replicate.

68. The computer program product of claim 64 said data structure further comprising computer executable instructions for analyzing said plurality of profiles, where each profile in said plurality of profiles corresponds to a scan in said plurality of scans.

69. The computer program product of claim 64, wherein said data structure is stored in a relational database.

70. The computer program product of claim 52 wherein a scan in said plurality of scans has between 10 and 100 intensity measurements in a spatial array.

71. The computer program product of claim 52 wherein a scan in said plurality of scans has between 100 and 500 intensity measurements in a spatial array.

72. The computer program product of claim 52 wherein a scan in said plurality of scans has between 500 and 1000 intensity measurements in a spatial array.

73. The computer program product of claim 52 wherein a scan in said plurality of scans has between 1000 and 5000 intensity measurements in a spatial array.

74. The computer program product of claim 52 wherein a scan in said plurality of scans has between 5000 and 10000 intensity measurements in a spatial array.

75. The computer program product of claim 52 wherein a scan in said plurality of scans has more than 100 intensity measurements in a spatial array.

76. The computer program product of claim 52 wherein a scan in said plurality of scans has less than 10000 intensity measurements in a spatial array.

77. The computer program product of claim 52 wherein a scan in said plurality of scans represents levels of a plurality of cellular constituents in a biological sample that are measured during said one or more biological experiments.

78. The computer program product of claim 77 wherein each cellular constituent in said plurality of cellular constituents is a gene, a protein, an mRNA, a cDNA, a cRNA, or a degree of protein modification.

79. The computer program product of claim 63 wherein said computer executable instructions for normalizing intensity measurements in each scan in said plurality of scans comprise computer executable instructions for using a Z-score of intensity protocol, a median intensity normalization protocol, a log median intensity protocol, a Z-score standard deviation log of intensity protocol, a Z-score mean absolute deviation of log intensity protocol, a user normalization gene set protocol, or a ratio median intensity correction protocol.

80. The computer program product of claim 52 wherein a scan in said plurality of scans represents data from a micro array or a two-dimensional gel.

81. The computer program product of claim 52 wherein a scan in said plurality of scans represents data from a microarray having probes arranged with a density of 100 non-identical probes per 1 cm$^2$ or higher.

82. The computer program product of claim 52 wherein a scan in said plurality of scans represents data from a microarray having probes arranged with a density of at least 2,500 different probes per 1 cm$^2$.

83. The computer program product of claim 52 wherein a scan in said plurality of scans represents data from a microarray having at least 20,000 probes.

84. The computer program product of claim 68 wherein said computer executable instructions for analyzing said plurality of profiles comprise computer executable instructions for applying a classification scheme to intensity measurements in said plurality of profiles.

85. The computer program product of claim 84 wherein said classification scheme is a supervised classification scheme.

86. The computer program product of claim 85 wherein said supervised classification scheme is linear discriminant analysis or linear regression.

87. The computer program product of claim 85 wherein said supervised classification scheme is multiple linear regression, partial least squares regression, principal component analysis or principle component regression.

88. The computer program product of claim 84 wherein said classification scheme is an unsupervised classification scheme.

89. The computer program product of claim 84 wherein said unsupervised classification scheme is hierarchical cluster analysis, non-hierarchical cluster analysis, a neural network, a self-organizing map, k-means clustering, or Jarvis-Patrick clustering.

90. The computer program product of claim 89 wherein said unsupervised classification scheme is a hierarchical cluster analysis.

91. The computer program product of claim 90 wherein said hierarchical cluster analysis is agglomerative clustering, clustering with Pearson correlation coefficients, or divisive clustering.

92. The computer program product of claim 90 wherein said hierarchical cluster analysis is agglomerative clustering that uses a nearest neighbor algorithm, a farthest-neighbor algorithm, an average linkage algorithm, a centroid algorithm, or a sum of squares algorithm.

93. The computer program product of claim 68, wherein said computer executable instructions for analyzing said plurality of profiles comprise computer executable instructions for applying a parametric statistical test.

94. The computer program product of claim 93 wherein said parametric statistical test comprises fractional factorial design, analysis of variance, a t-test, least squares, a Pearson correlation, simple linear regression, nonlinear regression, multiple linear regression, or multiple nonlinear regression.

95. The computer program product of claim 93 wherein said parametric statistical test comprises one-way analysis of variance, two-way analysis of variance, or repeated measures analysis of variance.

96. The computer program product of claim 68 wherein said computer executable instructions for analyzing said plurality of profiles comprise computer executable instructions for applying a nonparametric statistical test.

97. The computer program product of claim 96 wherein said nonparametric statistical test comprises a Wilcoxon signed-rank test, a Mann-Whitney test, a Kruskal-Wallis test, a Friedman test, a Spearman ranked order correlation coefficient, a Kendall Tau analysis, or a nonparametric regression test.

98. A computer program product for use in conjunction with a computer system, the computer program product comprising a computer readable storage medium and a computer program mechanism embedded therein, the computer program mechanism comprising:

a database that comprises a plurality of experiment definitions; and an experiment definition system for processing a plurality of scans from one or more biological experiments, said experiment definition system comprising:

(A) computer executable instructions for assigning said plurality of scans to an experiment definition that is to be used to process said plurality of scans to form a plurality of profiles upon execution of said experiment definition;

(B) computer executable instructions for storing said experiment definition in said database;

(C) computer executable instructions for executing said experiment definition, thereby processing said plurality of scans into said plurality of profiles; and (D) computer executable instructions for storing said plurality of profiles in a memory, a storage device, or a computer.

99. The computer program product of claim 98 wherein said computer executable instructions for executing said experiment definition (C) are for execution at a time prior to said storing step (B).

100. The computer program product of claim 98 wherein said computer executable instructions for executing said experiment definition (C) are for execution at a time subsequent to said storing step (B).

101. The computer program product of claim 98 wherein said experiment definition is a factorial design experiment definition and said computer executable instructions for assigning said plurality of scans to said experiment definition (A) comprise:
  (i) computer executable instructions for generating an n-dimensional datacube by a method comprising
  (1) defining one or more experimental factors; and
  (2) defining one or more levels for each experimental factor defined in step (1); wherein,
  each cube in said n-dimensional datacube is the cross product of a level from each of the one or more experimental factors defined in step (1) of computer executable instructions (i);
  (ii) computer executable instructions for assigning a scan to a cube in said n-dimensional datacube; and
  (iii) computer executable instructions for repeating computer executable instructions (ii) until each scan in said plurality of scans has been assigned to a cube in said n-dimensional datacube.

102. The computer program product of claim 101 wherein only a portion of the cubes in said n-dimensional datacube are assigned one or more scans.

103. The computer program product of claim 101 wherein replicates are assigned to a first cube in said n-dimensional datacube.

104. The computer program product of claim 103 wherein said first cube has an expected replicates count and an actual replicates count.

105. The computer program product of claim 101 wherein a first experimental factor and a second experimental factor are defined in step (1) of said computer executable instructions (i) and said n-dimensional datacube is a two-dimensional datacube, wherein each cube in said two-dimensional datacube is the cross product of a level from said first experimental factor and a level from said second experimental factor.

106. The computer program product of claim 101 wherein a first experimental factor, a second experimental factor and a third experimental factor are defined in step (1) of said computer executable instructions (i) and said n-dimensional datacube is a three-dimensional datacube, wherein each cube in said three-dimensional datacube is the cross product of a level from said first experimental factor, a level from said second experimental factor, and a level from said third experimental factor.

107. The computer program product of claim 101 wherein between four and ten experimental factors are defined in step (1) of said computer executable instructions (i).

108. The computer program product of claim 101 wherein more than ten experimental factors are defined in step (1) of said computer executable instructions (i).

109. The computer program product of claim 101 wherein each said experimental factor in said one or more experimental factors is time, compound type, compound dosage, tissue type, or species.

110. The computer program product of claim 101 wherein an experimental factor in said one or more experimental factors is designated a trend factor.

111. The computer program product of claim 101, the experiment definition system further comprising computer executable instructions for marking a level in an experimental factor in said one or more experimental factors as a baseline for building a ratio or re-ratio experiment.

112. The computer program product of claim 98, wherein said experiment definition further comprises an error correction model for correcting errors in said plurality of scans, wherein, for each scan in said plurality of scans, said computer executable instructions for executing said experiment definition (C) and said computer executable instructions for storing (D) comprise:
  (i) computer executable instructions for normalizing intensity measurements in said scan;
  (ii) computer executable instructions for applying said error correction model to a scan; and
  (iii) computer executable instructions for storing scan data that has been normalized by step (i) and error corrected by step (ii) as a profile that corresponds to said scan.

113. The computer program product of 112, wherein said experiment definition further comprises computer executable instructions for specifying a ratio between a first set of profiles in said plurality of profiles and a second set of profiles in said plurality of profiles, wherein each profile in said first set of profiles and each profile in said second set of profiles corresponds to a scan in said plurality of scans, wherein, said computer executable instructions for executing said experiment definition (C) further comprise computer executable instructions for taking said ratio between said first set of profiles and said second set of profiles.

114. The computer program product of claim 112, wherein said experiment definition further comprises computer executable instructions for combining said plurality of profiles, wherein each profile in said plurality of profiles corresponds to a scan in said plurality of scans and wherein each scan that corresponds to a profile in said plurality of profiles is a replicate, said computer executable instructions for executing said experiment definition (C) further comprising:
  computer executable instructions for combining said plurality of profiles to form a replicate profile using said computer executable instructions for combining in said experiment definition.

115. The computer program product of 112, said experiment definition further comprising computer executable instructions for analyzing said plurality of profiles, wherein each profile in said plurality of profiles corresponds to a scan in said plurality of scans, said computer executable instructions for executing said experiment definition (C) further comprising:
  computer executable instructions for analyzing said plurality of profiles using said computer executable instructions for analyzing in said experiment definition.

116. The computer program product of claim 98 wherein said computer executable instructions for assigning said plurality of scans to an experiment definition further comprise computer executable instructions for selecting said experiment definition from said database that comprises said plurality of experiment definitions.

117. The computer program product of claim 98 wherein said database that comprises said plurality of experiment definitions is a relational database.

118. The computer program product of claim 98 wherein a scan in said plurality of scans has between 10 and 100 intensity measurements in a spatial array.

119. The computer program product of claim 98 wherein a scan in said plurality of scans has between 100 and 500 intensity measurements in a spatial array.

120. The computer program product of claim 98 wherein a scan in said plurality of scans has between 500 and 1000 intensity measurements in a spatial array.

121. The computer program product of claim 98 wherein a scan in said plurality of scans has between 1000 and 5000 intensity measurements in a spatial array.

122. The computer program product of claim 98 wherein a scan in said plurality of scans has between 5000 and 10000 intensity measurements in a spatial array.

123. The computer program product of claim 98 wherein a scan in said plurality of scans has more than 100 intensity measurements in a spatial array.

124. The computer program product of claim 98 wherein a scan in said plurality of scans has less than 10000 intensity measurements in a spatial array.

125. The computer program product of claim 98 wherein a scan in said plurality of scans represents levels of a plurality of cellular constituents in a biological sample that are measured during said one or more biological experiments.

126. The computer program product of claim 125 wherein each cellular constituent in said plurality of cellular constituents is a gene, a protein, an mRNA, a cDNA, a cRNA, or a degree of protein modification.

127. The computer program product of 112 wherein said experiment definition system further comprises computer executable instructions for selecting said error correction model from a plurality of error correction models for inclusion in said experiment definition.

128. The computer program product of claim 115 wherein said experiment definition system further comprises computer executable instructions for selecting a data analysis instruction set from a plurality of data analysis instruction sets for inclusion in said experiment definition.

129. The computer program product of 112 wherein said computer executable instructions for normalizing step (i) comprise computer executable instructions for using a Z-score of intensity protocol, a median intensity normalization protocol, a log median intensity protocol, a Z-score standard deviation log of intensity protocol, a Z-score mean absolute deviation of log intensity protocol, a user normalization gene set protocol, or a ratio median intensity correction protocol.

130. The computer program product of claim 98 wherein a scan in said plurality of scans represents a microarray or a two-dimensional gel.

131. The computer program product of claim 130 wherein a scan in said plurality of scans represents a microarray having probes arranged with a density of 100 non identical probes per 1 $cm^2$ or higher.

132. The computer program product of claim 115, wherein said computer executable instructions for analyzing said plurality of profiles comprise computer executable instructions for applying a classification scheme to intensity measurements in said plurality of profiles.

133. The computer program product of claim 132 wherein said classification scheme is a supervised classification scheme.

134. The computer program product of claim 133 wherein said supervised classification scheme is linear discriminant analysis or linear regression.

135. The computer program product of claim 134 wherein said supervised classification scheme is multiple linear regression, partial least squares regression, principal component analysis or principle component regression.

136. The computer program product of claim 132 wherein said classification scheme is an unsupervised classification scheme.

137. The computer program product of claim 136 wherein said unsupervised classification scheme is hierarchical cluster analysis, non-hierarchical cluster analysis, a neural network, a self-organizing map, k-means clustering, or Jarvis-Patrick clustering.

138. The computer program product of claim 136 wherein said unsupervised classification scheme is a hierarchical cluster analysis.

139. The computer program product of claim 138 wherein said hierarchical cluster analysis is agglomerative clustering, clustering with Pearson correlation coefficients, or divisive clustering.

140. The computer program product of claim 138 wherein said hierarchical cluster analysis is agglomerative clustering that uses a nearest neighbor algorithm, a farthest-neighbor algorithm, an average linkage algorithm, a centroid algorithm, or a sum of squares algorithm.

141. The computer program product of claim 115 wherein said computer executable instructions for analyzing said plurality of profiles comprise computer executable instructions for applying a parametric statistical test.

142. The computer program product of claim 141 wherein said parametric statistical test comprises fractional factorial design, analysis of variance, a t-test, least squares, a Pearson correlation, simple linear regression, nonlinear regression, multiple linear regression, or multiple nonlinear regression.

143. The computer program product of claim 141 wherein said parametric statistical test comprises one-way analysis of variance, two-way analysis of variance, or repeated measures analysis of variance.

144. The computer program product of claim 115 wherein said computer executable instructions for analyzing said plurality of profiles comprise computer executable instructions for applying a nonparametric statistical test.

145. The computer program product of claim 144 wherein said nonparametric statistical test comprises a Wilcoxon signed-rank test, a Mann-Whitney test, a Kruskal-Wallis test, a Friedman test, a Spearman ranked order correlation coefficient, a Kendall Tau analysis, or a nonparametric regression test.

146. The computer program product of claim 98 wherein said experiment definition is a combinatorial experiment definition and said computer executable instructions for assigning said plurality of scans to said experiment definition (A) comprise:
   (i) computer executable instructions for defining one or more treatment groups;
   (ii) computer executable instructions for assigning a scan to a treatment group in said one or more treatment groups; and
   (iii) computer executable instructions for repeating computer executable instructions (ii) until each scan in said plurality of scans has been assigned to a treatment group.

147. A computer system for processing a plurality of scans from one or more biological experiments, the computer system comprising:
   a central processing unit; and
   a memory, coupled to the central processing unit, the memory storing (a) a database that comprises a plurality of experiment definitions, and (b) an experiment definition system, said experiment definition system comprising:
(A) computer executable instructions for assigning said plurality of scans to an experiment definition that is to be used to process said plurality of scans to form a plurality of profiles upon execution of said experiment definition;
(B) computer executable instructions for storing said experiment definition in said database;
(C) computer executable instructions for executing said experiment definition thereby forming said plurality of profiles; and
(D) computer executable instructions for storing said plurality of profiles in a memory, a storage device, or a computer, thereby processing said plurality of scans.

148. The computer system of claim 147 wherein said experiment definition is a factorial design experiment definition and said computer executable instructions for assigning said plurality of scans to said experiment definition (A) comprise:
(i) computer executable instructions for generating an n-dimensional datacube by a method comprising
 (1) defining one or more experimental factors; and
 (2) defining one or more levels for each experimental factor defined in step (1); wherein,
(i) each cube in said n-dimensional datacube is the cross product of a level from each of the one or more experimental factors defined in step (1) of computer executable instructions (i);
(ii) computer executable instructions for assigning a scan to a cube in said n-dimensional datacube; and
(iii) computer executable instructions for repeating computer executable instructions (ii) until each scan in said plurality of scans has been assigned to a cube in said n-dimensional datacube.

149. The computer system of claim 147, wherein said experiment definition further comprises an error correction model for correcting errors in said plurality of scans wherein, for each scan in said plurality of scans, said computer executable instructions for executing said experiment definition (C) and said computer executable instructions for storing (D) comprise:
(i) computer executable instructions for normalizing intensity measurements in said scan;
(ii) computer executable instructions for applying said error correction model to a scan; and
(iii) computer executable instructions for storing scan data that has been normalized by step (i) and error corrected by step (ii) as a profile that corresponds to said scan.

150. The computer system of claim 147, wherein said experiment definition further comprises computer executable instructions for specifying a ratio between a first set of profiles in said plurality of profiles and a second set of profiles in said plurality of profiles, wherein each profile in said first set of profiles and each profile in said second set of profiles corresponds to a scan in said plurality of scans, wherein, said computer executable instructions for executing said experiment definition (C) further comprise computer executable instructions for taking said ratio between said first set of profiles and said second set of profiles.

151. The computer system of claim 147, wherein said experiment definition further comprises computer executable instructions for combining said plurality of profiles, wherein each profile in said plurality of profiles corresponds to a scan in said plurality of scans and wherein each scan that corresponds to a profile in said plurality of profiles is a replicate, said computer executable instructions for executing said experiment definition (C) further comprising:
computer executable instructions for combining said plurality of profiles to form a replicate profile using said computer executable instructions for combining in said experiment definition.

152. The computer system of claim 147, said experiment definition further comprising computer executable instructions for analyzing said plurality of profiles, wherein each profile in said plurality of profiles corresponds to a scan in said plurality of scans, said computer executable instructions for executing said experiment definition (C) further comprising:
computer executable instructions for analyzing said plurality of profiles using said computer executable instructions for analyzing in said experiment definition.

153. The computer system of claim 147, wherein a scan in said plurality of scans represents a microarray or a two-dimensional gel.

154. The computer system of claim 147 wherein said experiment definition is a combinatorial experiment definition and said computer executable instructions for assigning said plurality of scans to said experiment definition (A) comprise:
(i) computer executable instructions for defining one or more treatment groups;
(ii) computer executable instructions for assigning a scan to a treatment group in said one or more treatment groups; and
(iii) computer executable instructions for repeating computer executable instructions (ii) until each scan in said plurality of scans has been assigned to a treatment group.

155. The method of claim 1, wherein a scan in said plurality of scans comprises mass spectrometry data.

156. The method of claim 155, wherein said mass spectrometry data comprises liquid chromatography/mass spectrometry data.

157. The method of claim 155, wherein said mass spectrometry data comprises matrix-assisted laser desorption/ionization-time of flight mass spectrometry data.

158. The computer program product of claim 98, wherein a scan in said plurality of scans comprises mass spectrometry data.

159. The computer program product of claim 158, wherein said mass spectrometry data comprises liquid chromatography/mass spectrometry data.

160. The computer program product of claim 158, wherein said mass spectrometry data comprises matrix-assisted laser desorption/ionization-time of flight mass spectrometry data.

161. The computer system of claim 147, wherein a scan in said plurality of scans comprises mass spectrometry data.

162. The computer system of claim 161, wherein said mass spectrometry data comprises liquid chromatography/mass spectrometry data.

163. The computer system of claim 161, wherein said mass spectrometry data comprises matrix-assisted laser desorption/ionization-time of flight mass spectrometry data.

* * * * *